United States Patent
Hirao et al.

(10) Patent No.: US 10,695,362 B2
(45) Date of Patent: Jun. 30, 2020

(54) STABILIZATION METHOD OF FUNCTIONAL NUCLEIC ACID

(71) Applicant: TAGCYX BIOTECHNOLOGIES INC., Tokyo (JP)

(72) Inventors: Ichiro Hirao, Komae (JP); Michiko Hirao, Yokohama (JP); Shuang Liu, Yokohama (JP); Iwao Nozawa, Yokohama (JP)

(73) Assignee: TAGCYX BIOTECHNOLOGIES INC., Tokyo (JP)

( * ) Notice: Subject to any disclaimer, the term of this patent is extended or adjusted under 35 U.S.C. 154(b) by 0 days.

(21) Appl. No.: 15/959,809

(22) Filed: Apr. 23, 2018

(65) Prior Publication Data
US 2018/0243329 A1    Aug. 30, 2018

Related U.S. Application Data

(62) Division of application No. 13/107,175, filed on May 13, 2011, now abandoned.

(60) Provisional application No. 61/334,696, filed on May 14, 2010.

(51) Int. Cl.
| | | |
|---|---|---|
| *C12N 15/115* | (2010.01) | |
| *A61K 31/7088* | (2006.01) | |
| *C12N 15/11* | (2006.01) | |
| *C12N 15/67* | (2006.01) | |

(52) U.S. Cl.
CPC ........ *A61K 31/7088* (2013.01); *C12N 15/111* (2013.01); *C12N 15/115* (2013.01); *C12N 15/67* (2013.01); *C12N 2310/13* (2013.01); *C12N 2310/14* (2013.01); *C12N 2310/3519* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 5,683,985 | A | 11/1997 | Chu et al. |
| 5,840,867 | A | 11/1998 | Toole et al. |
| 7,998,940 | B2 | 8/2011 | Diener et al. |
| 2005/0020521 | A1 | 1/2005 | Rana |
| 2006/0128650 | A1 | 6/2006 | Xu |
| 2009/0012022 | A1 | 1/2009 | Milner et al. |
| 2009/0023672 | A1 | 1/2009 | Inoue et al. |
| 2011/0055965 | A1 | 3/2011 | Abe et al. |

FOREIGN PATENT DOCUMENTS

| | | |
|---|---|---|
| JP | H6-508022 | 9/1994 |
| JP | 2005-523703 A | 8/2005 |
| JP | 2006-500014 A | 1/2006 |
| JP | 2008-512097 | 4/2008 |
| WO | WO 03/091432 A1 | 11/2003 |
| WO | WO 2004/015107 A2 | 2/2004 |
| WO | WO 2006/080262 A1 | 8/2006 |
| WO | WO 2006/125977 A2 | 11/2006 |
| WO | WO 2009/102081 A1 | 8/2009 |

OTHER PUBLICATIONS

Hirao et al. (Biochemie (2018) 145: 15-21). (Year: 2018).*
Chua et al., "Nick-containing oligonucleotides as human topoisomerase I inhibitors", Bioorganic & Medicinal Chemistry Letters, vol. 19 (2009) pp. 618-623.
Elmen et al., "Locked nucleic acid (LNA) mediated improvements in siRNA stability and functionality", Nucleic Acids Research, vol. 33, No. 1, 2005, pp. 439-447.
Extended European Search Report issued in European Patent Application No. 11772007.8 dated Sep. 1, 2014.
Hirao et al., "Unusual Single-Stranded DNA Structures: Extraordinarily Thermo-Stable Mini-Hairpin", Protein, Nucleic Acid and Enzyme (PNE), vol. 40, No. 10, 1995, pp. 1583-1591, with partial translation.
Hirao, "Extraordinarily thermo-stable hairpin structures: Partial structure of single-strand nucleic acids", The Journal of Biochemistry (JB), vol. 66, No. 11, Nov. 1994, pp. 1414-1418, with partial translation.
International Search Report dated Jul. 19, 2011 for Application No. PCT/JP2011/059619.
Jiang et al., "A bi-functional siRNA construct induces RNA interference and also primes PCR amplification for its own quantification", Nucleic Acids Research, vol. 33, No. 18, 2005, e151, seven pages.
Kuznetsova et al., "Efficient Synthesis of DNA Dumbbells Using Template-Induced Chemical Ligation in Double-Stranded Polynucleotides Closed by Minihairpin Fragments", Antisense & Nucleic Acid Drug Development, vol. 9 (1999) pp. 95-100.
Ueno et al., "Synthesis of nuclease-resistant siRNAs possessing universal overhangs", Bioorganic & Medicinal Chemistry, vol. 17, 2009, pp. 1974-1981.
Yoshizawa et al., "Stable Short Hairpin DNAs: Structures and Functions of GNA Trinucleotide Loop Hairpins", Abstract 2E237, p. 893, 1994, with partial translation.

(Continued)

*Primary Examiner* — J. E Angell
(74) *Attorney, Agent, or Firm* — Birch, Stewart, Kolasch & Birch, LLP

(57) ABSTRACT

This invention is intended to enhance and improve the resistance of a single- or double-stranded nucleic acid fragment comprising a base sequence of a functional nucleic acid to degradation by nucleolytic enzymes in a simple and cost-effective manner. The single- or double-stranded nucleic acid fragment comprises, ligated to at least one end thereof, hairpin-shaped DNA comprising: (A) a nucleic acid region comprising 2 to 5 arbitrary nucleotides; (B) a nucleic acid region comprising a "gna" or "gnna" base sequence, wherein each "n" represents "g", "t", "a", or "c", a base analogue, or a modified base; and (C) a nucleic acid region comprising a base sequence complementary to the nucleic acid region (A), sequentially from the 5' end toward the 3' end.

8 Claims, 29 Drawing Sheets

Specification includes a Sequence Listing.

(56) References Cited

OTHER PUBLICATIONS

Harborth et al., "Sequence, Chemical, and Structural Variation of Small Interfering RNAs and Short Hairpin RNAs and the Effect on Mammalian Gene Silencing", Antisense and Nucleic Acid Drug Development, vol. 13, (2003) pp. 83-105.

European Search Report issued in European Patent Application No. 18158543.1 dated May 2, 2018.

Rosemeyer et al., "Single-Stranded DNA: Replacement of Canonical by Base-Modified Nucleosides in the Minihairpin 5'd(GCGAAGC)-3' and Constructs with the Aptamer 5'-d(GGTTGGTGTGGTTGG)-3'1)", Helvetica Chimica Acta, vol. 87 (2004) pp. 536-553.

Yoshizawa et al., "GNA Trinucleotide Loop Sequences Producing Extraordinarily Stable DNA Minihairpins", Biochemistry, vol. 36 (1997) pp. 4761-4767.

* cited by examiner

Fig. 1
(A)
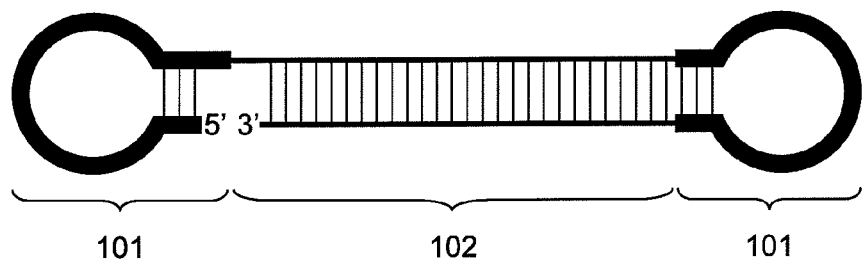
101  102  101
(B)
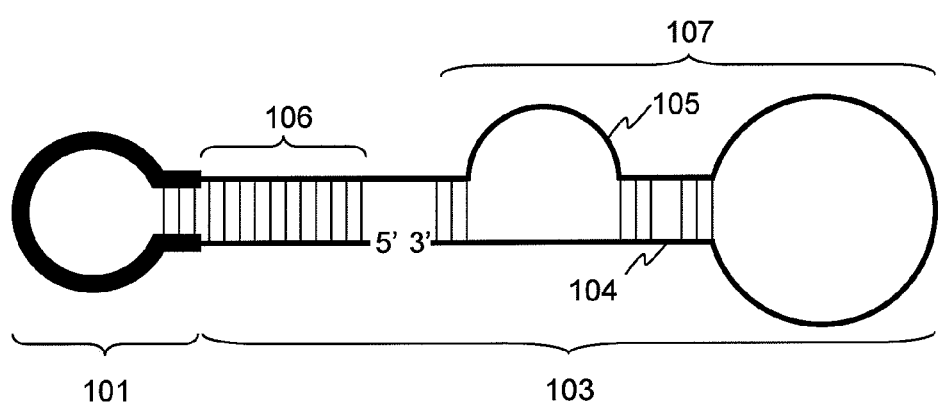
101  103
(C)
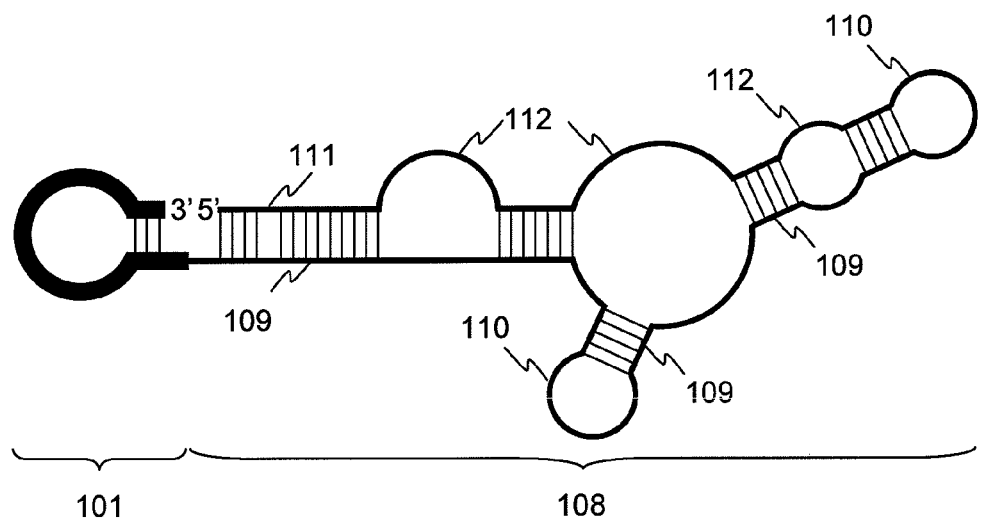
101  108

Fig. 3
(A)
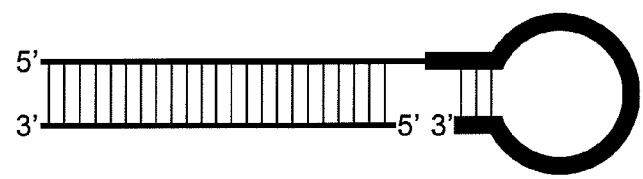
(B)
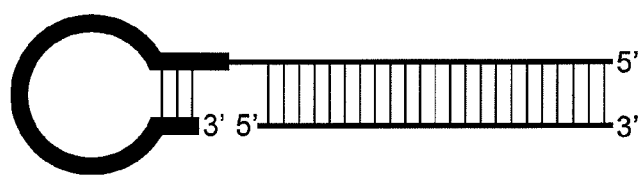
(C)
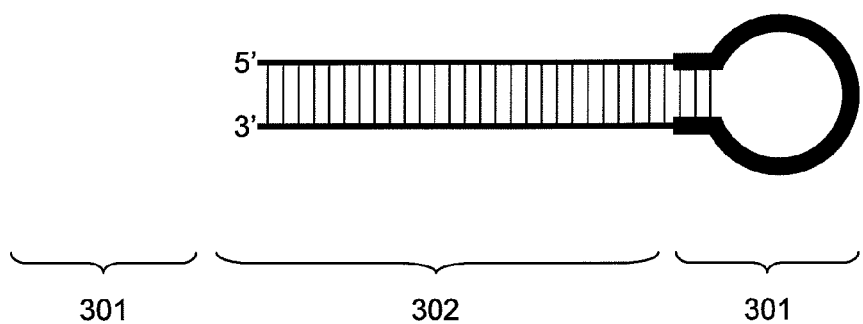

Fig. 4
(A)
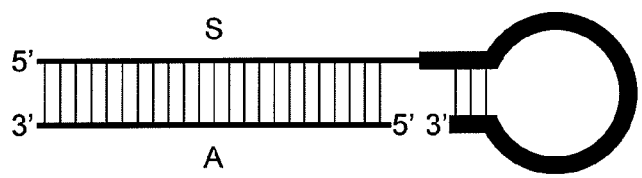
(B)
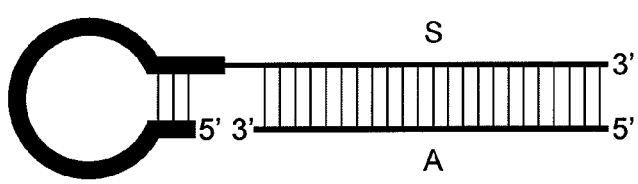
(C)
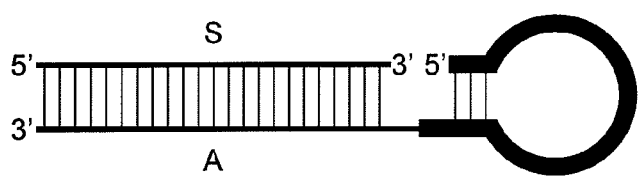
(D)
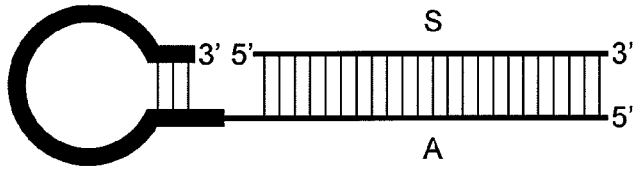
(E)
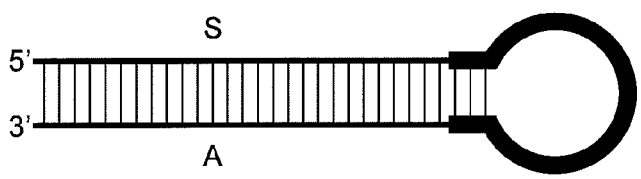
(F)
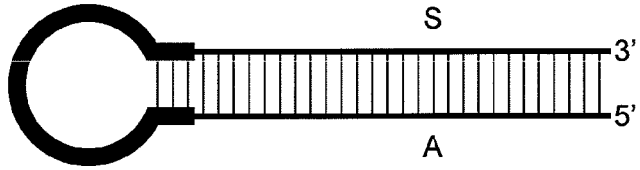
401   402   401

Fig. 5
(A)
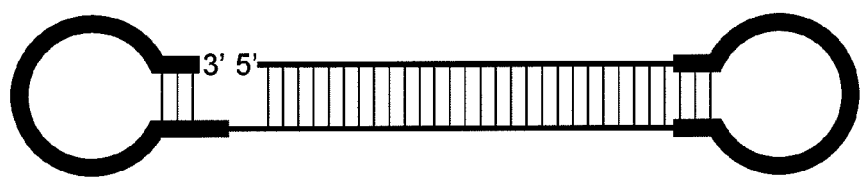
(B)
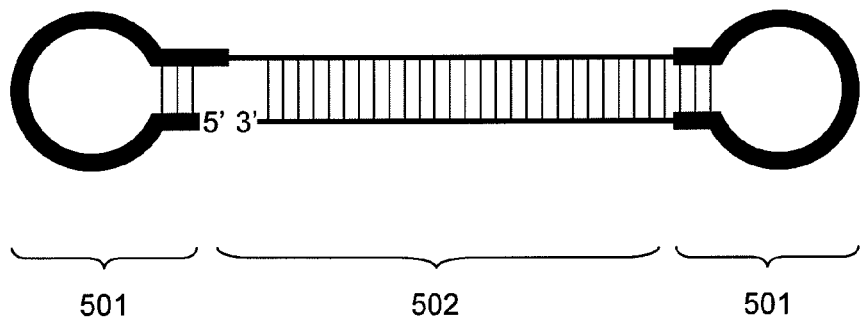

Fig. 6
(A) 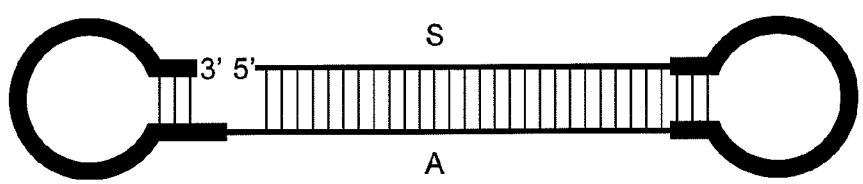
(B) 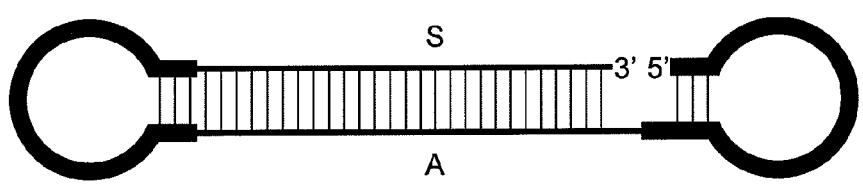
(C) 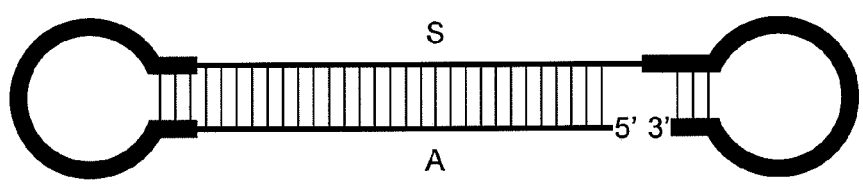
(D) 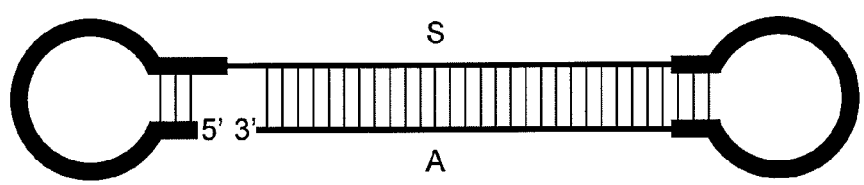

Fig. 7
(A) 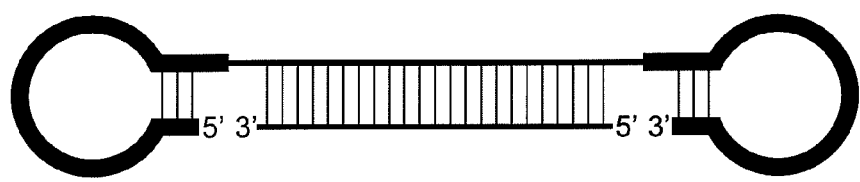
(B) 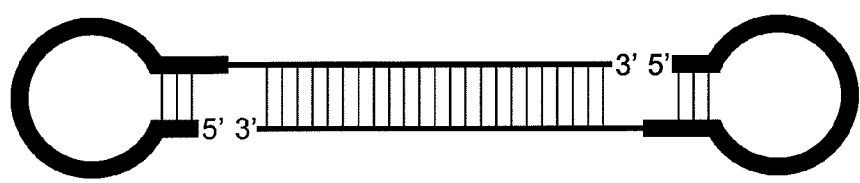
(C) 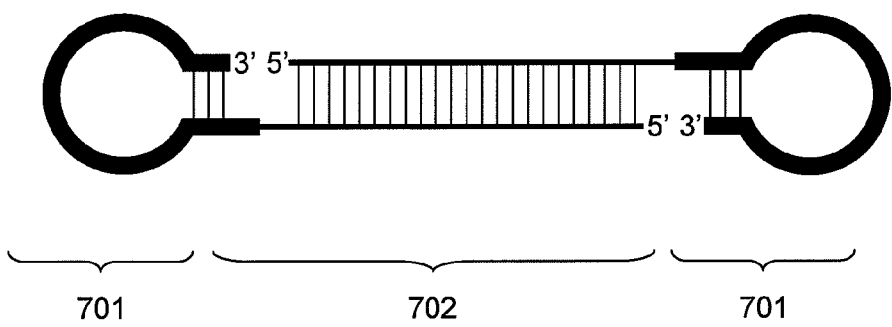

Fig. 8
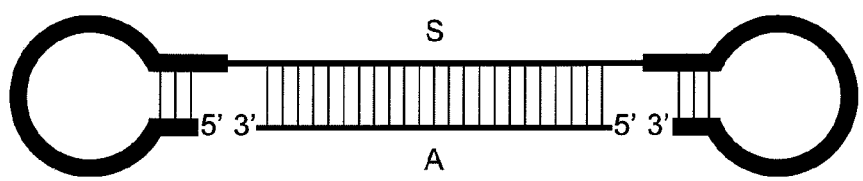
(A)
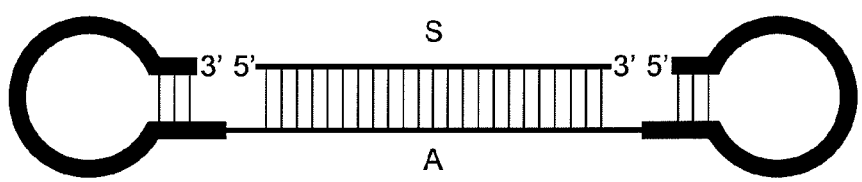
(B)
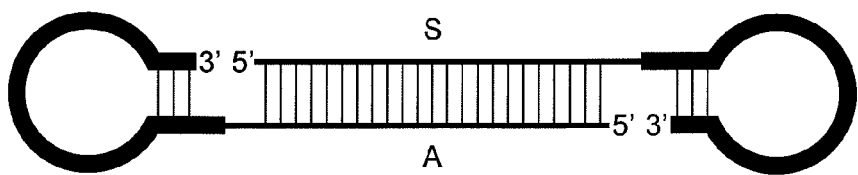
(C)
(D)
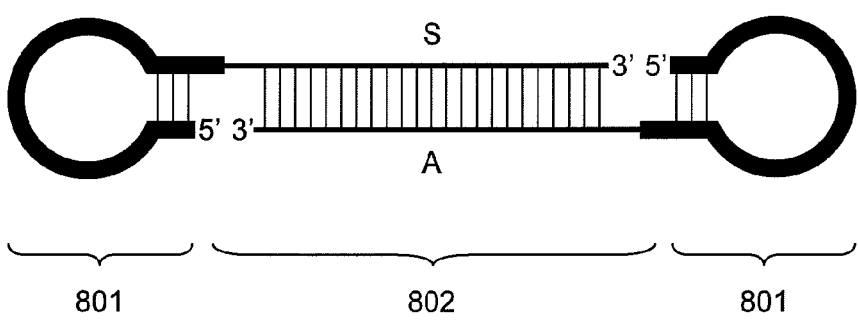

Fig. 9
(A)
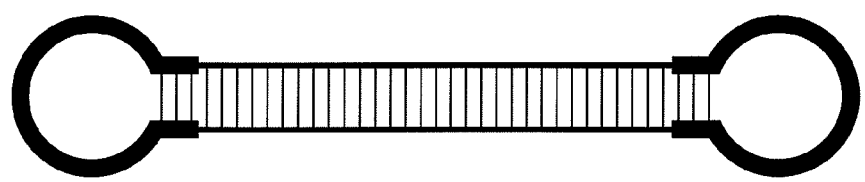
(B)
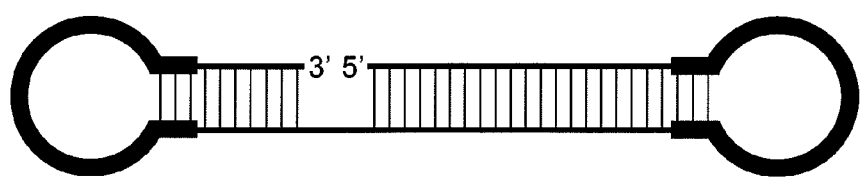
(C)
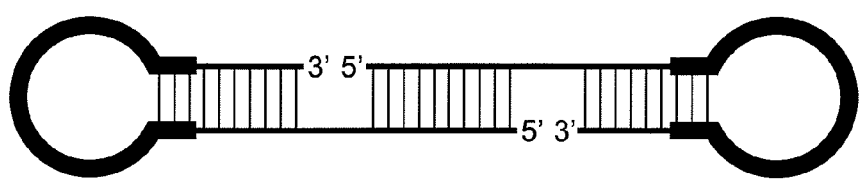
901　　　　　902　　　　　901

| | | SEQ ID NO: |
|---|---|---|
| Cont. I | 5'-GGAGCCUUCAGGAUUACAAGA-3'<br>3'-UUCCUCGGAAGUCCUAAUGUU-5' | 3<br>4 |
| Cont. II | 5'-GGAGCCUUCAGGAUUACAAtt-3'<br>3'-ttCCUCGGAAGUCCUAAUGUU-5' | 5<br>6 |
| Cont. III | 5'-AAGGAGCCUUCAGGAUUACAAGAUU-3'<br>3'-UUCCUCGGAAGUCCUAAUGUUCUAA-5' | 7<br>8 |

```
                3' ↓ 5'
           a  a g c AAGGAGCCUUCAGGAUUACAAGAUU g c  g
    a      a  g c g UUCCUCGGAAGUCCUAAUGUUCUAA c g  a     9
                                              5' ↑ 3'              10

3' ↓ 5'
           a  a g c g AAGGAGCCUUCAGGAUUACAAGAUU c g c  g
    b      a  g c g  UUCCUCGGAAGUCCUAAUGUUCUAA g c g   a    11
                                                5' ↑ 3'            12

3' ↓ 5'
           a   a g c AAGGAGCCUUCAGGAUUACAAGAUU g c  g a   13
    c      a   g c g UUCCUCGGAAGUCCUAAUGUUCUAA c g  a     14
                                               5' ↑ 3'

3' ↓ 5'
         a g c g AAGGAGCCUUCAGGAUUACAAGAUU c g c  g
    d  t g c g  UUCCUCGGAAGUCCUAAUGUUCUAA g c g   a t    15
                                              5' ↑ 3'          16
```

| e | 5'-AAGGAGCCUUCAGGAUUACAAGAUUGCGAAGC-3'<br>3'-CGAAGCGUUCCUCGGAAGUCCUAAUGUUCUAA-5' | 17<br>18 |

```
         5'-AAGGAGCCUUCAGGAUUACAAGAUU c g c  g
    f    3'-UUCCUCGGAAGUCCUAAUGUUCUAA g c g   a     19
                                         5' ↑ 3'          20

3' ↓ 5'
           a  a g c g AAGGAGCCUUCAGGAUUACAAGAUU-3'       21
    g         g c g c UUCCUCGGAAGUCCUAAUGUUCUAA-5'       22
```

Fig. 18

|  |  | SEQ ID NO: |
|---|---|---|
| Cont. 1 | 5'- CCTTGAA<u>GGGATTTCCC</u>TCC -3'<br>3'- GGAACTT<u>CCCTAAAGGG</u>AGG-5' | 33<br>34 |

Cont. 2   A$^A$ CCTTGAA<u>GGGATTTCCC</u>TCC $^A$A
          A$_A$ GGAACTT<u>CCCTAAAGGG</u>AGG$_A$ A A        A$^A$ GCTTGAA<u>GGGATTTCCC</u>TGC $^G$A
         A$_G$ CGAACTT<u>CCCTAAAGGG</u>ACG $_A$A B        A$^A$ GCTTGAA<u>GGGATTTCCC</u>TGC $^G$A       35
         A$_G$ CGAACT↑T<u>CCCTAAAGGG</u>ACG $_A$A
              5'↑3'

C        A$^A$ GC↓AA<u>GGGATTTCCC</u>TGC $^G$A        36
              3'↓5'
         A$_G$ CGTT<u>CCCTAAAGGG</u>ACG $_A$A

D        A$^A$ GC<u>GGGATTTCCC</u>GC $^G$A            37
         A$_G$ CG<u>CCCTAAAGGG</u> CG$_A$
                           5'↑3'

E        A$^A$ GC↓TTGAA<u>GGGATTTCCC</u>TGC $^G$A     38
              3'↓5'
         A$_G$ CGAACTT<u>CCCTAAAGGGA</u>↑CG $_A$A     39
                                5'↑3'

Fig. 21
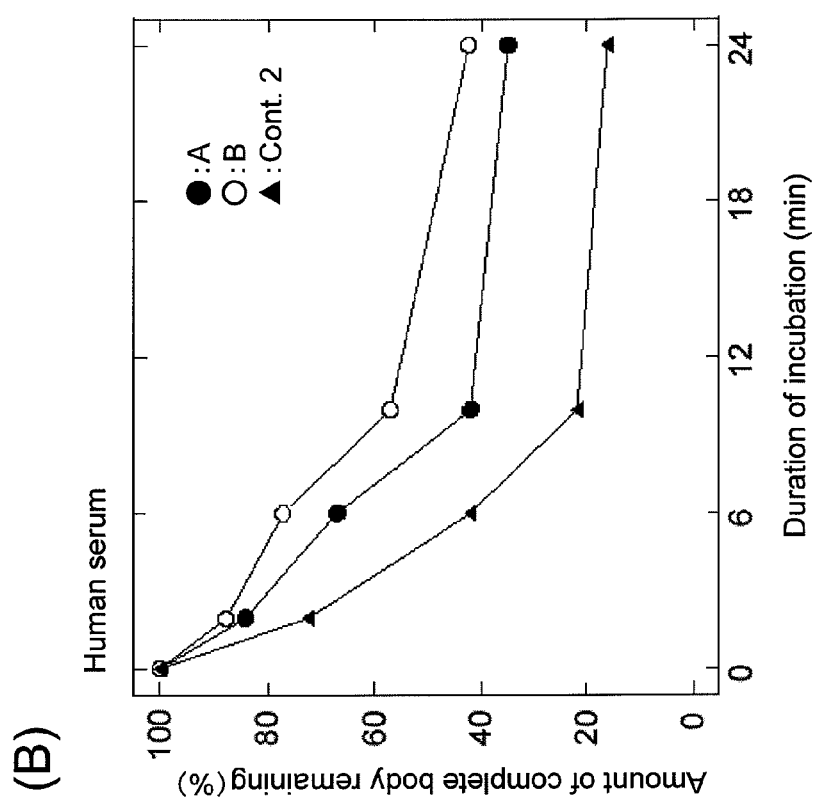
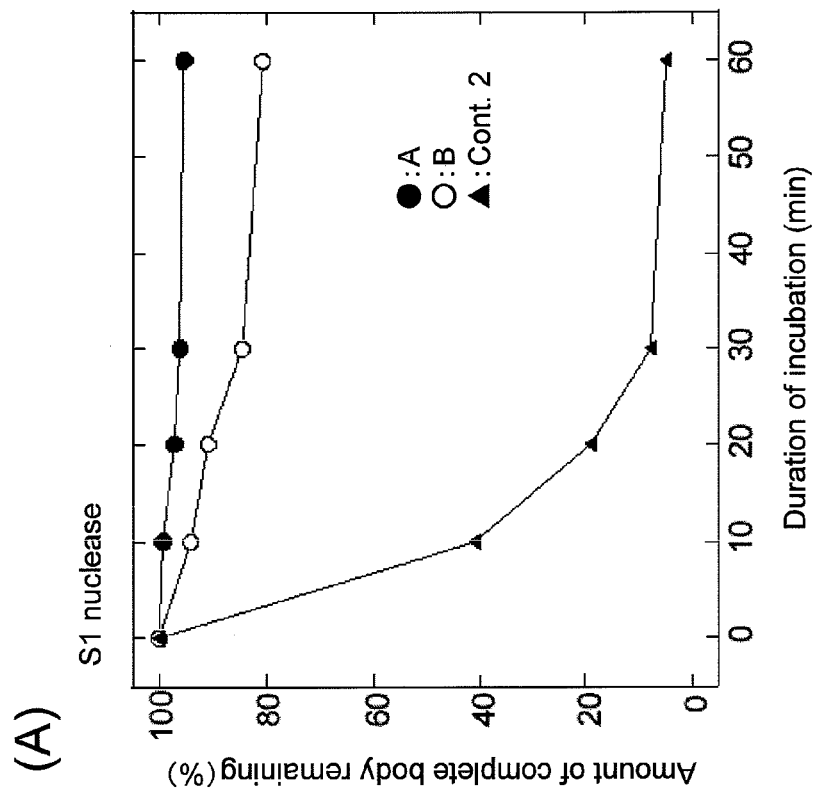

Fig. 25

|  |  | SEQ ID NO: |
|---|---|---|
| Cont. IV | GGACCACCGCAUCUCUACAtt | 47 |
|  | ttCCUGGUGGCGUAGAGAUGU | 48 |
|  |  |  |
| Cont. V | GGACCACCGCAUCUCUACAUUCAAG | 49 |
|  | CCUGGUGGCGUAGAGAUGUAAGUUC | 50 |

```
            3'↓5'
       a a g c g GGACCACCGCAUCUCUACAUUCAAG c g c g
  p                                                   a    51
       g c g c CCUGGUGGCGUAGAGAUGUAAGUUC g c g a        52
                                         5'↑3'
```

Fig. 28

|  |  | SEQ ID NO: |
|---|---|---|
| Cont. VI | GGUGGUGACGAUCUGGGCUtt<br>ttCCACCACUGCUAGACCCGA | 53<br>54 |
| Cont. VII | GCAGGUGGUGACGAUCUGGGCUGCA<br>CGUCCACCACUGCUAGACCCGACGU | 55<br>56 | q
```
                3'↓5'
       a  a g c g GGUGGUGACGAUCUGGGCU c g c  g
                                              a     57
       g  c g c  CCACCACUGCUAGACCCGA g c g  a       58
                                         5'↑3'
``` r
```
                3'↓5'
       a  a g c g GCAGGUGGUGACGAUCUGGGCUGCA c g c  g
                                                    a   59
       g  c g c  CGUCCACCACUGCUAGACCCGACGU g c g  a     60
                                              5'↑3'
```

STABILIZATION METHOD OF FUNCTIONAL NUCLEIC ACID

CROSS REFERENCE TO RELATED APPLICATIONS

This application is a Divisional of copending application Ser. No. 13/107,175, filed on May 13, 2011, which claims priority under 35 U.S.C. § 119(e) to U.S. Provisional Application No. 61/334,696, filed on May 14, 2010, all of which are hereby expressly incorporated by reference into the present application.

TECHNICAL FIELD

The present invention relates to a method for enhancing the resistance of a nucleic acid fragment to degradation by a nucleolytic enzyme and a nucleic acid having such properties.

BACKGROUND ART

Functional nucleic acids, such as siRNAs, nucleic acid aptamers, and decoy nucleic acids, have drawn attention as pharmaceuticals or diagnostic agents in recent years, and research on and development of a variety of nucleic acid pharmaceuticals and the like are in progress with the goal of establishing medical applications for the same all over the world.

However, nucleic acids are generally problematic in that they are likely to be degraded by nucleolytic enzymes, such as nucleases, in vivo. In particular, siRNAs or RNA aptamers that have recently drawn attention as nucleic acid pharmaceuticals because of the applicability and effects thereof are composed of RNAs, which are very unstable in vivo. Accordingly, in vivo stability of nucleic acid is essential for the efficient and continuous exertion of the pharmacological effects of nucleic acid pharmaceuticals.

Many methods aimed at nucleic acid stabilization and stabilized nucleic acids have heretofore been reported. An example is a method for stabilization of decoy nucleic acids using a dumbbell shape (WO 2003/091432, WO 2005/014810, and US 2003/040613). Formation of a dumbbell-shaped nucleic acid is a method in which both ends of a double-stranded nucleic acid fragment are ligated to each other with a loop structure, such as a linker nucleic acid, to form a closed circle, so that the double-stranded nucleic acid fragment acquires resistance to degradation by a nucleolytic enzyme. This method, however, disadvantageously necessitates a process of cyclization of a linear nucleic acid fragment.

Use of artificially constructed nucleic acid analogues that are not be degraded by nucleases is also taken into consideration. However, the application of nucleic acid analogues that are not degraded in vivo for pharmaceutical products remains problematic from the viewpoint of safety, such as with regard to side effects.

Accordingly, development of nucleic acid pharmaceuticals that are composed to as a great extent as possible of naturally occurring nucleic acids, resistant to degradation by nucleolytic enzymes, stably maintained in vivo, and easily prepared in a simple and cost-effective manner has been awaited. To this end, a method that allows easy stabilization of a variety of nucleic acid fragments in a cost-effective manner is necessary.

Object to be Attained by the Invention

It is an object of the present invention to provide a method for easily enhancing the resistance of a double-stranded nucleic acid fragment or a single-stranded nucleic acid fragment forming a higher-order structure via intramolecular annealing to degradation by a nucleolytic enzyme in a cost-effective manner and a nucleic acid obtained by such method.

The present invention provides a nucleic acid capable of enhancing the stability of a functional nucleic acid in vivo and allowing the same to continuously exert its pharmacological effects.

Means for Attaining the Object

The present inventors have conducted concentrated studies in order to attain the above object. As a result, they discovered that ligation of hairpin-shaped DNA comprising a specific sequence to the 5' end and/or the 3' end of a nucleic acid fragment comprising a single- or double-stranded functional nucleic acid may enhance resistance of the nucleic acid fragment to degradation by a nucleolytic enzyme, even if the fragment is not in a closed circular form.

The above-mentioned "hairpin-shaped DNA comprising a specific sequence" is a nucleic acid referred to as a "mini-hairpin" comprising 7 to 14 bases and forming a hairpin structure via intramolecular annealing, and it was discovered by the present inventors in the past (Hirao I. et al., 1990, Nucleic Acid Symp. Ser., 22, 75-76; Hirao I. et al., 1993, FEBS Lett., 321, 169-172; Khan I. M. & Coulson J. M., 1993, Nucleic Acids Res., 21, 2967-2958; Yoshizawa S. et al., 1994, Nucleic Acids Res. 22, 2217-2221; Hirao I. et al., 1994, Nucleic Acids Res. 22, 576-582; Mestre B. et al., 1995, Bioconjug. Chem., 6, 466-472; Yoshizawa S. et al., 1997, Biochemistry 36, 4761-4767; Jolles B. et al., 1997, Nucleic Acids Res. 25, 4608-4613). It has heretofore been known that a mini-hairpin is ligated to a single-stranded nucleic acid fragment, such as mRNA or primer DNA, which would not form a higher-order structure via intramolecular annealing, so that the mini-hairpin would be capable of imparting the single-stranded nucleic acid fragment with resistance to degradation by a nucleolytic enzyme. When the mini-hairpin was ligated to a double-stranded nucleic acid fragment or a single-stranded nucleic acid fragment forming a higher-order structure via intramolecular annealing that contains functional nucleic acids, it was not known that similar effects could be attained or functions of functional nucleic acids could be maintained. In addition, a dumbbell-shaped structure for nucleic acid stabilization is a closed circular structure as described above, and it has not been even deduced in the art that a dumbbell-like structure having a non-ligated region (i.e., a dumbbell-shaped structure having 1 or 2 nicks) has resistance to degradation by a nucleolytic enzyme.

The present invention has been completed based on such finding and provides (1) to (29) below.

(1) A nucleic acid comprising: hairpin-shaped DNA comprising nucleic acid regions (A) to (C) below sequentially ligated from the 5' end toward the 3' end: (A) a first nucleic acid region comprising 2 to 5 arbitrary nucleotides; (B) a second nucleic acid region comprising a "gna" or "gnna" base sequence, wherein each "n" independently represents "g", "t", "a", or "c", a base analogue, or a modified base; and (C) a third nucleic acid region comprising a base sequence complementary to the first nucleic acid region, wherein the first nucleic acid region and the third nucleic acid region form a stem portion by base pairing with each other and the second nucleic acid region forms a loop portion, and a double-stranded nucleic acid fragment made by complete or partial base pairing or a single-stranded nucleic acid fragment having at least one stem structure and at least one loop structure, wherein at least one end of the nucleic acid fragment is liagated to the hairpin-shaped DNA.

(2) The nucleic acid according to (1), wherein the first nucleic acid region comprises "g" or "c" base.

(3) The nucleic acid according to (1) or (2), wherein the nucleic acid fragment is composed of DNA, RNA, and/or a derivative thereof.

(4) The nucleic acid according to (3), wherein, when the nucleic acid fragment is the double-stranded nucleic acid fragment according to (1), the double-stranded nucleic acid fragment comprises siRNA base sequence.

(5) The nucleic acid according to (4) comprising any of (I) to (IV) below in which nucleic acid fragments and hairpin-shaped DNAs are sequentially ligated from the 5' end toward the 3' end:

(I) a nucleic acid fragment comprising the base sequence of an siRNA sense strand, the hairpin-shaped DNA defined in (1) above, a nucleic acid fragment comprising the base sequence of an siRNA antisense strand, and the hairpin-shaped DNA defined in (1) above;

(II) the hairpin-shaped DNA defined in (1) above, a nucleic acid fragment comprising the base sequence of an siRNA sense strand, the hairpin-shaped DNA defined in (1) above, and a nucleic acid fragment comprising the base sequence of an siRNA antisense strand;

(III) a nucleic acid fragment comprising the base sequence of an siRNA antisense strand, the hairpin-shaped DNA defined in (1) above, a nucleic acid fragment comprising the base sequence of an siRNA sense strand, and the hairpin-shaped DNA defined in (1) above; or (IV) the hairpin-shaped DNA defined in (1) above, a nucleic acid fragment comprising the base sequence of an siRNA antisense strand, the hairpin-shaped DNA defined in (1) above, and a nucleic acid fragment comprising the base sequence of an siRNA sense strand.

(6) The nucleic acid according to (4), wherein the hairpin-shaped DNA defined in (1) above is ligated to the ends according to any of (I) to (IV) below:

(I) the 5' end and the 3' end of a nucleic acid fragment comprising the base sequence of an siRNA sense strand; (II) the 5' end and the 3' end of a nucleic acid fragment comprising the base sequence of an siRNA antisense strand; (III) the 3' end of a nucleic acid fragment comprising the base sequence of an siRNA sense strand and the 3' end of a nucleic acid fragment comprising the base sequence of an siRNA antisense; and (IV) the 5' end of a nucleic acid fragment comprising the base sequence of an siRNA sense strand and the 5' end of a nucleic acid fragment comprising the base sequence of an siRNA antisense strand.

(7) The nucleic acid according to (4), wherein the hairpin-shaped DNA defined in (1) above is ligated to the end according to any of (I) to (IV) below:

(I) the 5' end of a nucleic acid fragment comprising the base sequence of an siRNA sense strand; (II) the 5' end of a nucleic acid fragment comprising the base sequence of an siRNA antisense strand; (III) the 3' end of a nucleic acid fragment comprising the base sequence of an siRNA sense strand; and (IV) the 3' end of a nucleic acid fragment comprising the base sequence of an siRNA antisense strand.

(8) The nucleic acid according to any of (4) to (7), wherein each strand of the double-stranded nucleic acid fragment comprises 19 to 30 bases.

(9) The nucleic acid according to any of (4) to (8), wherein the double-stranded nucleic acid fragment has at least one mismatched region and/or bulge structure.

(10) The nucleic acid according to (3), wherein, when the nucleic acid fragment is the double-stranded nucleic acid fragment according to (1), the double-stranded nucleic acid fragment comprises a target molecule-binding region.

(11) The nucleic acid according to (10), wherein nucleic acid fragments and hairpin-shaped DNAs are sequentially ligated from the 5' end toward the 3' end in (I) or (II) below:

(I) a nucleic acid fragment constituting the double-stranded nucleic acid fragment, the hairpin-shaped DNA defined in (1) above, the other nucleic acid fragment constituting the double-stranded nucleic acid fragment, and the hairpin-shaped DNA defined in (1) above; or (II) the hairpin-shaped DNA defined in (1) above, a nucleic acid fragment constituting the double-stranded nucleic acid fragment, the hairpin-shaped DNA defined in (1) above, and the other nucleic acid fragment constituting the double-stranded nucleic acid fragment.

(12) The nucleic acid according to (10), wherein the nucleic acid fragments and hairpin-shaped DNAs below are sequentially ligated from the 5' end toward the 3' end and both ends are ligated to each other:

a nucleic acid fragment constituting the double-stranded nucleic acid fragment, the hairpin-shaped DNA defined in (1) above, the other nucleic acid fragment constituting the double-stranded nucleic acid fragment, and the hairpin-shaped DNA defined in (1) above.

(13) The nucleic acid according to (12), which has a nick in a nucleic acid fragment region constituting the double-stranded nucleic acid fragment.

(14) The nucleic acid according to (12), wherein each of the nucleic acid fragment regions constituting the double-stranded nucleic acid fragment contains a nick, and the nick is not paired with the other nick.

(15) The nucleic acid according to (10), wherein the hairpin-shaped DNA defined in (1) above is ligated to the 5' end and the 3' end of any one of the nucleic acid fragment constituting a double-stranded nucleic acid fragment or the 5' or 3' end of each of the nucleic acid fragment constituting a double-stranded nucleic acid fragment.

(16) The nucleic acid according to any of (10) to (15), wherein the target molecule is a transcription regulator.

(17) The nucleic acid according to (3), wherein, when the nucleic acid fragment is the single-stranded nucleic acid fragment according to (1), the single-stranded nucleic acid fragment comprises a base sequence of a functional nucleic acid.

(18) The nucleic acid according to (17), wherein at least one stem structure formed via intramolecular annealing of the single-stranded nucleic acid fragment has a mismatched region or bulge structure.

(19) The nucleic acid according to (17), wherein the functional nucleic acid is selected from the group consisting of a single-stranded miRNA precursor, shRNA, a nucleic acid aptamer, a ribozyme (including deoxyribozyme), a molecular beacon or riboswitch, and a U1 adaptor.

(20) The nucleic acid according to any of (17) to (19), wherein the hairpin-shaped DNA defined in (1) above is ligated to either the 5' or 3' end of the single-stranded nucleic acid fragment.

(21) A pharmaceutical composition comprising, as an active ingredient, the nucleic acid according to any of (1) to (20).

(22) The pharmaceutical composition according to (21), which comprises a pharmaceutically acceptable carrier.

(23) A method for enhancing resistance of a nucleic acid fragment to degradation by a nucleolytic enzyme by ligating hairpin-shaped DNA comprising the nucleic acid regions (A) to (C) below sequentially ligated from the 5' end toward the 3' end: (A) a first nucleic acid region comprising 2 to 5 arbitrary nucleotides; (B) a second nucleic acid region comprising a "gna" or "gnna" base sequence, wherein each "n" independently represents "g", "t", "a", or "c", a base analogue, or a modified base; and (C) a third nucleic acid region comprising a base sequence complementary to the first nucleic acid region, wherein the first nucleic acid region and the third nucleic acid region form a setm portion by base pairing with each other and the second nucleic acid region forms a loop portion, to at least one end of the nucleic acid fragment (I) or (II) below:

(I) a double-stranded nucleic acid fragment made by the complete or partial base pairing; or (II) a single-stranded nucleic acid fragment having at least one stem structure and at least one loop structure.

(24) The method according to (23), wherein the first nucleic acid region comprises "g" or "c" base.

(25) The method according to (23) or (24), wherein the nucleic acid fragment is composed of DNA, RNA, and/or a derivative thereof.

(26) The method according to (25), wherein, when the nucleic acid fragment is the double-stranded nucleic acid fragment according to (23) (I), the double-stranded nucleic acid fragment comprises the siRNA base sequence.

(27) The method according to (25), wherein, when the nucleic acid fragment is the double-stranded nucleic acid fragment according to (23) (I), the double-stranded nucleic acid fragment comprises a target molecule-binding region.

(28) The method according to (25), wherein, when the nucleic acid fragment is the single-stranded nucleic acid fragment according to (23) (II), the single-stranded nucleic acid fragment comprises a functional nucleic acid.

(29) The method according to (28), wherein the functional nucleic acid is selected from the group consisting of shRNA, pri-miRNA, pre-miRNA, a nucleic acid aptamer, a ribozyme (including deoxyribozyme), a molecular beacon or riboswitch, and a U1 adaptor.

This description includes part or all of the contents as disclosed in the description and/or drawings of U.S. Patent Application No. 61/334,696, which is a provisional application of the present application.

Effects of the Invention

Use of the nucleic acid of the present invention can impart resistance to degradation by a nucleolytic enzyme and high in vivo stability to a double-stranded nucleic acid fragment or a single-stranded nucleic acid fragment forming a higher-order structure via intramolecular annealing in a simple and cost-effective manner. Thus, in vivo stability of functional nucleic acids contained in the double-stranded nucleic acid fragment or single-stranded nucleic acid fragment can be enhanced, and pharmacological effects thereof can be continuously exerted for a long period of time.

BRIEF DESCRIPTION OF THE DRAWINGS

FIG. 1 is a conceptual diagram showing the nucleic acid of the present invention; wherein (A) shows an example of a nucleic acid comprising two hairpin-shaped DNAs (101) and a double-stranded nucleic acid fragment (102) composed of strands of the same base length; (B) shows an example of a nucleic acid comprising one hairpin-shaped DNA (101) and a double-stranded nucleic acid fragment (103) composed of two strands of different base lengths; and (C) shows an example of a nucleic acid comprising one hairpin-shaped DNA (101) and a single-stranded nucleic acid fragment (108).

FIG. 3 is a conceptual diagram showing an embodiment of the nucleic acid of the present invention comprising a hairpin-shaped DNA (301) ligated to a double-stranded nucleic acid fragment (302).

FIG. 4 is a conceptual diagram showing an embodiment of the nucleic acid of the present invention comprising a hairpin-shaped DNA (401) ligated to a double-stranded nucleic acid fragment (402), when the double-stranded nucleic acid fragment comprises the siRNA base sequence. In the double-stranded nucleic acid fragment (402), the S side is a nucleic acid fragment comprising the base sequence of an siRNA sense strand, and the A side is a nucleic acid fragment comprising the base sequence of an siRNA antisense strand.

FIG. 5 is a conceptual diagram showing an embodiment of the nucleic acid of the present invention comprising two hairpin-shaped DNAs (501) ligated to a double-stranded nucleic acid fragment (502), when the nucleic acid comprises a non-ligated region.

FIG. 6 is a conceptual diagram showing an embodiment of the nucleic acid of the present invention comprising two hairpin-shaped DNAs (601) ligated to a double-stranded nucleic acid fragment (602), when the nucleic acid comprises a non-ligated region and the double-stranded nucleic acid fragment comprises the siRNA base sequence. In the double-stranded nucleic acid fragment (602), the S side is a nucleic acid fragment comprising the base sequence of an siRNA sense strand, and the A side is a nucleic acid fragment comprising the base sequence of an siRNA antisense strand.

FIG. 7 is a conceptual diagram showing an embodiment of the nucleic acid of the present invention comprising two hairpin-shaped DNAs (701) ligated to a double-stranded nucleic acid fragment (702), when the nucleic acid comprises two non-ligated regions.

FIG. 8 is a conceptual diagram showing an embodiment of the nucleic acid of the present invention comprising two hairpin-shaped DNAs (801) ligated to a double-stranded nucleic acid fragment (802), when the nucleic acid comprises two non-ligated regions and the double-stranded nucleic acid fragment comprises the siRNA base sequence. In the double-stranded nucleic acid fragment (802), the S side is a nucleic acid fragment comprising the base sequence of an siRNA sense strand, and the A side is a nucleic acid fragment comprising the base sequence of an siRNA antisense strand.

FIG. 9 is a conceptual diagram showing an embodiment of the nucleic acid of the present invention, showing the number of nicks in a double-stranded nucleic acid fragment (902) and positions thereof, wherein all the ends of two hairpin-shaped DNAs (901) ligated to all the ends of the double-stranded nucleic acid fragment (902).

FIG. 12 shows various nucleic acid sequences and structures containing siRNA targeting firefly luciferase mRNA prepared in Example 1. An arrow indicates a non-ligated region (a nick region). DNAs sequences are represented by lower-case letters and RNA sequences are represented by upper-case letters. An underlined sequence represents an siRNA antisense strand (a guide strand).

FIG. 18 shows sequences and structures of various nucleic acids containing decoy DNAs prepared in Example 6, which recognize NF-kB as a target molecule. An arrow indicates a non-ligated region (a nick region). An underlined sequence represents a consensus sequence binding to NF-κB. A base region indicated in boldface represents the hairpin-shaped DNA described in the present invention.

FIG. 21 shows changes of various nucleic acids containing decoy DNAs, caused with S1 nuclease (A) or with human serum (B) with the elapse of time.

FIG. 25 shows sequences and structures of siRNA targeting the survivin gene, which is an endogenous gene in the HeLa cell, and the nucleic acid p of the present invention containing the same. An arrow indicates a non-ligated region (a nick region) in the nucleic acid p. In the sequences, DNAs are represented by lower-case letters and RNAs are represented by upper-case letters. An underlined sequence represents an siRNA antisense strand (a guide strand).

FIG. 28 shows sequences and structures of siRNA targeting the Lamin A/C gene (Cont. VI and Cont. VII), which is endogenous gene in the HeLa cell, and the nucleic acids q and r of the present invention containing the same. An arrow indicates a non-ligated region (a nick region) in the nucleic acids q and r. In the sequences, DNAs are represented by lower-case letters and RNAs are represented by upper-case letters. An underlined sequence represents an siRNA antisense strand (a guide strand).

PREFERRED EMBODIMENTS OF THE INVENTION

I. Nucleic Acid

Figure 2:
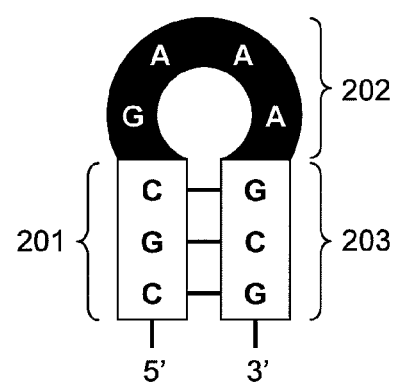
FIG. 2 is a conceptual diagram showing hairpin-shaped DNA constituting the nucleic acid of the present invention. Hairpin-shaped DNA comprises a first nucleic acid region (201), a second nucleic acid region (202), and a third nucleic acid region (203), and nucleotides constituting the first nucleic acid region (201) are base-paired with nucleotides constituting the third nucleic acid region (203) to form a stem structure.

The first aspect of the present invention relates to a nucleic acid having resistance to degradation by a nucleolytic enzyme. FIG. 1 is a diagram showing examples of structures of the nucleic acid of the present invention. As shown in (A) to (C) of FIG. 1, the nucleic acid of the present invention comprises hairpin-shaped DNA (101) and nucleic acid fragments (102, 103, and 108), wherein hairpin-shaped DNA is ligated to at least one end of the nucleic acid fragments.

In principle, the term "nucleic acid" used herein refers to a biopolymer comprising, as constitutional units, nucleotides ligated to each other via phosphodiester bond. In general, accordingly, the term refers to a naturally occurring nucleic acid to which a naturally occurring nucleotide existing in nature is ligated, such as DNA comprising deoxyribonucleotides having any of adenine, guanine, cytosine, and thymine ligated to each other and/or RNA comprising ribonucleotides having any of adenine, guanine, cytosine, and uracil ligated to each other. In addition, non-naturally occurring nucleotides and non-naturally occurring nucleic acids may be within the scope of the nucleic acid of the present invention.

The term "non-naturally occurring nucleotide" used herein refers to an artificially constructed or artificially chemically-modified nucleotide, which does not exist in nature, having properties and/or structures similar to those of a naturally occurring nucleotide or comprising nucleosides or bases having properties and/or structures similar to those of nucleosides or bases constituting a naturally occurring nucleotide.

Examples thereof include abasic nucleoside, arabinonucleoside, 2'-deoxyuridine, α-deoxyribonucleoside, β-L-deoxyribonucleoside, and other nucleosides with sugar modifications. Further, examples of nucleosides with sugar modifications include substituted pentoses (e.g., 2'-O-methyl ribose, 2'-deoxy-2'-fluororibose, 3'-O-methyl ribose, and 1',2'-deoxyribose), arabinose, substituted arabinose sugar, substituted hexose, and nucleosides of alpha anomers with sugar modifications. The non-naturally occurring nucleotide of the present invention may be an artificially constructed base analogue or an artificially chemically-modified base (i.e., modified base). Examples of "base analogues" include 2-oxo-(1H)-pyridin-3-yl, 5-substituted-2-oxo-(1H)-pyridin-3-yl, 2-amino-6-(2-thiazolyl)purin-9-yl, 2-amino-6-(2-thiazolyl)purin-9-yl, and 2-amino-6-(2-oxazolyl)purin-9-yl. Examples of "modified bases" include modified pyrimidines (e.g., 5-hydroxycytosine, 5-fluorouracil, and 4-thiouracil), modified purines (e.g., 6-methyladenine and 6-thioguanosine), and other heterocyclic bases.

The term "non-naturally occurring nucleic acid" used herein refers to an artificially constructed nucleic acid analogue having a structure and/or properties similar to those of a naturally occurring nucleic acid. Examples thereof include peptide nucleic acids (PNA), peptide nucleic acids with phosphate groups (PHONA), bridged nucleic acids/locked nucleic acids (BNA/LNA), and morpholino nucleic acids. Further examples include chemically-modified nucleic acids and nucleic acid analogues, such as methylphosphonate DNA/RNA, phosphorothioate DNA/RNA, phosphoramidate DNA/RNA, and 2'-O-methyl DNA/RNA.

A phosphoric acid group, a sugar, and/or a base in the nucleic acid of the present invention may be labeled as necessary. Any substances for nucleic acid labeling known in the art can be used for labeling. Examples thereof include radioactive isotopes (e.g., $^{32}P$, $^{3}H$, and $^{14}C$), DIG, biotin, fluorescent dyes (e.g., FITC, Texas, cy3, cy5, cy7, FAM, HEX, VIC, JOE, Rox, TET, Bodipy493, NBD, and TAMRA), and luminescent substances (e.g., acridinium ester).

Hereinafter, non-naturally occurring nucleotides, non-naturally occurring nucleic acids, and labeled nucleic acids are collectively referred to as "modified nucleic acids" for convenience.

1. Constitution of the Nucleic Acid of the Present Invention

As described above, the nucleic acid of the present invention is composed of hairpin-shaped DNA (101) and nucleic acid fragments (i.e., a double-stranded nucleic acid fragment 102 or 103, or a single-stranded nucleic acid fragment 108). Hereafter, these constituents are described in detail.

1-1. Hairpin-Shaped DNA

FIG. 2 schematically shows hairpin-shaped DNA constituting the nucleic acid of the present invention. As shown in FIG. 2, hairpin-shaped DNA comprises three DNA nucleic acid regions: the first nucleic acid region (201); the second nucleic acid region (202); and the third nucleic acid region (203), sequentially ligated from the 5' end toward the 3' end.

The "first nucleic acid region" comprises 2 to 5 arbitrary nucleotides. The term "nucleotide" refers to a "deoxyribonucleotide" having guanine (g), adenine (a), cytosine (c), or thymine (t). A nucleotide in such nucleic acid region is preferably guanine or cytosine for the following reason: when the first nucleic acid region forms a stem structure with the third nucleic acid region, a larger "gc" content results in the increased Tm value, and the stem structure can then be stably maintained. Accordingly, it is most preferable that the entire base sequence of the first nucleic acid region be composed of "g" and/or "c".

The "second nucleic acid region" comprises the 5'-gna-3' or 5'-gnna-3' base sequence. Each "n" in the sequence is independently composed of any naturally occurring base (g, a, t, or c), the base analogue, or the modified base.

The "third nucleic acid region" has a base sequence complementary to the first nucleic acid region. Accordingly, the base sequence of the third nucleic acid region is determined based on the base sequence of the first nucleic acid region, and the first nucleic acid region and the third nucleic acid region form base-pairing with each other in the molecule. As a result, the first nucleic acid region and the third nucleic acid region constitute a stem portion in which all bases are paired with each other. The second nucleic acid region located between the first nucleic acid region and the third nucleic acid region forms loop portion therewith. For example, hairpin-shaped DNA comprising 7 to 14 nucleotides having the base sequence as shown in SEQ ID NO: 1 or 2 is formed as a whole.

Such hairpin-shaped DNA may be ligated to at least one end of the nucleic acid fragment described below via phosphodiester linkage. Thus, resistance of the nucleic acid fragment to degradation by the nucleolytic enzyme can be enhanced, and stability thereof can be enhanced in vivo.

1-2. Nucleic Acid Fragment

A nucleic acid fragment constituting the nucleic acid of the present invention is a double-stranded nucleic acid fragment or a single-stranded nucleic acid fragment forming a higher-order structure via intramolecular annealing. Such nucleic acid fragment can include a base sequence of a functional nucleic acid. The term "functional nucleic acid" used herein refers to a nucleic acid having specific biological functions in vivo or in cells, such as enzymatic functions, catalytic functions, or biologically inhibiting or enhancing functions (e.g., inhibition or enhancement of transcription or translation). Specific examples include siRNA, shRNA, miRNA (including pri-miRNA and pre-miRNA), nucleic acid aptamers (including RNA aptamers and DNA aptamers), ribozymes (including deoxyribozymes), riboswitches, U1 adaptors, molecular beacons, and transcriptional factor-binding regions.

Hereafter, the double-stranded nucleic acid fragment and the single-stranded nucleic acid fragment are described in detail.

1-2-1. Double-Stranded Nucleic Acid Fragment

Bases in nucleic acid fragments constituting a double-stranded nucleic acid fragment are completely or partially base-paired in the nucleic acid of the present invention. The term "completely" used herein refers to a condition in which all bases of at least one nucleic acid fragment are base-paired with corresponding bases of another nucleic acid fragment. When the base lengths of the nucleic acid fragments are equivalent, accordingly, all the bases of the two nucleic acid fragments are base-paired. The term "partially" used herein refers to a condition in which some, and preferable at least two continuous bases in the relevant base sequences of nucleic acid fragments are base-paired. In such a case, accordingly, the double-stranded nucleic acid fragment may comprise a mismatched region (104) of one or more bases or one or more bulge structures (105), as shown in FIG. 1 (B).

The double-stranded nucleic acid fragment of the present invention comprises 3 or more, preferably 5 or more, more preferably 7 or more, and further preferably 10 or more base pairs as a whole. The base length of the double-stranded nucleic acid fragment of the present invention is not particularly limited. Such length may be adequately determined, so that each functional nucleic acid region can exert its functions. Base lengths of nucleic acid fragments constituting a double-stranded nucleic acid fragment may be the same or different. The same base length is preferable. When base lengths of nucleic acid fragments are different from each other, a longer strand may form one or more loop structures and one or more stem structures (107) via intramolecular annealing, as shown in FIG. 1 (B). In such a case, a stem structure can contain one or more mismatched regions (104) or one or more bulge structures (105).

The double-stranded nucleic acid fragment is composed of DNA, RNA and/or a modified nucleic acid.

As described above, the double-stranded nucleic acid fragment can contain a base sequence of a functional nucleic acid. Examples of functional nucleic acids that can be contained in the double-stranded nucleic acid fragment include siRNA, mature double-stranded miRNA, and a functional nucleic acid fragment having a target molecule-binding region. These members are described below.

<siRNA>

Small interference RNA (siRNA) is small-molecular double-stranded RNA comprising a sense strand having a base sequence corresponding to a part of a target gene and an antisense strand thereof. siRNA can induce sequence-specific post-transcriptional gene silencing (i.e., RNA interference) by introducing it into cells (eukaryotic cells) (Fire A. et al., 1998, Nature, 391, 806-811). Hereafter, a case in which a siRNA base sequence is contained in a double-stranded nucleic acid fragment constituting the nucleic acid of the present invention is described.

siRNA contained in the double-stranded nucleic acid fragment includes a base sequence that completely matches with a continuous partial region of the base sequence of a sense strand of a target gene in either nucleic acid fragment. The length of the completely matched base sequence is 17 to 32 bases, preferably 18 to 30 bases, and more preferably 19 to 25 bases.

A nucleic acid region corresponding to siRNA in the double-stranded nucleic acid fragment is composed of RNA in principle. Such region can contain one or several modified nucleic acids. The term "several" used herein refers to an integer between 2 and 30, such as integers between 2 and 30, 2 and 29, 2 and 28, 2 and 27, 2 and 26, 2 and 25, 2 and 24, 2 and 23, 2 and 22, 2 and 21, 2 and 20, 2 and 19, 2 and 18, 2 and 17, 2 and 16, 2 and 15, 2 and 14, 2 and 13, 2 and 12, 2 and 11, 2 and 10, 2 and 9, 2 and 8, 2 and 7, 2 and 6, 2 and 5, 2 and 4, and 2 and 3.

In the base sequence of the double-stranded nucleic acid fragment, at least one nucleotide (DNA and/or RNA) or nucleic acid analogue may be present at one or both ends of siRNA. The number of nucleotides or the like at one or both ends of siRNA is not particularly limited. If such end is ligated to the hairpin-shaped DNA, the number is preferably between 1 and 20. Specifically, thymine-thymine (TT) or uracil-uracil (UU) can be added to the 3' end of the siRNA sense strand and that of the RNA antisense strand, for example.

The target gene of siRNA is not particularly limited. Accordingly, the nucleic acid of the present invention can include an siRNA base sequence corresponding to any target gene, in principle.

siRNA may be designed in accordance with a conventional technique based on a target gene base sequence. For example, the sequence can be designed based on the method of Ui-Tei et al. (Nucleic Acids Res., 32: 936-948, 2004), the method of Reynolds et al. (Nat. Biotechnol., 22: 326-330, 2004), or the method of Amarzguioui et al. (Biochem. Biophys. Res. Commun., 316: 1050-1058, 2004). In addition, web sites on which siRNA can be designed have been made available to public by a variety of research institutes or companies, and effective siRNA can be designed on the web. Representative examples of siRNA designing web sites include siDirect (design.RNAi.jp/), siSearch (www.epigeneticstation.com/epigenetic-links/detail/link-203.html), the siDESIGN Center (www.dharmacon.com/designcenter/designcenterpage.aspx), the siRNA Selection Server (jura.wi.mit.edu/bioc/siRNAext/), and the Gene Specific siRNA Selector (bioinfo.wistar.upenn.edu/siRNA/siRNA.htm).

The nucleic acid of the present invention comprising, as a constitutive element, a double-stranded nucleic acid fragment including such siRNA base sequence is capable of silencing the target gene expression in vivo or in cells with greater stability than conventional siRNA.

Also, the double-stranded nucleic acid fragment can include other functional nucleic acids, in addition to siRNA. When a nucleic acid fragment of the double-stranded nucleic acid fragment contains a long region that is not base-paired with the other nucleic acid fragment and one or more loop structures and one or more stem structures are consequently formed therein via intramolecular annealing (i.e., the case as shown in FIG. 1 (B) 107), for example, the double-stranded nucleic acid fragment may contain siRNA in a region in which a nucleic acid fragment is base-paired (106), and the double-stranded nucleic acid fragment may further contain other functional nucleic acids, such as RNA aptamers or single-stranded miRNA precursors, in a region in which a secondary structure is formed via intramolecular annealing (107).

<Mature Double-Stranded miRNA> miRNA (micro RNA) is single-stranded non-coding RNA that is 21 to 23 bases in length, is present in vivo, and regulates the expression of a given gene. Such RNA is known to form a complex by binding to mRNA of a target gene and a protein factor and to inhibit the translation of the target gene. miRNA is transcribed from the genome as a single-stranded precursor referred to as pri-miRNA, further processed into a single-stranded precursor referred to as pre-miRNA with the use of an endonuclease referred to as Drosha in the nucleus, and converted into mature double-stranded miRNA by the action of an endonuclease referred to as Dicer outside the nucleus. One strand thereof is incorporated into an RISC (RNA-induced silencing complex) and it regulates the expression of the target gene as a mature single-stranded miRNA. A double-stranded nucleic acid fragment of the nucleic acid of the present invention can include a base sequence of such mature double-stranded miRNA.

Mature double-stranded miRNA of a double-stranded nucleic acid fragment preferably has a base sequence identical to that of wild-type mature double-stranded miRNA. In such a case, such sequence may be designed based on the base sequence of miRNA encoded in the genome.

At least one nucleotide (DNA and/or RNA) or a nucleic acid analogue may be present at one or both ends of mature double-stranded miRNA in a double-stranded nucleic acid fragment. The number of nucleotides or the like at one or both ends of mature double-stranded miRNA is not particularly limited. If such end is to be ligated to the aforementioned hairpin-shaped DNA, such number is preferably between 1 and 20.

The target gene of mature double-stranded miRNA is not particularly limited. With the use of the nucleic acid of the present invention, accordingly, miRNA of a gene of interest can be used when it is present in the genome.

<Functional Nucleic Acid Fragment Having Target Molecule-Binding Region>

The term "target molecule-binding region" refers to a region in a nucleic acid that can bind to a given target molecule with specificity and/or high affinity. A functional nucleic acid fragment having a target molecule-binding region (hereafter, referred to as a "functional nucleic acid fragment") binds to a target molecule in vivo or in a cell to inhibit or suppress biological functions of the target molecule. Examples of target molecules include protein factors specifically binding to DNA or RNA, nucleic acids, and low-molecular-weight compounds. An example of a functional nucleic acid fragment is a docoy DNA that has a DNA-binding region of a given transcription regulator and inhibits or suppresses functions of a transcription factor.

At least one nucleotide (DNA and/or RNA) or a modified nucleic acid may be present at one or both ends of a functional nucleic acid fragment in a base sequence of a double-stranded nucleic acid fragment. The number of nucleotides or the like at one or both ends is not particularly limited. If such end is to be ligated to the aforementioned hairpin-shaped DNA, such number is preferably between 1 and 20.

The target molecule of a functional nucleic acid fragment is not particularly limited. If a binding region of the target molecule of interest is known, the target molecule may be designed and constructed based thereon.

The nucleic acid of the present invention comprising, as a constitutional element, a double-stranded nucleic acid fragment including a base sequence of such functional nucleic acid fragment is capable of inhibiting or suppressing biological functions of a target molecule in vivo or in a cell with greater stability than existing functional nucleic acid fragments.

1-2-2. Single-Stranded Nucleic Acid Fragment

Each base of a single-stranded nucleic acid fragment constituting the nucleic acid of the present invention has at least one stem structure (109) and at least one loop structure (110) resulting from intramolecular annealing, as shown in FIG. 1 (*c*). Further, a stem structure may contain at least one mismatched region (111) and/or at least one bulge structure (112). A functional nucleic acid that can be contained in the single-stranded nucleic acid fragment forms a higher-order structure via intramolecular annealing and exerts its functions. Examples include a single-stranded miRNA precursor, shRNA, a nucleic acid aptamer, a ribozyme (including deoxyribozyme), a molecular beacon, a riboswitch, a U1 adaptor, and a functional nucleic acid fragment. A functional nucleic acid that does not generally form a higher-order structure via intramolecular annealing, such as a primer, probe, mature single-stranded miRNA, or antisense DNA, is not contained in the single-stranded nucleic acid fragment. Hereafter, a functional nucleic acid that can be contained in a single-stranded nucleic acid fragment is described.

<Single-Stranded miRNA Precursor>

As described in the "Mature double-stranded miRNA" section above, the term "single-stranded miRNA precursor" refers to miRNA in the state of a single-stranded precursor before it is converted into mature single-stranded miRNA upon transcription from the genome and processing in the nucleus. Specific examples include pri-miRNA and pre-miRNA.

A sequence of a single-stranded miRNA precursor within a single-stranded nucleic acid fragment can be the same base sequence as that of wild-type miRNA encoded in the genome.

At least one nucleotide (DNA and/or RNA) or a modified nucleic acid may be present at one or both ends of a single-stranded miRNA precursor in a single-stranded nucleic acid fragment. The number of nucleotides or the like at one or both ends of the single-stranded miRNA precursor is not particularly limited. If such end is to be ligated to the aforementioned hairpin-shaped DNA, such number is preferably between 1 and 20.

The target gene of a single-stranded miRNA precursor is not particularly limited. With the use of the nucleic acid of the present invention, accordingly, miRNA for a gene to be regulated the expression can be used when it is present in the genome.

The nucleic acid of the present invention comprising a single-stranded nucleic acid fragment including such single-stranded miRNA precursor may be used in an adequate manner, so that the expression of a target gene can be silenced specifically and with greater stability than is possible with existing miRNA.

<shRNA> shRNA (short hairpin RNA) is single-stranded RNA comprising siRNA or mature double-stranded miRNA ligated by an adequate short spacer sequence. Accordingly, a sense region is base-paired with an antisense region to form a stem structure in a molecule, and the spacer sequence forms a loop structure therein. Thereby, an shRNA molecule has a hairpin-shaped stem-loop structure as a whole. A spacer sequence generally comprises 3 to 24 bases and preferably 4 to 15 bases. A spacer sequence is not particularly limited, provided that siRNA or mature double-stranded miRNA is capable of base pairing.

At least one nucleotide (DNA and/or RNA) or a nucleic acid analogue may be present at one or both ends of shRNA of a base sequence in a single-stranded nucleic acid fragment. The number of nucleotides or the like at one or both ends of shRNA is not particularly limited. If such end is to be ligated to the aforementioned hairpin-shaped DNA, such number is preferably between 1 and 20.

The target gene of shRNA is not particularly limited, provided that it contains siRNA. In such a case, accordingly, the nucleic acid of the present invention can include shRNA for any target gene, in principle. When shRNA contains mature double-stranded miRNA, shRNA of a target gene of interest can be contained without particular limitation, provided that miRNA of a target gene is present in the genome.

<Nucleic Acid Aptamer>

The term "nucleic acid aptamer" refers to a nucleic acid that binds to a target molecule via its conformation, and thereby inhibits or suppresses functions of such molecule. RNA aptamers constituted by RNA and DNA aptamers constituted by DNA are known. A nucleic acid aptamer contained in the nucleic acid of the present invention may be constituted by DNA, RNA, or a combination thereof. An RNA aptamer constituted by RNA is preferable because RNA has flexibility that enables the formation of more conformations compared with DNA, in general.

A nucleic acid aptamer generally has higher specificity and affinity to a target molecule than an antibody. Accordingly, a nucleic acid aptamer can specifically, directly, and firmly bind to a target molecule. Since the number of target amino acid residues necessary for binding may be smaller than that of an antibody, for example, a nucleic acid aptamer is superior to an antibody, when selective suppression of functions of a given protein among highly homologous proteins is intended. Regarding aptamers, reference can be made to Jaynasena S. D., 1999, Clin. Chem. 45: 1628-1650, for example.

At least one nucleotide (DNA and/or RNA) or a nucleic acid analogue may be present at one or both ends of a nucleic acid aptamer in a base sequence of a single-stranded nucleic acid fragment. The number of nucleotides or the like at one or both ends of the nucleic acid aptamer is not particularly limited. If such an end is to be ligated to the aforementioned hairpin-shaped DNA, such number is preferably between 1 and 20.

The target molecule of the nucleic acid aptamer is not particularly limited. Accordingly, the nucleic acid of the present invention can contain a nucleic acid aptamer for any target molecule, in principle.

A nucleic acid aptamer sequence may be designed based on a base sequence of a nucleic acid aptamer obtained by a method known in the art or a known nucleic acid aptamer sequence. When a nucleic acid aptamer is to be prepared, an RNA aptamer is prepared via in vitro selection making use of the systematic evolution of ligands by exponential enrichment (SELEX) method, for example. The SELEX method comprises selecting an RNA molecule bound to a target molecule from an RNA pool composed of RNA molecules each having random sequence regions and primer-binding regions at both ends thereof, amplifying the recovered RNA molecule via RT-PCR, performing transcription using the obtained cDNA molecule as a template, and using the resultant as an RNA pool for the subsequent procedure.

Such procedure is repeated several times to several tens of times to select RNA with a stronger ability to bind to a target molecule. The base sequence lengths of the random sequence region and the primer binding region are not particularly limited. In general, the random sequence region comprises 20 to 80 bases and the primer binding region comprises 15 to 40 bases. Specificity to a target molecule may be enhanced by prospectively mixing molecules similar to the target molecule with RNA pools and using a pool comprising RNA molecules that did not bind to the molecule of interest. An RNA molecule that was obtained as a final product by such technique is used as an RNA aptamer. The SELEX method is a known technique, and a specific method may be implemented in accordance with, for example, Pan et al. (Proc. Natl. Acad. Sci. U.S.A., 1995, 92: 11509-11513).

The nucleic acid of the present invention comprising a single-stranded nucleic acid fragment that includes such nucleic acid aptamer may be used in accordance with an adequate method, so that functions of a target molecule can be inhibited or suppressed specifically and with greater stability than is possible with existing nucleic acid aptamers.

<Ribozyme>

The term "ribozyme" refers to RNA having catalytic functions of specifically cleaving a specific RNA site. The ribozyme of the present invention includes a deoxyribozyme composed of DNA, in addition to a ribozyme composed of RNA. Accordingly, the "ribozyme" of the present invention generally encompasses those constituted in the form of single-stranded RNA and/or DNA.

At least one nucleotide (DNA and/or RNA) or a nucleic acid analogue may be present at one or both ends of a ribozyme in the base sequence of a single-stranded nucleic acid fragment. The number of nucleotides or the like at one or both ends of the ribozyme is not particularly limited. If such end is to be ligated to the aforementioned hairpin-shaped DNA, such number is preferably between 1 and 20. The target molecule of the ribozyme is not particularly limited. Accordingly, the nucleic acid of the present invention can contain a ribozyme for any target molecule, in principle.

<Molecular Beacon>

A "molecular beacon" is a hairpin-shaped single-stranded nucleic acid having a stem structure and a loop structure, and it is a tool for genetic analysis used as a probe for confirming the existence of a sequence complementary to a loop portion. It is generally quenched because of the short distance between a fluorophore and a quencher. If a loop portion contains a complementary sequence, however, the loop portion hybridizes to the complementary sequence. This opens the hairpin structure, the fluorophore is separated from the quencher, and fluorescence is thus detected.

At least one nucleotide (DNA and/or RNA) or a nucleic acid analogue may be present at one or both ends of a molecular beacon in the base sequence of a single-stranded nucleic acid fragment. The number of nucleotides or the like at one or both ends of the molecular beacon is not particularly limited. If such end is to be ligated to the aforementioned hairpin-shaped DNA, such number is preferably between 1 and 20.

The target molecule of the molecular beacon is not particularly limited. Accordingly, the nucleic acid of the present invention can include a molecular beacon for any target molecule, in principle.

<Riboswitch>

A "riboswitch" is a cis-element existing in a non-translational region at the 5' end of mRNA, and it functions as a metabolite-sensitive gene switch. The riboswitch directly binds to a low-molecular-weight organic compound or the like to alter the mRNA conformation and regulates the gene expression.

At least one nucleotide (DNA and/or RNA) or a nucleic acid analogue may be present at one or both ends of the riboswitch in the base sequence of a single-stranded nucleic acid fragment. The number of nucleotides or the like at one or both ends of the riboswitch is not particularly limited. If such end is to be ligated to the aforementioned hairpin-shaped DNA, such number is preferably between 1 and 20.

The target molecule of the riboswitch is not particularly limited. Accordingly, the nucleic acid of the present invention can contain a riboswitch for any target molecules, in principle.

<U1 Adaptor>

A "U1 adaptor" is a bifunctional single-stranded nucleic acid comprising about 25 bases, and it comprises a 5'-"target domain" complementary to the 3'-terminal exon in the mRNA precursor of the target gene and a 3'-"U1 domain" having a sequence complementary to the 5' region of U1 snRNA (Goraczniak R. et al., 2009, Nat. Biotechnol., Vol. 27, pp. 257-263). Upon introduction of the U1 adaptor into an organism, U1 snRNP containing U1 snRNA binds to a region in the vicinity of a poly A signal of the mRNA precursor of the target gene, and polyadenylation of such mRNA is specifically inhibited. As a result, the mRNA precursor of the target gene is unstabilized and then degraded in the nucleus. Thus, gene silencing takes place.

At least one nucleotide (DNA and/or RNA) or a nucleic acid analogue may be present at one or both ends of the U1 adaptor in the base sequence of a single-stranded nucleic acid fragment. The number of nucleotides or the like at one or both ends of the U1 adaptor is not particularly limited. If such an end is to be ligated to the aforementioned hairpin-shaped DNA, such number is preferably between 1 and 20.

The target gene of the U1 adaptor is not particularly limited. Accordingly, the nucleic acid of the present invention can contain a U1 adaptor for any target gene, in principle.

The nucleic acid of the present invention containing a single-stranded nucleic acid fragment including such U1 adaptor may be used in an adequate manner, so that functions of a target molecule can be inhibited or suppressed specifically and with greater stability than is possible with existing nucleic acid aptamers.

<Functional Nucleic Acid Fragment Comprising Target Molecule-Binding Region>

The target molecule-binding region is as described in the "Functional nucleic acid fragment having a target molecule-binding region" section of "1-2-1. Double-stranded nucleic acid fragment" above. An example of a functional nucleic acid fragment is decoy RNA that has an RNA binding region of a given selective splicing regulator (e.g., a donor site or acceptor site) or an RNA binding region of given miRNA (i.e., an miRNA-binding region of the target gene) and inhibits or suppresses functions of the given selective splicing regulator or miRNA 2. Constitution of the Nucleic Acid of the Present Invention The nucleic acid of the present invention comprises at least one hairpin-shaped DNA ligated to a nucleic acid fragment. Hereafter, the constitution of the nucleic acid of the present invention and embodiments of the ligation of hairpin-shaped DNA to a nucleic acid fragment in the nucleic acid are described in detail.

2-1. Nucleic Acid in which Hairpin-Shaped DNA is Ligated to a Double-Stranded Nucleic Acid Fragment In a nucleic acid in which hairpin-shaped DNA is ligated to a double-stranded nucleic acid fragment, the hairpin-shaped DNA of the present invention can be ligated to up to 4 ends; i.e., the 5' ends and the 3' ends of the double-stranded nucleic acid fragments. In general, one or two hairpin-shaped DNAs may be ligated to the double-stranded nucleic acid fragment, so as to exert the effects of the nucleic acid of the present invention.

Embodiments of the ligation of the double-stranded nucleic acid fragment to hairpin-shaped DNA are determined depending on the number of hairpin-shaped DNAs subjected to ligation and types of functional nucleic acids contained in the double-stranded nucleic acid fragment.

(1) When a Nucleic Acid has One Hairpin-Shaped DNA

There are three embodiments of the ligation of the double-stranded nucleic acid fragment to hairpin-shaped DNA, as shown in FIG. 3. The nucleic acid of the present invention may employ any embodiment of ligation. In such a case, any types of functional nucleic acids may be contained in the double-stranded nucleic acid fragment. Specifically, a base sequence of siRNA composed of RNA or of mature double-stranded miRNA may be contained. Alternatively, a base sequence of a target molecule-binding region such as decoy DNA composed of DNA may be contained.

(I) Nucleic Acid in which the 5' End of Hairpin-Shaped DNA is Ligated to the 3' End of One Nucleic Acid Fragment Constituting a Double-Stranded Nucleic Acid Fragment (FIG. 3 (A))

According to this embodiment, the 3' end of hairpin-shaped DNA is not ligated to the 5' end of the other nucleic acid fragment constituting a double-stranded nucleic acid fragment. The nucleic acid of the present invention according to this embodiment is composed of two nucleic acid fragments (i.e., a nucleic acid fragment comprising a nucleic acid fragment of a double-stranded nucleic acid fragment ligated to hairpin-shaped DNA and the other nucleic acid fragment of the double-stranded nucleic acid fragment).

When the double-stranded nucleic acid fragment contains an siRNA base sequence according to this embodiment, whether the 5' end of hairpin-shaped DNA is to be ligated to the 3' end of a nucleic acid fragment comprising the base sequence of an siRNA sense strand or that of a nucleic acid fragment comprising the base sequence of an antisense strand is not particularly limited. A nucleic acid comprising hairpin-shaped DNA ligated to the 3' end of a nucleic acid fragment comprising the base sequence of an siRNA sense strand as shown in FIG. 4 (A) or a nucleic acid comprising hairpin-shaped DNA ligated to the 3' end of a nucleic acid fragment comprising the base sequence of an siRNA antisense strand, as shown in FIG. 4 (D), may be used.

(II) Nucleic Acid in which the 5' End of Hairpin-Shaped DNA is Ligated to the 3' End of One Nucleic Acid Fragment Constituting a Double-Stranded Nucleic Acid Fragment (FIG. 3 (B))

According to this embodiment, the 3' end of hairpin-shaped DNA is not ligated to the 5' end of the other nucleic acid fragment constituting a double-stranded nucleic acid fragment. As with the case of (A) above, the nucleic acid of the present invention of this embodiment is constituted by two nucleic acid fragments; i.e., a nucleic acid fragment comprising hairpin-shaped DNA ligated to a nucleic acid fragment of a double-stranded nucleic acid fragment and the other nucleic acid fragment of the double-stranded nucleic acid fragment.

When the double-stranded nucleic acid fragment contains an siRNA base sequence according to this embodiment, whether the 3' end of hairpin-shaped DNA is ligated to the 5' end of a nucleic acid fragment comprising the base sequence of an siRNA sense strand or that of a nucleic acid fragment comprising the base sequence of the antisense strand is not particularly limited. A nucleic acid comprising hairpin-shaped DNA ligated to the 5' end of a nucleic acid fragment comprising the base sequence of an siRNA sense strand as shown in FIG. 4 (B) or a nucleic acid comprising hairpin-shaped DNA ligated to the 5' end of a nucleic acid fragment containing a base sequence of an siRNA antisense strand as shown in FIG. 4 (C) may be used.

(III) A Nucleic Acid in which the 3' End of Hairpin-Shaped DNA is Ligated to the 5' End of One Nucleic Acid Fragment Constituting a Double-Stranded Nucleic Acid Fragment and the 5' End of Hairpin-Shaped DNA is Ligated to the 3' End of the Other Nucleic Acid Fragment (FIG. 3 (C))

According to this embodiment, the 5' end and the 3' end of hairpin-shaped DNA each are ligated to each nucleic acid fragment constituting a double-stranded nucleic acid fragment. As a result, the nucleic acid of the present invention according to this embodiment is constituted by a nucleic acid fragment comprising the constituents below sequentially ligated from the 5' end toward the 3' end:

one nucleic acid fragment of the double-stranded nucleic acid fragment;

hairpin-shaped DNA; and the other nucleic acid fragment of the double-stranded nucleic acid fragment.

When the double-stranded nucleic acid fragment of this embodiment comprises an siRNA base sequence, either of the nucleic acids below may be used:

(i) the nucleic acid comprising the constituents below sequentially ligated from the 5' end toward the 3' end, as shown in FIG. 4 (E):

a nucleic acid fragment comprising the base sequence of an siRNA sense strand; hairpin-shaped DNA; and a nucleic acid fragment comprising the base sequence of an siRNA antisense strand; or (ii) the nucleic acid comprising the constituents below sequentially ligated from the 5' end toward the 3' end, as shown in FIG. 4 (F):

a nucleic acid fragment comprising the base sequence of an siRNA antisense strand;

hairpin-shaped DNA; and a nucleic acid fragment comprising the base sequence of an siRNA sense strand.

(2) When a Nucleic Acid has Two Hairpin-Shaped DNAs

Nucleic acids can be roughly classified into the following three embodiments depending on the number of non-ligated regions between the double-stranded nucleic acid fragment and hairpin-shaped DNA. The nucleic acid of the present invention may be in accordance with any embodiment, and any types of functional nucleic acids may be contained in the double-stranded nucleic acid fragment. Specifically, a base sequence of siRNA mainly constituted by RNA or mature double-stranded miRNA may be contained therein. Alternatively, a base sequence of a target molecule-binding region, such as decoy DNA, mainly constituted by DNA may be contained therein.

(I) When a Nucleic Acid Contains One Non-Ligated Region

According to this embodiment, a non-ligated region exists between an end of one nucleic acid fragment constituting a double-stranded nucleic acid fragment and an end of hairpin-shaped DNA. The nucleic acid according to this embodiment is accordingly constituted in the form of a nucleic acid fragment comprising two nucleic acid fragments each constituting a double-stranded nucleic acid fragment ligated to one of two hairpin-shaped DNAs.

The nucleic acid according to this embodiment can further be classified into the following two embodiments based on the position of a non-ligated region between the double-stranded nucleic acid fragment and hairpin-shaped DNA, as shown in FIG. 5.

(i) A nucleic acid comprising nucleic acid fragments and hairpin-shaped DNAs ligated from the 5' end toward the 3' end in the following order (FIG. 5 (A)):

one nucleic acid fragment constituting a double-stranded nucleic acid fragment;

hairpin-shaped DNA;

the other nucleic acid fragment constituting a double-stranded nucleic acid fragment; and hairpin-shaped DNA.

According to this embodiment, the 5' end of one nucleic acid fragment constituting a double-stranded nucleic acid fragment is not ligated to the 3' end of hairpin-shaped DNA. When the double-stranded nucleic acid fragment contains an siRNA base sequence according to this embodiment, either a nucleic acid fragment comprising the base sequence of an siRNA sense strand or a nucleic acid fragment comprising the base sequence of an siRNA antisense strand may correspond to "one nucleic acid fragment" mentioned above. Specifically, "one nucleic acid fragment" mentioned above may be a nucleic acid fragment comprising the base sequence of an siRNA sense strand, while "the other nucleic acid fragment" may be a nucleic acid fragment comprising the base sequence of an siRNA antisense strand, as shown in FIG. 6 (A). Alternatively, "one nucleic acid fragment" mentioned above may be a nucleic acid fragment comprising the base sequence of an siRNA antisense strand and "the other nucleic acid fragment" may be a nucleic acid fragment comprising the base sequence of an siRNA sense strand, as shown in FIG. 6 (C).

(ii) A nucleic acid comprising nucleic acid fragments and hairpin-shaped DNAs ligated from the 5' end toward the 3' end in the following order (FIG. 5 (B)):

hairpin-shaped DNA;

one nucleic acid fragment constituting a double-stranded nucleic acid fragment;

hairpin-shaped DNA; and the other nucleic acid fragment constituting a double-stranded nucleic acid fragment.

According to this embodiment, the 3' end of a nucleic acid fragment constituting a double-stranded nucleic acid fragment is not ligated to the 5' end of hairpin-shaped DNA. When the double-stranded nucleic acid fragment contains an siRNA base sequence according to this embodiment, accordingly, either a nucleic acid fragment comprising the base sequence of an siRNA sense strand or a nucleic acid fragment comprising the base sequence of an siRNA antisense strand may correspond to "one nucleic acid fragment" mentioned above without any particular limitation, as with the case of (i) above. Specifically, "one nucleic acid fragment" mentioned above may be a nucleic acid fragment comprising the base sequence of an siRNA sense strand, and "the other nucleic acid fragment" may be a nucleic acid fragment comprising the base sequence of an siRNA antisense strand, as shown in FIG. 6 (D). Alternatively, "one nucleic acid fragment" mentioned above may be a nucleic acid fragment comprising the base sequence of an siRNA antisense strand and "the other nucleic acid fragment" may be a nucleic acid fragment comprising the base sequence of an siRNA sense strand, as shown in FIG. 6 (B).

(II) When a Nucleic Acid Contains Two Non-Ligated Regions

According to this embodiment, non-ligated regions exist between an end of each of the two nucleic acid fragments constituting a double-stranded nucleic acid fragment and an end of hairpin-shaped DNA.

The nucleic acid according to this embodiment can further be classified into the embodiments (i) and (ii) below based on positions of non-ligated regions between the double-stranded nucleic acid fragment and hairpin-shaped DNA, as shown in FIG. 7.

(i) A Nucleic Acid Comprising Hairpin-Shaped DNAs Ligated to the 5' End and the 3' End of One Nucleic Acid Fragment Constituting a Double-Stranded Nucleic Acid Fragment (FIG. 7 (A))

The nucleic acid of this embodiment is composed of two nucleic acid fragments; i.e., a nucleic acid fragment comprising two hairpin-shaped DNAs ligated to one nucleic acid fragment of a double-stranded nucleic acid fragment and the other nucleic acid fragment of the double-stranded nucleic acid fragment. In the nucleic acid of this embodiment, specifically, hairpin-shaped DNA is not ligated to either end (i.e., the 5' end or the 3' end) of the other nucleic acid fragment. Thus, two non-ligated regions exist between both ends of the other nucleic acid fragment and an end of each of two hairpin-shaped DNAs.

When the double-stranded nucleic acid fragment contains an siRNA base sequence according to this embodiment, "the other nucleic acid fragment" may be either a nucleic acid fragment comprising the base sequence of an siRNA sense strand or a nucleic acid fragment comprising the base sequence of an siRNA antisense strand. Specifically, "one nucleic acid fragment" mentioned above may be a nucleic acid fragment comprising the base sequence of an siRNA sense strand, and "the other nucleic acid fragment" may be a nucleic acid fragment comprising the base sequence of an siRNA antisense strand, as shown in FIG. 8 (A).

Alternatively, "one nucleic acid fragment" mentioned above may be a nucleic acid fragment comprising the base sequence of an siRNA antisense strand and "the other nucleic acid fragment" may be a nucleic acid fragment comprising the base sequence of an siRNA sense strand, as shown in FIG. 8 (B).

(ii) A Nucleic Acid in which Hairpin-Shaped DNA is Ligated to Each of the Nucleic Acid Fragments Constituting a Double-Stranded Nucleic Acid Fragment (FIGS. 7 (B) and (C))

The nucleic acid according to this embodiment is composed of two nucleic acid fragments in which hairpin-shaped DNA is ligated to each of the nucleic acid fragments constituting a double-stranded nucleic acid fragment.

The nucleic acid according to this embodiment can further be classified into two embodiments: i.e., a nucleic acid comprising hairpin-shaped DNA ligated to the 5' end of each of the nucleic acid fragments constituting a double-stranded nucleic acid fragment as shown in FIG. 7 (B); and a nucleic acid comprising hairpin-shaped DNA ligated to the 3' end of each of the nucleic acid fragments constituting a double-stranded nucleic acid fragment as shown in FIG. 7 (C). The nucleic acid according to this embodiment may be of any such embodiments.

When a double-stranded nucleic acid fragment comprises an siRNA base sequence according to this embodiment of ligation, a nucleic acid may comprise hairpin-shaped DNA ligated to the 3' end of each of a nucleic acid fragment comprising a base sequence of the siRNA sense and antisense strands as shown in FIG. 8 (C). Alternatively, a nucleic acid may comprise hairpin-shaped DNA ligated to the 5' end of each of a nucleic acid fragment comprising a base sequence of the siRNA sense and antisense strands as shown in FIG. 8 (D).

(III) When a Nucleic Acid does not Comprise a Non-Ligated Region (FIG. 9)

In the nucleic acid of this embodiment, all ends of the double-stranded nucleic acid fragment are ligated to the ends of two hairpin-shaped DNAs. Specifically, the nucleic acid of this embodiment comprises the following nucleic acid fragments and hairpin-shaped DNAs sequentially ligated from the 5' end toward the 3' end, and the 5' end is ligated to the 3' end:

one nucleic acid fragment constituting a double-stranded nucleic acid fragment;
hairpin-shaped DNA;
the other nucleic acid fragment constituting a double-stranded nucleic acid fragment; and
hairpin-shaped DNA.

The nucleic acid according to this embodiment is further classified into the following three embodiments depending on the positions and number of nicks in the double-stranded nucleic acid fragment region.

(i) When a Double-Stranded Nucleic Acid Fragment Region Comprises No Nicks (FIG. 9 (A))

According to this embodiment, the nucleic acid of the present invention is in a closed circular state and forms a so-called dumbbell-shaped structure.

According to this embodiment, any types of functional nucleic acids may be contained in the double-stranded nucleic acid fragment. When the double-stranded nucleic acid fragment contains a base sequence of a target molecule-binding region mainly constituted by DNA, such as decoy DNA, such embodiment is particularly preferable.

(ii) When any One of the Nucleic Acid Fragment Regions Constituting a Double-Stranded Nucleic Acid Fragment Comprises a Nick (FIG. 9 (B))

According to this embodiment, the nucleic acid of the present invention has a constitution similar to that of the nucleic acid described in "(2) When a nucleic acid has two hairpin-shaped DNAs, (I) When 2 nucleic acid contains one non-ligated region" above. It should be noted that the nucleic acid of this embodiment differs from the nucleic acid of (2) (I) above in that a nick (i.e., a non-ligated region) is located within a double-stranded nucleic acid fragment instead of a site between a nucleic acid fragment constituting a double-stranded nucleic acid fragment and hairpin-shaped DNA.

According to this embodiment, an example of a functional nucleic acid contained in the double-stranded nucleic acid fragment is a target molecule-binding region mainly composed of DNA, such as decoy DNA. The nick may be located within the binding region.

(iii) When Each of the Nucleic Acid Fragment Regions Constituting a Double-Stranded Nucleic Acid Fragment has a Nick (i.e., Two Nicks in Total) and Such Nicks are not Paired (FIG. 9 (C)).

According to this embodiment, the nucleic acid of the present invention has a constitution similar to that of the nucleic acid according to (2) (II) (ii) above. It should be noted that the nucleic acid of this embodiment differs from the nucleic acid described in "(2) When a nucleic acid contains two hairpin-shaped DNAs (II) When a nucleic acid contains two non-ligated regions (ii)" above in that a nick (i.e., a non-ligated region) is located within a double-stranded nucleic acid fragment instead of a site between a nucleic acid fragment constituting a double-stranded nucleic acid fragment and hairpin-shaped DNA.

The term "nicks are not paired" refers to a situation in which nicks are not present at the same corresponding sites in each of the nucleic acid fragment regions constituting a double-stranded nucleic acid fragment. In the nucleic acid of this embodiment, accordingly, at least 1 and preferably at least 2 base pairs are present between two nicks.

An example of a functional nucleic acid contained in the double-stranded nucleic acid fragment of this embodiment is a target molecule-binding region mainly composed of DNA, such as decoy DNA. The nick may be present within such binding region.

2-2. A Nucleic Acid in which Hairpin-Shaped DNA is Ligated to a Single-Stranded Nucleic Acid Fragment A nucleic acid in which hairpin-shaped DNA is ligated to a single-stranded nucleic acid fragment can comprise hairpin-shaped DNA ligated to the 5' end and/or the 3' end of the single-stranded nucleic acid fragment.

Embodiments of the ligation between the single-stranded nucleic acid fragment and hairpin-shaped DNA are determined depending on the number of hairpin-shaped DNAs ligated.

(1) When a Nucleic Acid has One Hairpin-Shaped DNA

Figure 10:
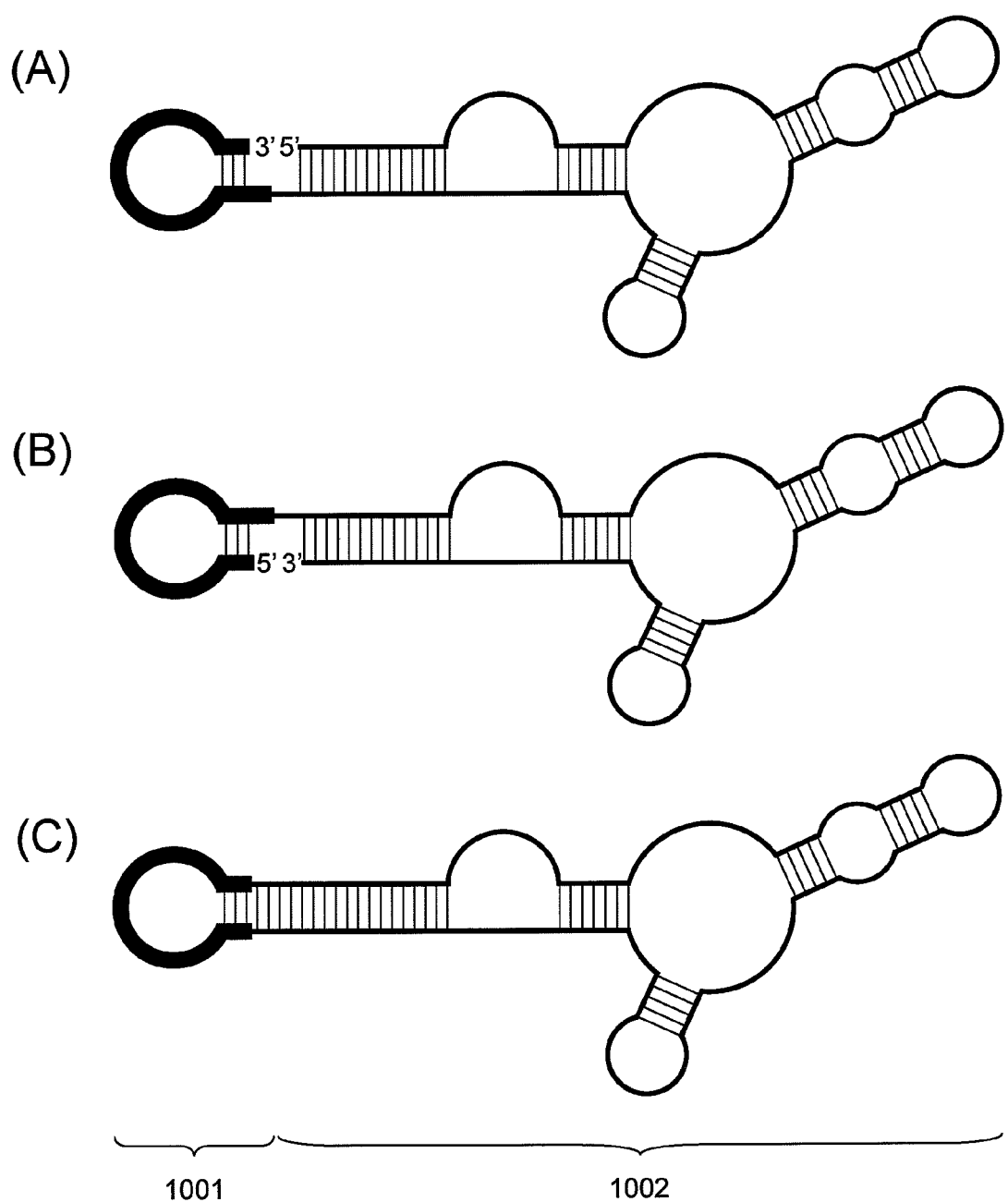
FIG. 10 is a conceptual diagram showing an embodiment of the nucleic acid of the present invention comprising a hairpin-shaped DNA (1001) ligated to a single-stranded nucleic acid fragment (1002).

As described below, there are three embodiments of the ligation between the single-stranded nucleic acid fragment and hairpin-shaped DNA, as shown in FIG. 10. The nucleic acid of the present invention may be of any embodiment. Any types of functional nucleic acids may be contained in the single-stranded nucleic acid fragment. For example, a base sequence of a single-stranded miRNA precursor, shRNA, a nucleic acid aptamer, a ribozyme (including deoxyribozyme), a molecular beacon, riboswitch, a U1 adaptor, or a target molecule-binding region can be contained.

(I) A Nucleic Acid in which the 5' End of Hairpin-Shaped DNA is Ligated to the 3' End of a Single-Stranded Nucleic Acid Fragment (FIG. 10 (A))

The nucleic acid of this embodiment is composed of a nucleic acid fragment comprising a single-stranded nucleic acid fragment and hairpin-shaped DNA ligated thereto. The 5' end of the nucleic acid is derived from a single-stranded nucleic acid fragment and the 3' end thereof is derived from hairpin-shaped DNA.

(II) A nucleic acid in which the 3' end of hairpin-shaped DNA is ligated to the 5' end of a single-stranded nucleic acid fragment (FIG. 10 (B))

The nucleic acid of this embodiment is composed of a nucleic acid fragment comprising a single-stranded nucleic acid fragment and hairpin-shaped DNA ligated thereto. The nucleic acid of this embodiment is structurally different from (I) above in that the 5' end is derived from hairpin-shaped DNA and the 3' end is derived from a single-stranded nucleic acid fragment.

(III) A Nucleic Acid in which the 5' End and the 3' End of Hairpin-Shaped DNA are Ligated to the 3' End and the 5' End of a Single-Stranded Nucleic Acid Fragment, Respectively (FIG. 10 (C))

The nucleic acid of this embodiment is in the form of a closed circular nucleic acid in which a single-stranded nucleic acid fragment is ligated to hairpin-shaped DNA.

(2) When a Nucleic Acid has Two Hairpin-Shaped DNAs

Figure 11:
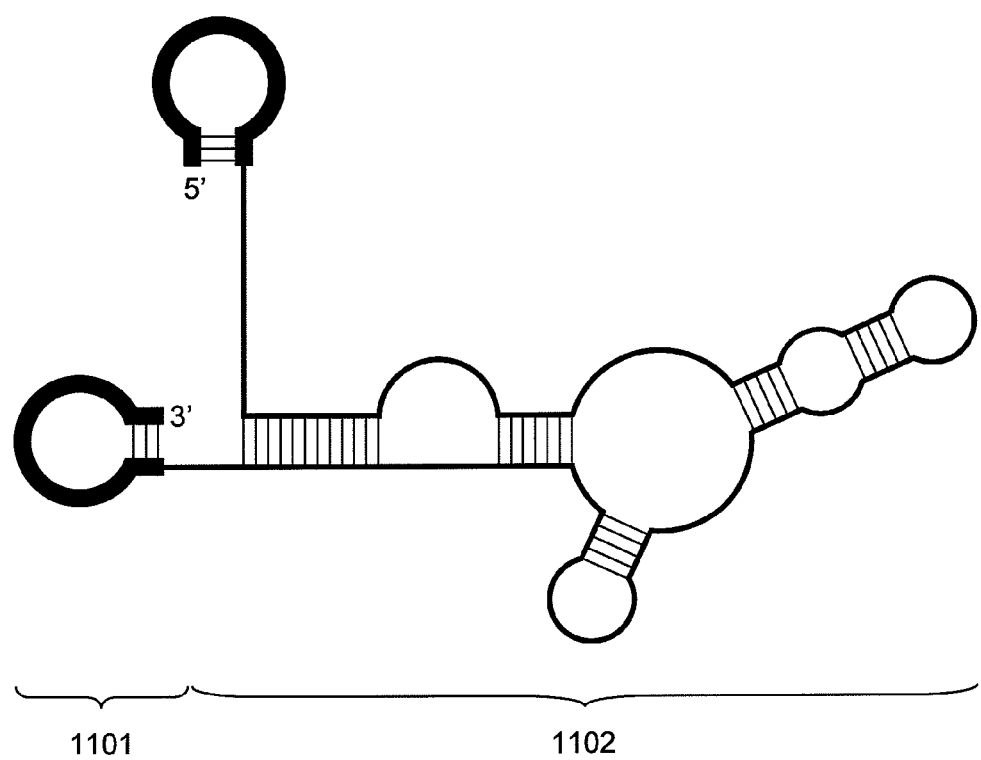
FIG. 11 is a conceptual diagram showing embodiments of the nucleic acid of the present invention comprising two hairpin-shaped DNAs (1101) ligated to a single-stranded nucleic acid fragment (1102).

The nucleic acid of this embodiment comprises two hairpin-shaped DNAs ligated to the 5' end and the 3' end of a single-stranded nucleic acid fragment (FIG. 11).

The nucleic acid of this embodiment is in the form of a nucleic acid fragment comprising a single-stranded nucleic acid fragment ligated to two hairpin-shaped DNAs in such a manner that the single-stranded nucleic acid fragment is sandwiched by two hairpin-shaped DNAs.

In the nucleic acid of this embodiment, any types of functional nucleic acids can be contained in the single-stranded nucleic acid fragment region. For example, a base sequence of any of a single-stranded miRNA precursor, shRNA, a nucleic acid aptamer, a ribozyme (including deoxyribozyme), a molecular beacon, riboswitch, or a U1 adaptor can be contained.

3. Production of the Nucleic Acid of the Present Invention

Hairpin-shaped DNA in the nucleic acid of the present invention is mainly composed of DNA, and the nucleic acid fragment is composed of DNA, RNA, a nucleotide analogue, or a mixture of any thereof.

Accordingly, the nucleic acid of the present invention can be chemically synthesized in accordance with a known solid-phase synthesis technique based on the sequence of the nucleic acid of the present invention that has been designed in advance, in principle. Regarding a chemical synthesis technique for nucleic acids, reference can be made to, for example, Current Protocols in Nucleic Acid Chemistry, Volume 1, Section 3. Many life sciences manufacturers (e.g., Takara Bio, Life Technologies Corporation, and Sigma-Aldrich Corporation) provide contract manufacturing services for chemical synthesis, and services provided thereby can be utilized.

After chemical synthesis, the nucleic acid of the present invention is preferably purified before use by a method known in the art. Examples of purification techniques include gel purification, affinity column purification, and HPLC.

When the nucleic acid of the present invention is composed of two nucleic acid fragments (for example, when it has a structure shown in FIG. 3 (A) and FIG. 3 (B), FIG. 7 (A) to FIG. 7 (C), or FIG. 9 (C)), the nucleic acid of the present invention can be prepared by chemically synthesizing nucleic acid fragments independently, purifying the same as necessary, and mixing two nucleic acid fragments of preferably equivalent amounts so that they anneal with each other.

When the nucleic acid of the present invention is composed of a nucleic acid fragment (for example, when it has a structure shown in FIG. 3 (C), FIG. 5 (A) to FIG. 5 (B), FIG. 9 (B), FIG. 10 (A), FIG. 10 (B), or FIG. 11), the nucleic acid of the present invention can be prepared by chemically synthesizing a nucleic acid fragment, purifying the same as necessary, and placing the resultant under conditions that allow intramolecular annealing.

When the nucleic acid of the present invention has a closed-circular form as shown in FIG. 9 (A) and FIG. 10 (C), for example, a nucleic acid fragment having a nick at an adequate site within the nucleic acid is chemically synthesized, the resultant is purified as necessary, and both ends of the single nucleic acid fragment may be ligated to each other by a method known in the art. For example, such ends can be ligated biochemically with the use of an enzyme such as a ligase.

4. Effects

The nucleic acid of the present invention can enhance resistance of a double-stranded nucleic acid fragment or a single-stranded nucleic acid fragment forming a higher-order structure via intramolecular annealing to degradation by a nucleolytic enzyme, compared with the resistance attained when such nucleic acid fragment is used alone or when a known linker nucleic acid or a nucleic acid such as a hairpin-shaped nucleic acid that imparts degradation resistance is ligated to such nucleic acid fragment. Thus, the stability of the functional nucleic acids contained in the double-stranded nucleic acid fragments or the like in vivo can be enhanced, and pharmacological effects of such functional nucleic acids can be maintained and/or enhanced.

According to the present invention, in addition, the nucleic acid of the present invention was found to be capable of imparting resistance to degradation by a nucleolytic enzyme even it does not have a closed-circular form, such as a known dumbbell-shaped nucleic acid (i.e., even it comprises one or two non-ligated regions). The fact that the nucleic acid has such a non-ligated region is very useful in respect of simplification of the preparation of functional nucleic acids or reduction in production costs. Specifically, when preparing the nucleic acid of the present invention, for example, the process of nucleic acid cyclization, which had heretofore been conducted with a dumbbell-shaped nucleic acid, can be omitted, and a dumbbell-shaped nucleic acid that had been chemically synthesized as a single long linear nucleic acid can be divided into two linear nucleic acids and then chemically synthesized.

Further, preparation of the nucleic acid of the present invention can be fundamentally completed via chemical synthesis alone, and performance of purification and annealing is sufficient as subsequent processing. It is thus excellent in that nucleic acids of interest can be mass-produced in a cost-effective manner.

II. Pharmaceutical Composition

The second aspect of the present invention relates to a pharmaceutical composition.

1. Constitution of a Pharmaceutical Composition

The pharmaceutical composition of the present invention comprises, as an active ingredient, the nucleic acid according to the first aspect.

The amount of the nucleic acid of the present invention in the pharmaceutical composition of the present invention may be a pharmaceutically effective amount.

The term "pharmaceutically effective amount" used herein refers to a dose that is necessary for an active ingredient of a pharmaceutical composition (i.e., a functional nucleic acid in the nucleic acid of the present invention) to exert its functions that imposes no or substantially no side effects harmful to organisms to which the pharmaceutical composition is administered. The specific dose varies depending on the type of functional nucleic acid used, the target molecule, the dosage form to be employed, information regarding the subject, and the route of administration. When a pharmaceutical composition is administered to a human, a pharmaceutically effective amount and a preferable route of administration are generally determined based on the data obtained as a result of cell culture assays and animal experimentation. The final dose is determined and adjusted by a doctor in accordance with the individual subject. In such a case, examples of information regarding the subject that is to be taken into consideration include the extent or severity of a disease, general physical conditions, age, body weight, sexuality, eating habits, drug sensitivity, and resistance to treatment and the like.

A specific example of the amount of the nucleic acid of the present invention per dose is about 0.01% (w/v) to about 20% (w/v), and preferably about 0.1% (w/v) to about 10% (w/v) when the nucleic acid of the present invention containing siRNA is administered in the form of an injection to a human adult male (body weight: 60 kg) who is not in need of other pharmaceuticals. When administration of a large quantity of the nucleic acid of the present invention is required in order to attain pharmacological effects of the pharmaceutical composition of the present invention, administration can be carried out in several separate instances in order to reduce burdens on a subject.

The pharmaceutical composition of the present invention can comprise a pharmaceutically acceptable carrier. The term "pharmaceutically acceptable carrier" refers to a solvent and/or additive that is generally used in the pharmaceutical field.

Examples of "solvents" include water (e.g., saline, buffer, and glucose solution) and pharmaceutically acceptable organic solvents (e.g., ethanol, propylene glycol, ethoxylated isostearyl alcohol, polyoxylated isostearyl alcohol, and polyoxyethylene sorbitan fatty acid esters). Such solvents are preferably sterilized. It is preferable that the solvents is adjusted to be isotonic with blood, as the saline, as necessary.

Examples of "additives" include excipients, adsorption inhibitors, binders, disintegrators, fillers, emulsifiers, flow modifiers, and lubricants.

Examples of excipients include saccharides, such as monosaccharides, disaccharides, cyclodextrins, and polysaccharides (specific examples include, but are not limited to, glucose, sucrose, lactose, raffinose, mannitol, sorbitol, inositol, dextrin, maltodextrin, starch, and cellulose), metal salts (e.g., sodium phosphate or calcium phosphate, calcium sulfate, and magnesium sulfate), citric acids, tartaric acids, glycine, low-, middle-, or high-molecular weight polyethylene glycol (PEG), Pluronic, and combinations of any thereof.

Examples of adsorption inhibitors include Tween 80, Tween 20, gelatin, and human serum albumin.

Examples of binders include starch pastes using maize, wheat, rice, or potato starch, gelatin, Tragacanth, methyl cellulose, hydroxypropyl methylcellulose, carboxymethylcellulose sodium, and polyvinyl pyrrolidone.

Examples of disintegrators include the aforementioned starch, carboxymethyl starch, crosslinked polyvinyl pyrrolidone, agar, alginic acid, sodium alginate, and salts of any thereof.

Examples of fillers include the aforementioned sugar and calcium phosphate (e.g., tricalcium phosphate and calcium hydrogen phosphate).

Examples of emulsifiers include sorbitan fatty acid ester, glycerine fatty acid ester, sucrose fatty acid ester, and propylene glycol fatty acid ester.

Examples of flow modifiers and lubricants include silicate, talc, stearate, and polyethylene glycol.

Such carriers are used to facilitate the preparation of pharmaceutical compositions and to maintain dosage forms and pharmacological effects thereof. Carriers may be adequately used as necessary. In addition to the aforementioned additives, stabilizers, flavoring agents, diluents, surfactants, solublizers, absorption promoters, humectants, extenders, moisturising agents, preservatives, antioxidants, buffers, or the like can be added, as necessary.

Further, the pharmaceutical composition of the present invention can comprise other drugs, provided that the pharmacological effects of the nucleic acid of the present invention are maintained. For example, a given amount of antibiotics may be contained.

The dosage form of the pharmaceutical composition of the present invention is not particularly limited, provided that such dosage form does not inactivate a functional nucleic acid contained in the nucleic acid of the present invention and allows the pharmacological effects thereof to be exerted in vivo after administration. For example, a liquid, solid, or semi-solid dosage form may be employed. Specific examples of dosage forms include parenteral dosage forms, such as injections, suspensions, emulsions, eye drops, nasal drops, creams, ointments, plasters, poultices, and suppositories, and oral dosage forms, such as liquid preparations, powders, granules, tablets, capsules, sublingual agents, and troches. In the present invention, the dosage form is preferably an injection since an active ingredient thereof is in the form of a nucleic acid.

2. Production of Pharmaceutical Composition

The pharmaceutical composition of the present invention may be produced by a method known in the art. For example, the method described in Remington's Pharmaceutical Sciences (Merck Publishing Co., Easton, Pa.) may be adopted.

3. Method of Administration of Pharmaceutical Composition

The pharmaceutical composition is preferably administered in a dosage unit form. The pharmaceutical composition can be administered through an oral route, directly into the tissue (e.g., subcutaneous, intramuscular, or intravenous administration), or outside the tissue (e.g., percutaneous, instillation, nasal, or transrectal administration). The pharmaceutical composition of the present invention is preferably administered in a dosage form adequate for the method of administration. When the pharmaceutical composition is directly administered into tissue, for example, injection through the blood stream is preferable. Thus, the dosage form may be a liquid preparation (an injection solution).

When the pharmaceutical composition is administered in the form of an injection, the site of injection is not particularly limited, provided that the nucleic acid of the present invention can exert its functions on the target molecule and achieve an objective of the administration of the pharmaceutical composition. Examples include intravenous, intraarterial, intrahepatic, intramuscular, intraarticular, intramedullary, intraspinal, intraventricular, percutaneous, subcutaneous, intracutaneous, intraperitoneal, intranasal, intestinal, and sublingual sites. An injection into a blood vessel, such as intravenous or intraarterial injection, is preferable since this allows the pharmaceutical composition of the present invention to be immediately distributed throughout the body via the blood stream and invasiveness is relatively low. Alternatively, the pharmaceutical composition may be injected directly into a site at which pharmacological effects of the pharmaceutical composition of the present invention are needed, thus allowing a large amount of the pharmaceutical composition to directly act on the target site.

III. Method of Enhancing Degradation Resistance of Nucleic Acid Fragment

The third aspect of the present invention relates to a method of enhancing resistance of a double-stranded nucleic acid fragment or a single-stranded nucleic acid fragment forming a higher-order structure via intramolecular annealing to degradation by a nucleolytic enzyme and a method for preparing a nucleic acid capable of maintaining in vivo stability by such method.

1. Method of Enhancing Nucleolytic Enzyme Resistance

The method of the present invention is based on the finding that resistance of a nucleic acid fragment to degradation by a nucleolytic enzyme is enhanced by ligating hairpin-shaped DNA according to Embodiment 1 to the end of the nucleic acid fragment in comparison with the resistance attained when a nucleic acid fragment is used alone or when another known linker sequence is ligated to the nucleic acid fragment. According to the method of the present invention, accordingly, hairpin-shaped DNA according to the Embodiment 1 may be ligated to at least one end of the double-stranded nucleic acid fragment or the single-stranded nucleic acid fragment forming a higher-order structure via intramolecular annealing.

2. Method for Preparing Nucleic Acid with Enhanced Nucleolytic Enzyme Resistance The nucleic acid of the present invention comprising the hairpin-shaped DNA according to the Embodiment 1 ligated to the end of a nucleic acid fragment is prepared via chemical synthesis as described in aforementioned "I. 3. Production of the nucleic acid of the present invention". According to the method of the present invention, accordingly, the nucleic acid of the present invention comprising hairpin-shaped DNA ligated to a given site of a nucleic acid fragment of interest that is a target for enhancement in resistance to degradation by a nucleolytic enzyme is designed in advance, and chemical synthesis is performed based on such design. As a result, hairpin-shaped DNA is ligated to a given site.

The nucleic acid of the present invention may be adequately designed based on any embodiment described in Embodiment 1.

3. Effects

According to the method of improving resistance of the present invention, resistance to degradation by a nucleolytic enzyme is imparted to a nucleic acid fragment that had previously been susceptible to degradation by a nucleolytic enzyme and unstable in vivo. Thus, a given nucleic acid fragment can be stabilized to a greater extent than in a case involving the use of a nucleic acid fragment alone, other known linker nucleic acids, or hairpin nucleic acids that are known to impart degradation resistance. When a nucleic acid fragment comprises a functional nucleic acid, accordingly, effects thereof can be maintained and/or enhanced for a longer period of time. Effects of such functional nucleic acid can be consequently enhanced.

EXAMPLES

<Example 1> Preparation of Nucleic Acid Comprising siRNA Base Sequence

In Example 1, the nucleic acids of the present invention comprising hairpin-shaped DNA ligated to at least one end of a double-stranded nucleic acid fragment comprising the siRNA base sequence were prepared, used for Examples 2 to 5 were prepared.

Figure 13:
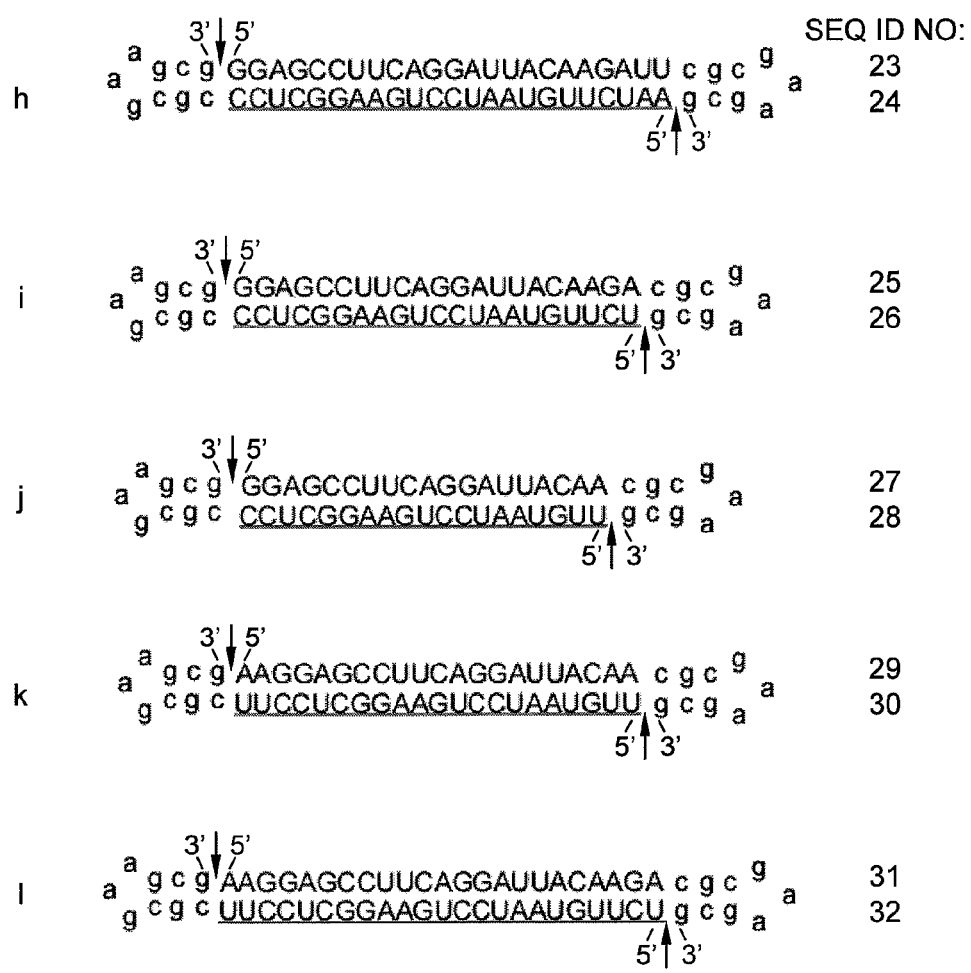
FIG. 13 shows various nucleic acid sequences and structures containing siRNA targeting firefly luciferase mRNA prepared in Example 1. An arrow indicates a non-ligated region (a nick region). DNA sequences are represented by lower-case letters and RNA sequences are represented by upper-case letters. An underlined sequence represents an siRNA antisense strand (a guide strand).

Firefly luciferase mRNA was designated as the siRNA target to be used for the experiment, and various nucleic acid fragments were designed. The structures of various nucleic acids and base sequences thereof are shown in FIGS. 12 and 13. In the base sequences, a region indicated by upper-case letters is composed of RNA and a region indicated by lower-case letters is composed of DNA. In FIG. 12, "Cont. I" to "Cont. III" represent control nucleic acids each consisting only of a double-stranded nucleic acid fragment comprising siRNA of firefly luciferase mRNA. Cont. I and Cont. II comprise 2-base overhangs at the 3' end of the sense strand and that of the antisense strand and have a structure of conventional siRNA. Cont. III is a control nucleic acid consisting of a 25-mer blunt-ended double-stranded nucleic acid fragment comprising siRNA. In FIG. 12, "a" to "d" (hereafter, "a" to "d" indicate "nucleic acid a" to "nucleic acid d", respectively) represent a nucleic acid of the present invention comprising two hairpin-shaped DNAs as described in the present invention ligated to a 3' terminal region of each nucleic acid fragment constituting the nucleic acid (Cont. III). Each of nucleic acids a to d has a different hairpin-shaped DNA sequence. Nucleic acid e was derived from nucleic acid b by substitution of a hairpin-shaped DNA region with RNA, which was prepared as a control for hairpin-shaped DNA. Nucleic acid f and nucleic acid g represent the nucleic acid of the present invention comprising hairpin-shaped DNA described in the present invention ligated to only one end of Cont. III. In FIG. 13, "h" to "l" (hereafter, "h" to "l" indicate "nucleic acid h" to "nucleic acid l", respectively) are derived from nucleic acid b by changing the number of terminal bases of siRNA contained in the double-stranded nucleic acid fragment region without changing hairpin-shaped DNA.

Synthesis of nucleic acid fragments of the various nucleic acids designed was entrusted to Hokkaido System Science Co., Ltd. (Hokkaido, Japan), and synthesis was carried out in accordance with a known solid-phase synthesis technique. Subsequently, the synthesized nucleic acid fragments were subjected to purification by gel electrophoresis, the equivalent amounts of base-paired nucleic acid fragments were mixed in a phosphate buffer (pH 7.4), and, the resulting mixture was heated at 90° C. and gradually cooled down to 25° C. for annealing, and the nucleic acid of the present invention was thus prepared.

Figure 14:
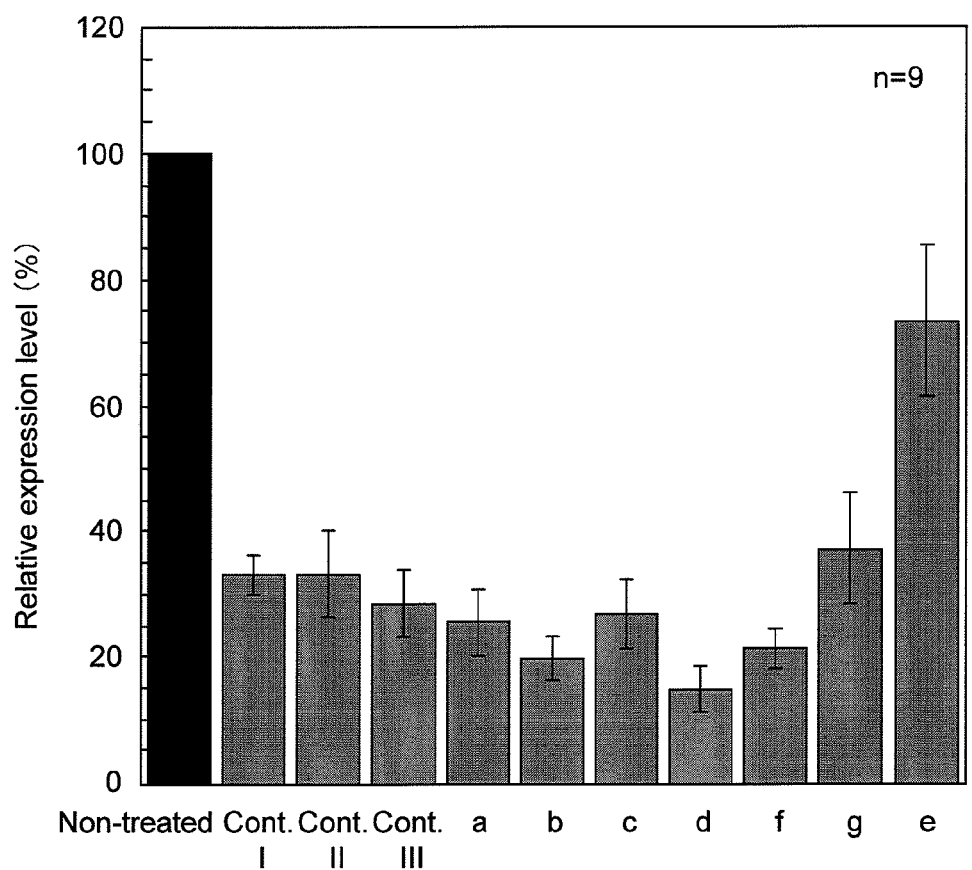
FIG. 14 shows the results of suppression of firefly luciferase expression by various nucleic acids containing firefly luciferase siRNAs in HeLa cells. The results show relative expression levels of firefly luciferase, corrected by the expression levels of *Renilla reniformis* luciferase. The relative luciferase emission obtained when samples were not treated with siRNA-containing nucleic acids (without treatment) was designated as 100%.

<Example 2> Inhibition of Firefly Luciferase Gene Expression by the Nucleic Acid of the Present Invention In Vitro In Example 2, inhibitory effects of various nucleic acids containing siRNA prepared in Example 1 (i.e., Cont. I to Cont. III and nucleic acids a to g) on firefly luciferase gene expression were examined. Inhibitory effects were assayed by introducing the various nucleic acids of Example 1 into HeLa cells via lipofection together with a plasmid that encodes the firefly luciferase gene as the target molecule and measuring the luciferase emission intensity to examine the inhibitory effects of the various nucleic acids on gene expression.
(1) Cell Culture HeLa cells were cultured under 5% $CO_2$ at 37° C. and grown in a MEM medium (Eagle's Minimum Essential Medium, Sigma) containing 10% fetal bovine serum (FBS, JRH BIOSCIENCES). and antibiotics (final concentration; penicillin: 100 U/mL, and streptomycine: 100 μg/mL)
(2) Introduction of Various Nucleic Acids Prepared in Example 1 and Plasmids into Culture Cells HeLa cells were seeded on a 96-well plate at $1.5 \times 10^4$ cells/well (100 μL) and cultured in an antibiotic-free MEM medium containing 10% fetal bovine serum for 24 hours. Transfection was carried out with the use of 0.5 μL of Lipofectamine 2000 (Invitrogen) per well by adding 50 μL solution mixed with 200 ng of plasmids encoding the firefly luciferase gene (pGL3-control, Promega) per well, 200 ng of plasmids encoding the *Renilla reniformis* luciferase gene (pGL4.74 [hRluc/TK], Promega) per well, and various nucleic acids prepared in Example 1 to a final concentration of 0.1 nM in OPTI-MEM medium (Invitrogen).
(3) Analysis of Inhibitory Effects on Gene Expression Culture was continued for 22 hours after transfection, firefly luciferase emissions and *Renilla reniformis* luciferase emissions were quantified using the Dual-Luciferase Reporter Assay System (Promega), and inhibitory effects on protein expression of the firefly luciferase as an siRNA target were examined. Specifically, the cells were washed twice with 100 μL of PBS per well after transfection, 20 μL of a lysis buffer was added thereto, and the cells were lysed with gentle agitation at 25° C. for 30 minutes. The LARII reagent (100 μL) was added to and mixed with the solution, and firefly luciferase emissions were detected with the use of LAS-4000 (Fuji Film) (exposure time: 120 seconds). Subsequently, the Stop & Glo reagent (100 μL) was added to detect *Renilla reniformis* luciferase emissions (exposure time: 200 seconds), and each emission intensity was quantified with the ScienceLab 2005 MultiGauge (Fuji Film). When detecting emissions, as the background, the quantity of emissions from the samples without transfection was subtracted from that of each type of luciferase emission. The firefly emission was divided by the *Renilla reniformis* luciferase emissions, which was a control sample coexpressed therewith, and the assayed values were normalized. The value attained in the absence of an siRNA-containing nucleic acid was designated as 100%, and the relative activity of the luciferase as the target molecule in the presence of a variety of siRNAs was determined. In addition, the relative activity of the luciferase as the target molecule in the presence of a variety of siRNAs with different concentrations was determined, and the $IC_{50}$ value was determined based on a graph plotting relative activity in relation to concentration. Specifically, the value of interest was determined with the use of KaleidaGraph (Albeck Software) by applying the obtained value to a calculation formula: $Y=M4+(M3-M4)/(1+10^{\wedge}((LOG(M0)-LOG(M1))*M2))$ [default value: M1=M2=M3=1, M4=100] carrying out data fitting using the least-square method. Y (%) is relative activity of luciferase as a target molecule in the presence of siRNA, M0 (nM) is the siRNA concentration, and the $IC_{50}$ value is M1 (nM).
(4) Results Relative expression levels are shown in FIG. 14 and $IC_{50}$ values are shown in Table 1.

TABLE 1

| No. | siRNA | $IC_{50}$ (nM) | R |
|---|---|---|---|
| 1 | Cont. I | 0.057 ± 0.007 | 0.98 |
| 2 | Cont. II | 0.081 ± 0.011 | 0.94 |
| 3 | Cont. III | 0.062 ± 0.007 | 0.97 |
| 4 | Nucleic acid a | 0.035 ± 0.006 | 0.97 |
| 5 | Nucleic acid b | 0.029 ± 0.004 | 0.96 |
| 6 | Nucleic acid c | 0.047 ± 0.006 | 0.97 |
| 7 | Nucleic acid d | 0.024 ± 0.003 | 0.97 |
| 8 | Nucleic acid e | 0.210 ± 0.030 | 0.98 |
| 9 | Nucleic acid f | 0.037 ± 0.003 | 0.98 |
| 10 | Nucleic acid g | 0.069 ± 0.010 | 0.96 |

Mode:
$Y = M4 + (M3 - M4)/(1 + 10^{\wedge} ((LOG(M0) - LOG(M1))*M2))$
M1 = 1;
M2 = 1;
M3 = 1;
M4 = 100
n = 9

Compared with conventional siRNAs (i.e., Cont. I to Cont. III), siRNA activity was found to be enhanced by ligating hairpin-shaped DNA to siRNA. While the $IC_{50}$ values of control siRNAs were 0.057±0.007 nM (Cont. I), 0.081±0.011 nM (Cont. II), and 0.062±0.007 nM (Cont. III), the $IC_{50}$ values of siRNAs containing hairpin-shaped DNAs were 0.035±0.006 nM (nucleic acid a), 0.029±0.004 nM (nucleic acid b), 0.047±0.006 nM (nucleic acid c), and 0.024±0.003 nM (nucleic acid d). This indicates that activity of siRNA containing hairpin-shaped DNA is enhanced. When hairpin-shaped DNA was ligated to only one end of a nucleic acid, the $IC_{50}$ values were 0.037±0.003 nM (nucleic acid f) and 0.069±0.010 nM (nucleic acid g). Ligation of hairpin-shaped DNA to the end of a sense strand was particularly effective. Further, nucleic acid e resulting from substitution of hairpin-shaped DNA with RNA of a homologous sequence was found to exhibit an $IC_{50}$ value of 0.210±0.030 nM (i.e., activity was significantly lowered). Thus, a hairpin DNA structure was found to be effective. Nucleic acids b and d each comprising a stem region of hairpin-shaped DNA composed of 3 base pairs were found to have particularly high RNA interference effects.

<Example 3> Examination of siRNA Length in a Double-Stranded Nucleic Acid Fragment Region of the Nucleic Acid of the Present Invention An experiment for shortening the base length of siRNAs contained in the double-stranded nucleic acid fragment region of the nucleic acid of the present invention was carried out. Based on 25-bp nucleic acid b, the number of nucleotides was reduced to 23 (nucleic acids h and l), 21 (nucleic acids i and k), and 19 (nucleic acid j). Effects of nucleic acids for inhibiting expression were assayed in accordance with Example 2.

Figure 15:
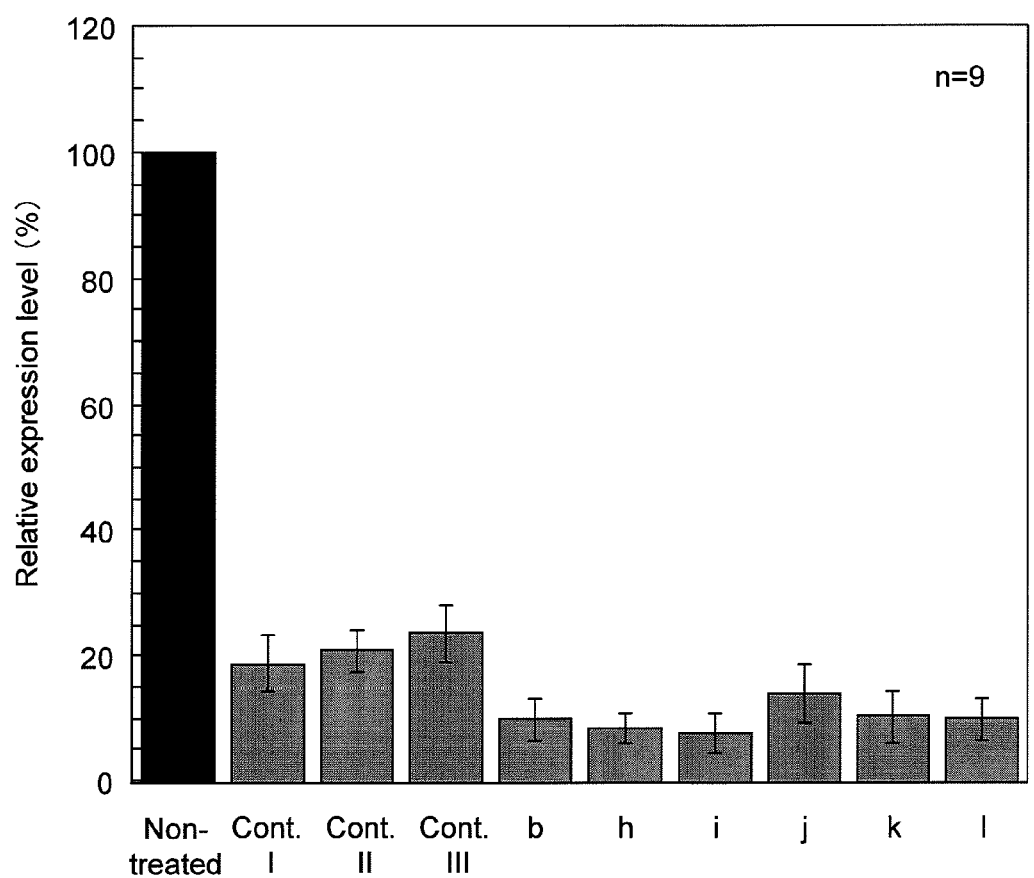
FIG. 15 shows the results of suppression of firefly luciferase expression by various nucleic acids when varying the length of the firefly luciferase siRNA contained in the double-stranded nucleic acid fragment region. As in the case of FIG. 14, the results show relative expression levels of firefly luciferase, corrected by the expression levels of *Renilla reniformis* luciferase. The relative luciferase emission obtained when samples were not treated with siRNA-containing nucleic acids (without treatment) was designated as 100%.

The results are shown in FIG. 15. When a double-stranded nucleic acid fragment region in the nucleic acid of the present invention comprised the siRNA base sequence, the nucleic acid was found to remain highly active even when the base length was reduced to about 19 nucleotides.

<Example 4> Interferon Induction by the Nucleic Acid of the Present Invention

It is known that interferon responses are induced by long double-stranded RNA and non-specific transcription is suppressed in mammalian cells or the like (Nature Cell Biol., 2003, 5 (9): 834-839, Nature Genet., 2003, 34 (3): 263-264). siRNA can avoid interferon responses by use of short double-stranded RNA and suppress specific gene expression. In order to confirm that the effects of inhibiting gene expression of Examples 2 and 3 caused by introduction of the nucleic acid of the present invention are not caused by interferon responses, whether or not interferon responses would occur upon introduction of the nucleic acid of the present invention was examined by real-time RT-PCR.

Interferon responses were confirmed by detecting expression of the human oas1 genes and the human stat1 genes, which would be induced to express by interferon responses, by RT-PCR. As a positive control for inducing interferon responses, poly (I:C) was used.

As a negative control, scrambled siRNA (TaKaRa) was used.

(1) Introduction of Various siRNAs and Plasmids into Cultured Cells

HeLa cells were seeded on a 24-well plate at $9 \times 10^4$ cells/well (700 µL) and cultured in an antibiotic-free MEM medium containing 10% fetal bovine serum for 24 hours. Transfection was carried out with the use of Lipofectamine 2000 (3.5 µL per well) by adding 350 µL of a solution prepared by mixing plasmids encoding firefly luciferase genes and plasmids encoding *Renilla reniformis* luciferase genes (1,400 ng each per well), various nucleic acids annealed in PBS (final concentration: 2.5 nM; 105 nM of scrambled siRNA in terms of nucleotides; Cont. III accounts for 125 nM, and nucleic acids b and d account for 170 nM), and poly (I:C) (TaKaRa; final concentration: 0.019 ng/µl; 58 nM in terms of nucleotides) in an OPTI-MEM medium. Induction of interferon responses was also examined in the same manner when the concentration was adjusted in terms of nucleotides (170 nM).

(2) Analysis of oas1 and stat1 Gene Expression Via RNA Extraction and Real-Time RT-PCR The cells that had been cultured for 22 hours after transfection were recovered from the plate using Sepasol RNA I super G (400 µL per well, Nacalai Tesque, Inc.) and total RNA was extracted. Further, DNA was removed by treatment with DNase I, RNA was recovered via phenol/chloroform extraction, and the RNA level was determined based on UV absorption. Real-time RT-PCR (ABI7000) was carried out using the obtained RNA as a template and the One Step SYBR PrimeScript RT-PCR kit (Perfect Real time, TaKaRa) to quantify oas1 and stat1 expression. The primer set of oas1, stat1, and β-actin (for correction of mRNA levels) primers included with the IFN Response Watcher (TaKaRa) were used.

(3) Results

Figure 16:
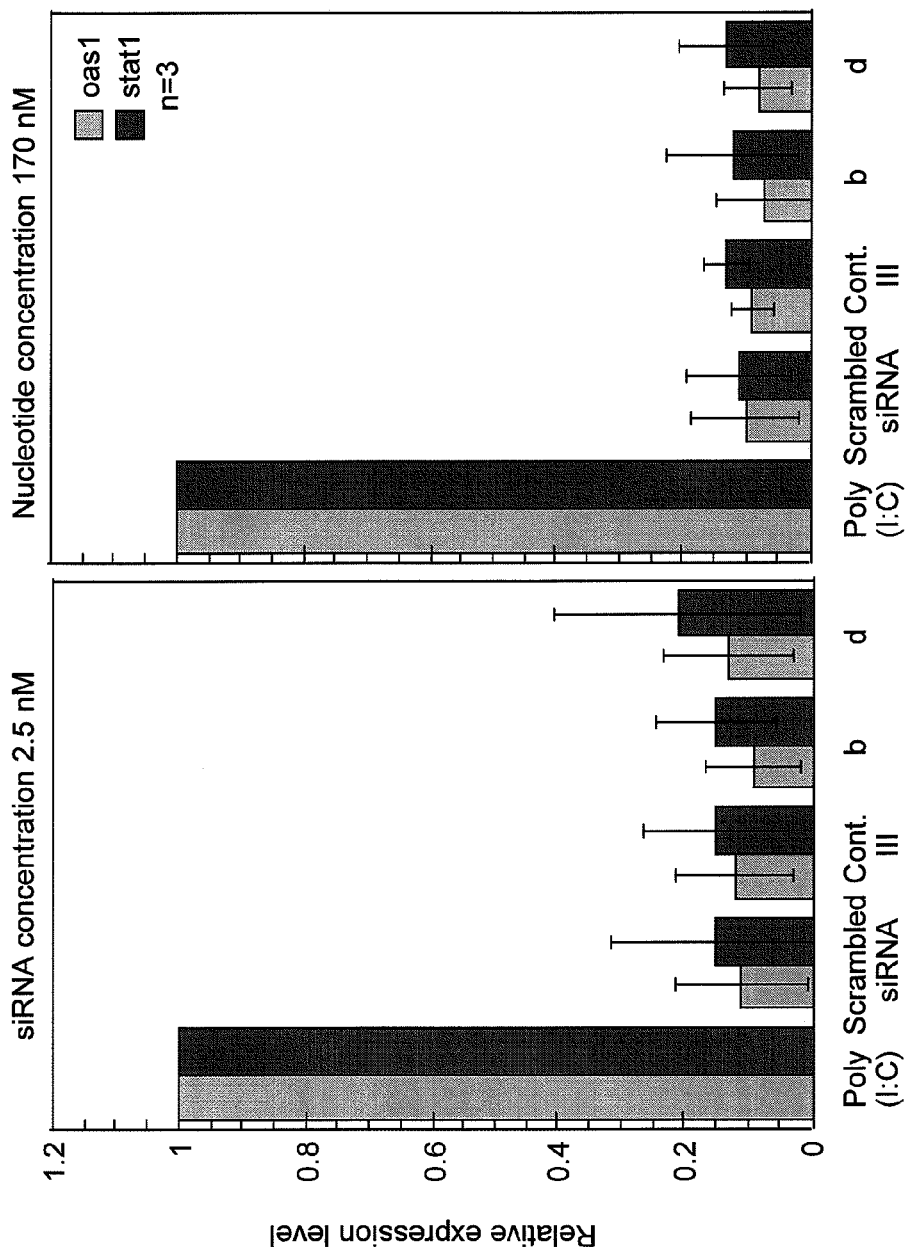
FIG. 16 shows the occurrence of interferon induction by various nucleic acids containing the nucleic acid of the present invention prepared in Example 1. oas1 and stat1 each represent a gene for which expression is induced by interferon, and Poly (I:C) represents a positive control that induces interferon responses.

The mRNA levels of the oas1 and stat1 genes were corrected based on the mRNA level of β-actin, and the obtained values were graphed and shown in FIG. 16. While introduction of poly (I/C) resulted in induction of interferon responses and elevated oas1 and stat1 expression, no significant elevation was observed in oas1 or stat1 gene expression, and mRNA levels were substantially the same when Cont. III, nucleic acid b, and nucleic acid d were introduced. This demonstrates that interferon responses are not induced with the addition of hairpin-shaped DNA to a double-stranded nucleic acid fragment comprising the siRNA base sequence.

<Example 5> Examination of Degradation Resistance to Nucleolytic Enzyme

In order to determine whether the nucleic acid of the present invention comprising, as a constituent, hairpin-shaped DNA is highly resistant to degradation by a nucleolytic enzyme, the stability of the nucleic acid of the present invention containing siRNA in snake venom phosphodiesterase (SVPD) was examined.

(1) Analysis of siRNA Stability in the Presence of SVPD

The nucleic acid b of the present invention (final concentration: 2 µM), Cont. III corresponding to the nucleic acid b without hairpin-shaped DNA (final concentration: 2 µM), were mixed with SVPD (final concentration: 0.0016 U/µl), respectively, and the resulting solution was incubated at 37° C. The solution was composed of 20 mM Tris-HCl (pH 7.8) and 15 mM $MgCl_2$. To each fractions (6 µL), separated from the mixture after 10, 20, 30, and 40 minutes, 10.6 µl of a 500 mM EDTA (pH 8.0) solution and 4 µl of 40% glycerol were mixed, and the degradation reaction was terminated. The reacted products were separated by non-denaturing 15% polyacrylamide gel electrophoresis, and the gel was stained with SYBR Green I to detect double-stranded RNA. The band pattern of the SVPD degradation product was analyzed with the use of a bio-imaging analyzer (FLA7000, Fuji Film).

(2) Results

Figure 17:
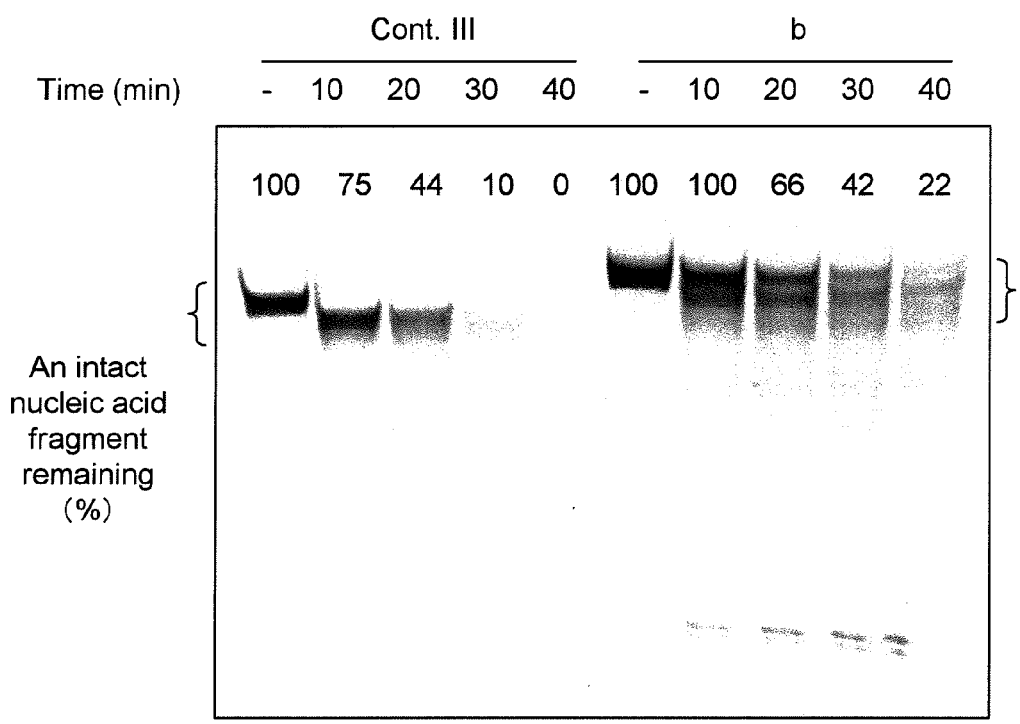
FIG. 17 shows the degradation resistance when the nucleic acid of the present invention containing siRNA is treated with a nucleolytic enzyme (i.e., snake venom phosphodiesterase (SVPD)). The percentage of an intact nucleic acid fragment remaining (%) was determined based on a band within the range shown in parentheses.

The results are shown in FIG. 17. In the case of Cont. III consisting only of a double-stranded nucleic acid fragment without hairpin-shaped DNA (i.e., double-stranded RNA), a band corresponding to a full-length fragment was not observed by treatment with SVPD after 10 minutes, all bands completely disappeared after 40 minutes, and double-stranded RNA was degraded. In contrast, the band pattern for nucleic acid b demonstrates that approximately 20% thereof still maintains the state of double-stranded RNA after 40 minutes from SVPD treatment. The results demonstrate that, in the case of the nucleic acid of the present invention in which hairpin-shaped DNA is ligated to a siRNA-containing double-stranded nucleic acid fragment, hairpin-shaped DNA imparts resistance to degradation by a nucleolytic enzyme to the double-stranded nucleic acid fragment, and the nucleic acid is stabilized.

<Example 6> Design and Preparation of the Nucleic Acid of the Present Invention Comprising a Base Sequence of Decoy DNA in the Double-Stranded Nucleic Acid Fragment Region FIG. 18 shows the secondary structures of various nucleic acids used in Examples 7 to 9 and sequences thereof. Cont. 1 is a nucleic acid consisting only of a double-stranded nucleic acid fragment comprising a consensus sequence that binds to NF-κB, Cont. 2 is conventional dumbbell-shaped decoy DNA comprising a double-stranded nucleic acid fragment comprising a consensus sequence that binds to NF-κB with both ends thereof ligated to each other with linker DNA, and Cont. 1 and Cont. 2 were used as the control samples of the nucleic acid of the present invention. A to E (hereafter, used to designate nucleic acid A to nucleic acid E) are the nucleic acids of the present invention, and they each comprise a base sequence of decoy DNA targeting the NF-κB molecule in the double-stranded nucleic acid fragment region to form a structure whereby the ends thereof are ligated to two hairpin-shaped DNAs. Nucleic acid A is a closed-circular (i.e., a dumbbell-shaped) nucleic acid, nucleic acid B is a single-stranded nucleic acid derived from nucleic acid A by introduction of a nick, and nucleic acids C and D are nucleic acids derived from nucleic acid A by shortening of the double-stranded nucleic acid fragment region and changing of the position of the nick.

Cont. 1 and nucleic acids B to D were prepared via chemical synthesis of the nucleic acids having the base sequences shown in the sequence numbers in the figures, followed by purification on 12% denaturing acrylamide gel. Nucleic acid A was prepared by subjecting nucleic acid B to intramolecular annealing while lowering the temperature from 96° C. to 16° C., adding T4 DNA ligase thereto, and incubating the resultant at 16° C. overnight to prepare a cyclic ODN molecule. Nucleic acid E was prepared by subjecting nucleic acid fragments (SEQ ID NOs: 38 and 39) to chemical synthesis, purification, mixing of equivalent amounts of fragments, and annealing while reducing the temperature from 96° C. to 16° C. Cont. 2 was prepared in the same manner as nucleic acid A with the use of a 48-mer DNA fragment (SEQ ID NO: 40).

<Example 7> Binding Activity of Decoy DNA to Target Molecule

A competitive experiment was carried out using conventional decoy DNA (i.e., Cont. 1) in order to examine binding of various nucleic acids prepared in Example 6 to NF-κB p50. Specifically, incubation was carried out by adding NF-kB p50 in the presence of Cont. 1 labeled with [γ-$^{32}$P] ATP and non-labeled nucleic acids at various concentrations (i.e., Cont. 1, Cont. 2, and nucleic acids A to E). A reaction solution (20 μL, 10 mM Tris-HCl buffer (pH 7.6), 100 mM NaCl, 2.5 mM DTT, 0.1 mM EDTA, 0.05% NP-40, and 10% glycerol) was prepared so as to contain labeled Cont. 1 (final concentration: 10 nM), competitive ODNs at various concentrations (5 to 500 nM), a double-stranded nucleic acid fragment having non-specific sequences (SEQ ID NOs: 41 and 42; final concentration: 5 μM), and NF-κB p50 (0.2 gsu, Promega), and incubation was carried out at 25° C. for 30 minutes. Thereafter, labeled Cont. 1 bound to NF-kB p50 was separated from free labeled Cont. 1 via non-denaturing 10% polyacrylamide gel electrophoresis, gel was dehydrated, and they were visualized using a bio-image analyzer to assay radioactivity. Competitive efficiency was determined in terms of the IC$_{50}$ value by performing data fitting via the least-square method with the use of the Kaleida-Graph software (Albelbeck Software) by applying the obtained value to the calculation formula: $y=M0 \times M1/(M0+M2)$. y (%) indicates protein binding efficiency, M0 (nM) indicates a concentration of non-labeled ODN as a competitor, the IC$_{50}$ value is M1 (nM), and M2(%) was determined in terms of protein binding efficiency in the absence of competitors.

Figure 19:
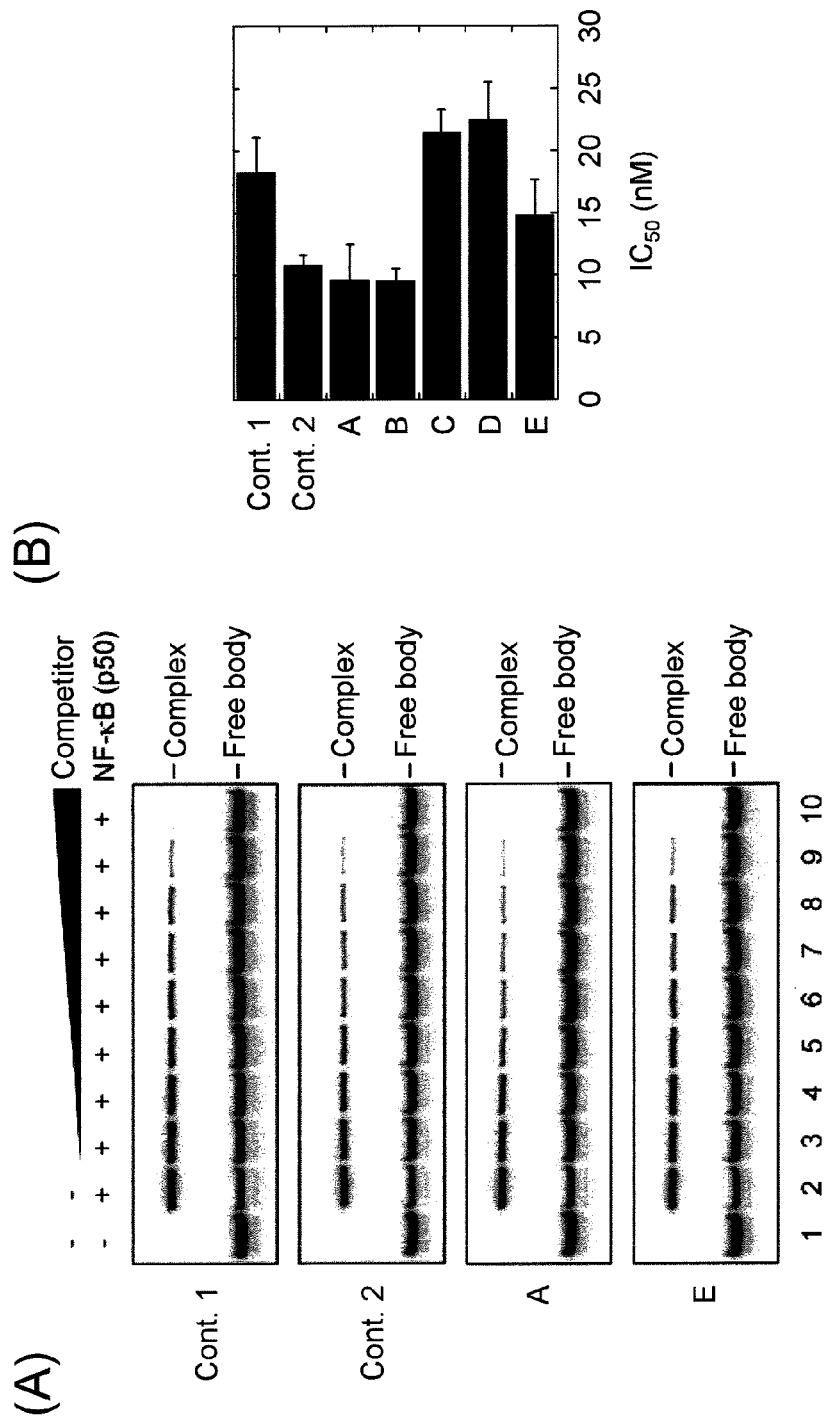
FIG. 19 shows the results of competitive experiments related to binding the various nucleic acids containing decoy DNAs recognizing NF-κB as a target molecule prepared in Example 6 to the NF-κB p50 protein. A competitor is indicated as "Cont. 1."

Some results of gel electrophoresis are shown in FIG. 19 (A) and the results of competitive efficiency assay are shown in FIG. 19 (B). Various nucleic acids were found to have substantially the same binding activity, and the binding activity was not influenced by the introduction of hairpin-shaped DNA into the 3' end of the double-stranded nucleic acid fragment.

<Example 8> Examination of Degradation Resistance to Nucleolytic Enzyme

In the same manner as in Example 5, various nucleic acids labeled with [γ-$^{32}$P]ATP of Example 6 were incubated with exonuclease III, S1 nuclease, or human serum in order to determine whether the nucleic acid of the present invention containing decoy DNA was highly resistant to degradation by nucleolytic enzymes. Exonuclease III is a nucleolytic enzyme that digests DNA from the 3' end thereof. Exonuclease is a major cause of DNA degradation that is problematic in biological applications relating to nucleic acids, such as administration thereof to organisms or cells. S1 nuclease is an endonuclease that recognizes and degrades a single-stranded nucleic acid region. The amount of nucleic acids used for the reaction is 35 pmol each. Two units of exonuclease III or one unit of S1 nuclease were added to 10 μL of the reaction solution, and incubation was carried out at 37° C. for 10 minutes or 30 minutes. Human serum was used without thermal treatment in order to maintain DNase activity. Human serum (final concentration: 50% v/v) was added to 10 μL of the reaction solution, and incubation was carried out at 37° C. for 2 hours (120 minutes) or 6 hours (360 minutes). Thereafter, a reaction-terminating buffer containing 10 M urea and 40 mM EDTA was added to an amount equivalent to the incubation product. The nucleic acids were separated via denaturing 15% polyacrylamide gel electrophoresis and then visualized with the use of a bio-image analyzer (FLA-7000, Fuji Film).

Figure 20:
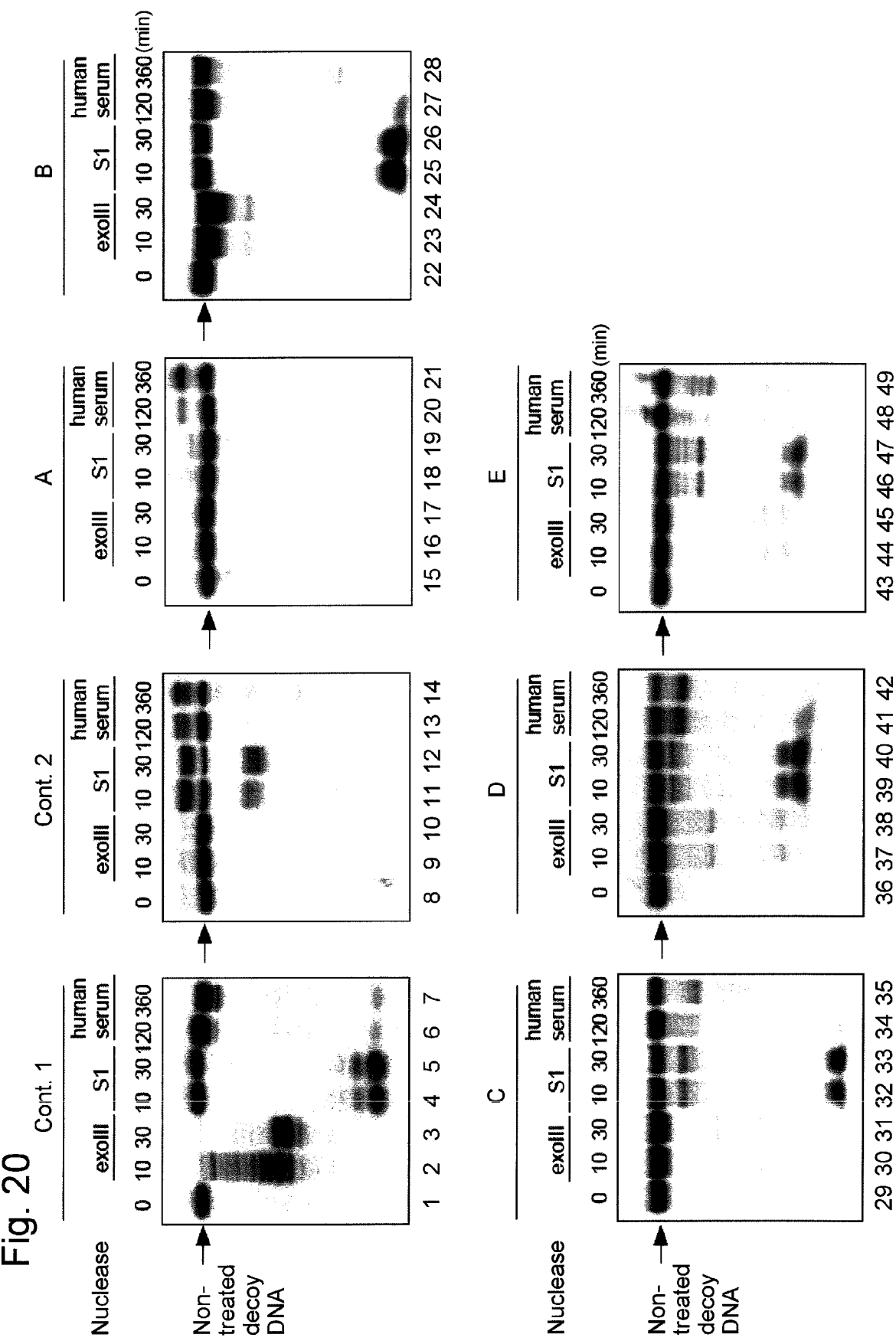
FIG. 20 shows results regarding the resistance of various nucleic acids containing decoy DNAs to degradation by nucleolytic enzymes. "exoIII" indicates exonuclease III, "S1" indicates S1 nuclease, and "human serum" indicates human serum.

The results are shown in FIG. 20. Nucleic acid A was very stable against nucleolytic enzymes, and it was not substantially degraded after being incubated for 30 minutes (lanes 17 and 19). In contrast, Cont. 2 having a loop structure made by known linker DNA was found to be stable against exonuclease III (lane 10), but it was significantly degraded by S1 nuclease (lanes 11 and 12). A degradation product is observed at a position exhibiting a lower degree of mobility than untreated decoy DNA in an electrophoretic pattern because the sequence is single-stranded upon introduction of a nick into cyclic DNA by S1 nuclease. Thereafter, significant degradation proceeds. Based on the pattern of the degradation product, human serum was found to contain single-strand-specific endonuclease (lanes 13, 14, 20, and 21). Cyclic DNA having a hairpin shape was found to have higher resistance than cyclic DNA having a loop structure in such a case. In addition, stability against an exonuclease was found to be significantly enhanced with the addition of hairpin-shaped DNA to the 3' end.

FIG. 21(A) and FIG. 21(B) show the results of analysis of S1 nuclease treatment and human serum treatment, respectively, with the elapse of time. FIG. 21 shows a graph showing the results of quantification of the results of gel electrophoresis of the treatments with the elapse of time. Compared with Cont. 2, nucleic acid A, nucleic acid B, and nucleic acid E of the present invention have apparently enhanced degradation resistance to the endonuclease. While Cont. 2 in a closed-circular state is substantially degraded by S1 nuclease after being incubated for 1 hour, 80% or more of the nucleic acids A and B of the present invention remained undegraded. Even though nucleic acid B is a cleaved and single-stranded nucleic acid containing a nick, in particular, it is more stable than closed-circular DNA (i.e., Cont. 2). In addition, the nucleic acids A and B of the present invention were found to be more stable against S1 nuclease than Cont. 2 in human serum. Nucleic acid A was found to maintain a nick even after 24 hours of treatment in human serum.

<Example 9> Examination of Correlation Between Binding Site of Hairpin-Shaped DNA and Inhibitory Effexts of siRNA on Firefly Luciferase Gene Expression A nucleic acid comprising hairpin-shaped DNA ligated to an end of conventional siRNA (i.e., Cont. III) shown in FIG. 12 was prepared, and differences in the binding sites and inhibitory effects of such nucleic acids on target gene expression were examined.

Figure 22:
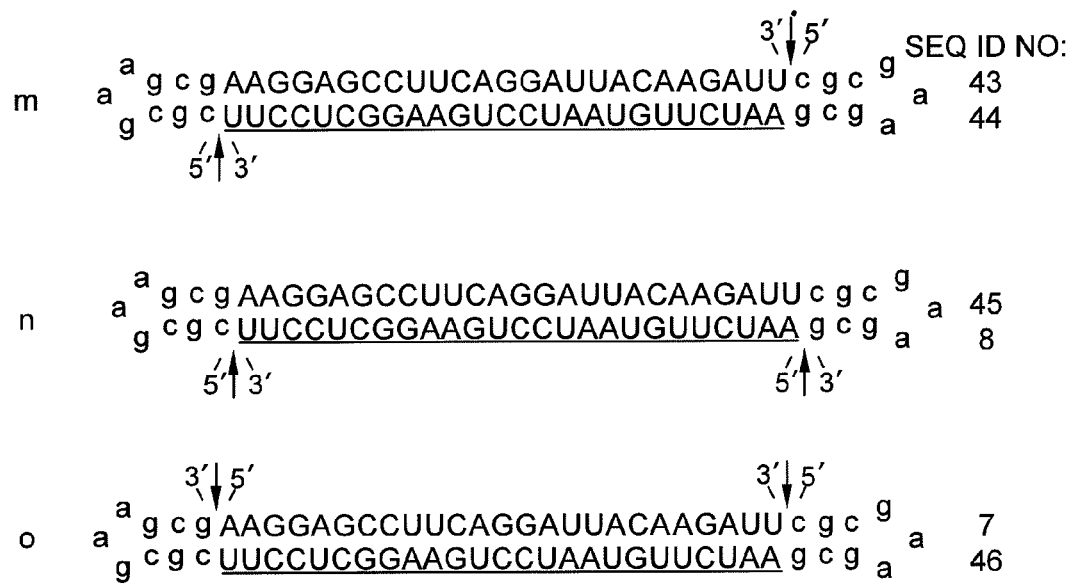
FIG. 22 shows sequences and structures of various nucleic acids containing siRNA targeting the firefly luciferase gene. An arrow indicates a non-ligated region (a nick region). In the sequences, DNAs are represented by lower-case letters and RNAs are represented by upper-case letters. An underlined sequence represents an siRNA antisense strand (a guide strand).

FIG. 22 schematically shows constitutions of nucleic acids used in this example. Nucleic acid m comprises hairpin-shaped DNAs ligated to the 5' ends of the sense strand and of the antisense strand of Cont. III. Nucleic acid n comprises hairpin-shaped DNAs ligated to the 5' end and the 3' end of the sense strand of Cont. III. Nucleic acid o comprises hairpin-shaped DNAs ligated to the 5' end and the 3' end of the antisense strand of Cont. III. In FIG. 22, siRNA antisense strands of all nucleic acids are underlined.

Various nucleic acids were synthesized and prepared in accordance with Example 1. Double-stranded nucleic acid fragments were prepared to a final concentration of 0.1 nM. As control siRNAs, Cont. III (a nucleic acid consisting of siRNA without a mini hairpin) and nucleic acid b shown in FIG. 12 (a nucleic acid comprising hairpin-shaped DNAs ligated to the 3' ends of the sense strand and the antisense strand of Cont. III) were used. Inhibitory effects of various nucleic acids on firefly luciferase gene expression were assayed in accordance with the method described in Example 2.

Figure 23:
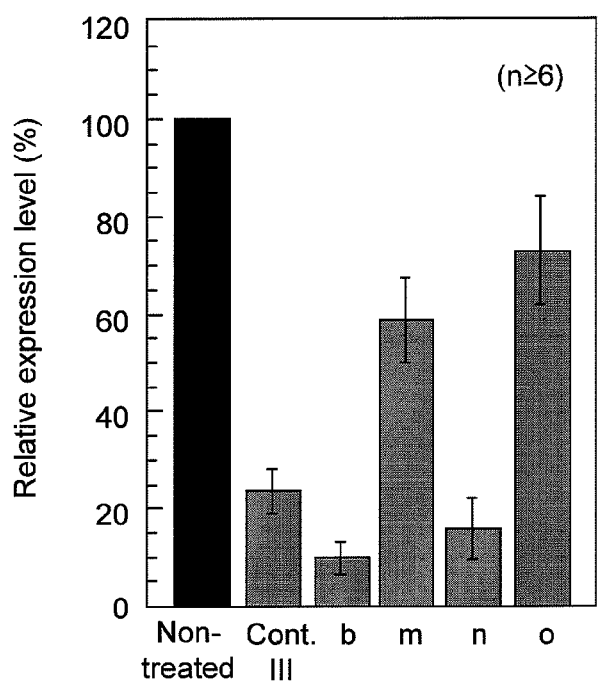
FIG. 23 shows the results of suppression of firefly luciferase expression by various nucleic acids containing firefly luciferase siRNA in HeLa cells. The results show relative expression levels of firefly luciferase, corrected by the expression levels of *Renilla reniformis* luciferase. The relative luciferase emission obtained when samples were not treated with siRNA-containing nucleic acids (without treatment) was designated as 100%.

The results are shown in FIG. 23. While the inhibitory effects of nucleic acid m and nucleic acid o were lowered, nucleic acid n was found to have inhibitory effects similar to those of nucleic acid b. The results demonstrate that inhibitory effects on target gene expression are attenuated when hairpin-shaped DNA is ligated to the 5' end of the siRNA antisense strand. Accordingly, siRNA may be designed to comprise hairpin-shaped DNAs ligated to both the 5' end and the 3' end of the sense strand, as with nucleic acid n, so that effects of allowing only one strand of conventional siRNA to selectively function as an antisense strand can further be imparted.

<Example 10> Examination of Sustainability of Inhibitory Effects on Firefly Luciferase Gene Expression In Example 10, sustainability of inhibitory effects of the nucleic acid of the present invention on gene expression was examined.

Specifically, Cont. III and nucleic acid b shown in FIG. 12 were prepared to a final concentration of 0.1 nM in accordance with the method of Example 1, and the resultants were introduced into HeLa cells via lipofection with plasmids encoding the target molecules (i.e., firefly luciferase genes) in accordance with the method of Example 2. The medium was exchanged with fresh medium 6 hours after transfection, and siRNA that had not been introduced was removed by washing. The sustainability of inhibitory effects on gene expression was examined by assaying luciferase emission intensities 1, 2, 3, 4, and 5 days after transfection and determining relative expression levels. The medium was exchanged with fresh medium again 3 days after transfection for the purpose of cell maintenance.

Figure 24:
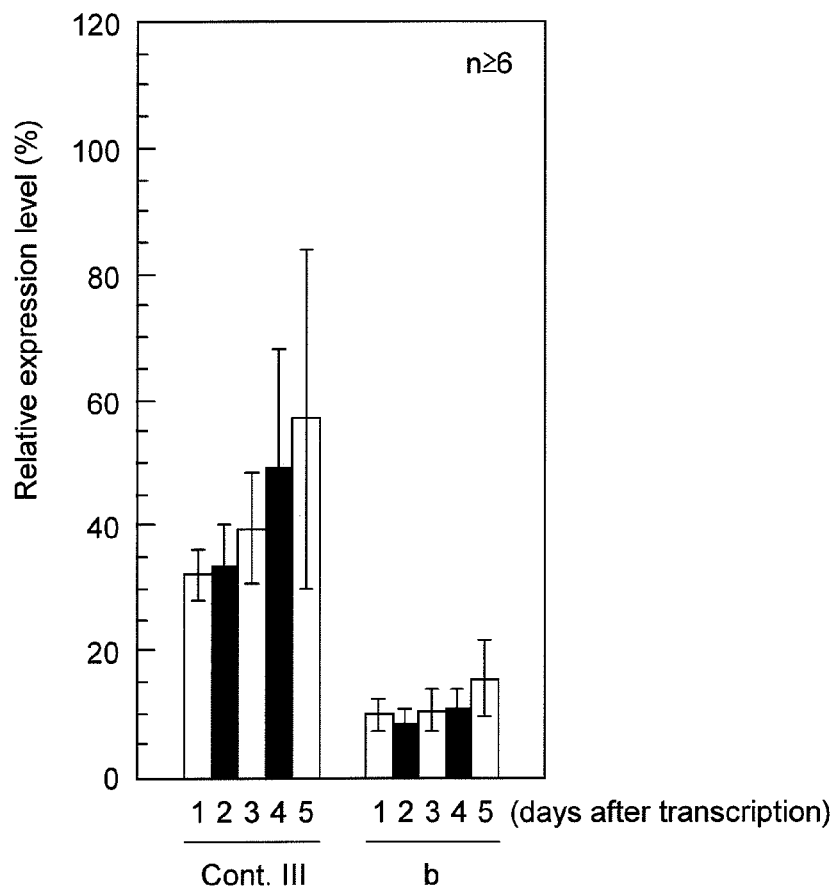
FIG. 24 shows the sustainability of the effects of suppression of firefly luciferase expression by various nucleic acids containing firefly luciferase siRNAs in HeLa cells.

The results are shown in FIG. 24. Cont. III exhibited an elevated relative luciferase expression level after transfection with the elapse of time. This indicates that sustainability of inhibitory effects on gene expression is poor. However, nucleic acid b did not exhibit significant changes in relative expression level 5 days after transfection. This indicates that the sustainability of inhibitory effects on gene expression is sufficient. The results demonstrate that the nucleic acid of the present invention is capable of maintaining effects of inhibiting expression of the target luciferase gene for a longer period of time than a double-stranded nucleic acid fragment without hairpin-shaped DNA.

<Example 11> Examination of RNAi Effects of the Nucleic Acid of the Present Invention on Endogenous Gene (1)

In Example 11, RNAi effects on the endogenous survivin gene of HeLa cells on mRNA were examined.
(1) Preparation of Various Nucleic Acids FIG. 25 schematically shows structures of the nucleic acids used in Example 11. Synthesis of nucleic acid fragments constituting Cont. IV and nucleic acid p was entrusted to Hokkaido System Science Co., Ltd. (Hokkaido, Japan). Double-stranded nucleic acid fragments were prepared by subjecting the synthesized nucleic acid fragments after desalting to gel filtration, mixing base-paired nucleic acid fragments in a phosphate buffer (pH 7.4) to adjust the concentration to the same level, heating the resultant at 90° C., and gradually cooling down the resultant to 25° C. for annealing. Synthesis of nucleic acid fragments constituting Cont. V was entrusted to Gene Design Inc. (Osaka, Japan). Double-stranded nucleic acid fragments were prepared by obtaining the simple column purification grade using a reverse-phase cartridge in the form of a double-stranded fragment and annealing the resultant in a phosphate buffer (pH 7.4) in the same manner.
(2) Introduction of Various Nucleic Acids into Cultured Cells HeLa cells were seeded on a 6-well plate at $3 \times 10^5$ cells/well and cultured in 2 mL of an antibiotic-free MEM medium containing 10% fetal bovine serum for 24 hours. Transfection was carried out with the use of 5 µL of Lipofectamine 2000 per well by adding 400 µL of a solution prepared so as to contain various nucleic acids that had been annealed in PBS at final concentrations of 0.02 to 2 nM adjusted with OPTI-MEM medium (Invitrogen) per well. The medium was exchanged with 2 mL of a fresh antibiotic-free MEM medium containing 10% fetal bovine serum 6 hours after transfection, and siRNA that had not been introduced was removed by washing.
(3) Analysis of mRNA Expression Level In order to quantify survivin mRNA remaining in cells, mRNA was recovered from the cells that had been subjected to transfection, and the survivin mRNA expression level was assayed by real-time RT-PCR.

Specifically, cells that had been cultured for 24 hours after transfection were treated with a lysis buffer (100 mM Tris-HCl (pH 7.5), 500 mM LiCl, 10 mM EDTA, 1% LiDS, and 5 mM DTT), and mRNA was then extracted from the cytolytic product using Dynabeads Oligo (dT)25 (Invitrogen) in accordance with the included instructions.

The resulting mRNA (200 ng) was reversetranscribed with the use of M-MLV Reverse Transcriptase RNase H (-) (Promega) and an oligo dT primer (15mer) to prepare cDNA, and real-time PCR was carried out using the resulting cDNA as a template. Real-time PCR was performed with the use of the KAPA SYBR FAST qPCR Kit (Kapa Biosystems) as a reagent and Mx3005P (Stratagene) as a real-time PCR apparatus. The base sequences of primers used for detecting human survivin mRNA are shown in SEQ ID NO: 61 (forward primer) and SEQ ID NO: 62 (reverse primer). Human β-actin mRNA was used as a control for mRNA level correction. SEQ ID NO: 63 shows the base sequence of the forward primer used for detection and SEQ ID NO: 64 shows that of the reverse primer.

PCR was carried out via 40 cycles of denaturation at 95° C. for 30 seconds, followed by 95° C. for 5 seconds and 60° C. for 40 seconds. After the survivin mRNA expression level was normalized using the β-actin mRNA expression level for correction, the relative expression level of survivin mRNA was determined by designating the value attained in the absence of nucleic acids (i.e., when transfected only with PBS) to be 100%. Also, the relative expression levels of survivin mRNA in the presence of siRNAs at various different concentrations were determined, and the $IC_{50}$ values were obtained based on a graph plotting relative expression levels in relation to concentrations. Specifically, the value of interest was determined with the use of Kaleida-Graph by applying the obtained value to the following calculation formula: $Y=M*100/(M_0+M_1)$ [default value: $M_1=0.01$] via data fitting using the least-square method. Y (%) is the relative expression level of survivin mRNA in the presence of siRNA, $M_0$ (nM) is the siRNA concentration, and the $IC_{50}$ value is $M_1$ (nM).
(4) Results The determined $IC_{50}$ values are shown in Table 2.

TABLE 2

| No. | siRNA | $IC_{50}$ (nM) | R |
|---|---|---|---|
| 1 | Cont. IV | 0.169 ± 0.024 | 0.97 |
| 2 | Cont. V | 0.175 ± 0.019 | 0.98 |
| 3 | Nucleic acid p | 0.071 ± 0.009 | 0.95 |

Mode:
Y = M1*100/(M0 + M1) (M1 = 0.01; n ≥ 3)

The results demonstrate that nucleic acid p has higher siRNA activity than conventional siRNA (i.e., Cont. IV or Cont. V), even when the endogenous survivin gene is the target.

<Example 12> Examination of Degradation Resistance of Various Nucleic Acids in Serum The stability of various nucleic acids used in Example 11 in the presence of the nuclease-containing serum was examined.

The basic technique was in accordance with the method described in Example 5. Specifically, various siRNAs adjusted to a final concentration of 1.25 μM were mixed with mouse serum (final concentration: 20%). The mixture was incubated at 37° C., 6 μL of fractions were separated therefrom 1 hour, 8 hours, and 24 hours thereafter, and the separated fractions were mixed with 10 μL of a stop solution (100 mM EDTA and 8 M urea). Subsequently, the resultant was thermally treated at 75° C. for 3 minutes, a 10-μL fraction was separated therefrom via electrophoresis on 15% polyacrylamide gel-7 M urea, and a band pattern was detected via SYBR Green II staining.

Figure 26:
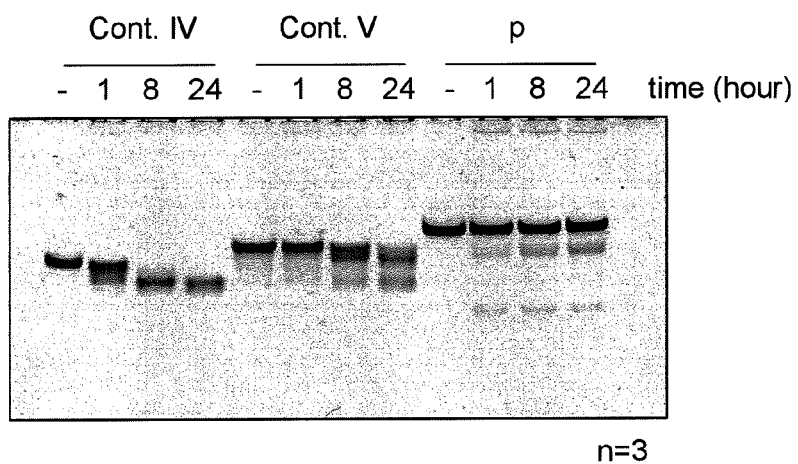
FIG. 26 shows degradation resistance when various nucleic acids shown in FIG. 25 are treated with mouse serum. In the figure, the (-) symbol indicates a band of various nucleic acids that were not treated with mouse serum.

The results are shown in FIG. 26. The size of a band of Cont. IV or Cont. V without hairpin-shaped DNA was reduced due to degradation by a nuclease with the elapse of time, and a band corresponding to a full-length fragment was not observed at all 8 hours later. In contrast, a full-length band of nucleic acid p was clearly observed 24 hours later, and the amount thereof was not significantly reduced. The results demonstrate that the nucleic acid of the present invention is stabilized in the serum.

<Example 13> Examination of Sustainability of RNAi Effects in the Nucleic Acid of the Present Invention on Endogenous Gene Sustainability of RNAi effects of various double-stranded nucleic acid fragments used in Example 11 (Cont. IV, Cont. V, and nucleic acid p) on mRNA of the survivin gene was examined.

The final concentrations of the various nucleic acids were adjusted to 0.1 nM and the nucleic acids were introduced into HeLa cells by lipofection. The medium was then exchanged with fresh medium 6 hours after transfection, the survivin mRNA expression levels were assayed 1 day, 2 days, and 3 days after transfection. The specific technique was in accordance with the method described in Example 11.

Figure 27:
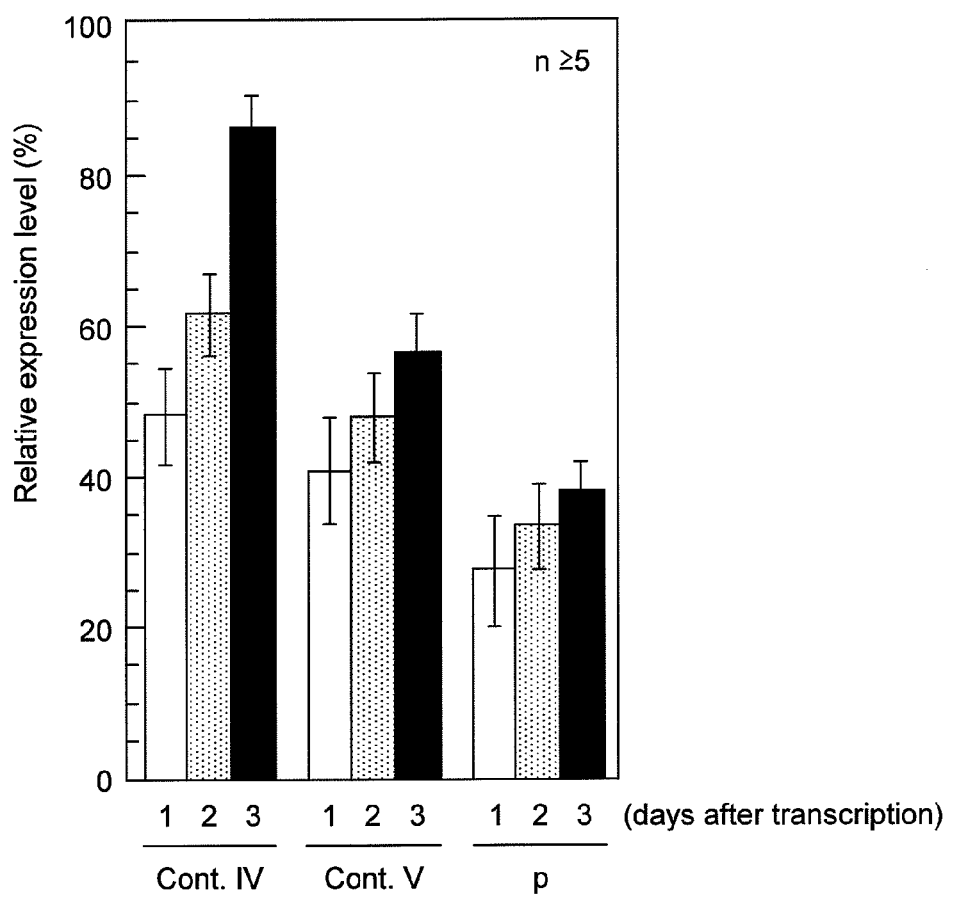
FIG. 27 shows the sustainability of the effects of suppression of survivin gene expression by survivin siRNA and the nucleic acid p of the present invention containing the same in HeLa cells.

The results are shown in FIG. 27. Compared with Cont. IV or Cont. V without hairpin-shaped DNA, nucleic acid p exhibited higher inhibitory effects on survivin mRNA expression 3 days after transfection. The results demonstrate a higher degree of sustainability of RNAi effects of the nucleic acid of the present invention than in the case of Cont. IV or Cont. V.

<Example 14> Examination of RNAi Effects in the Nucleic Acid of the Present Invention on Endogenous Gene (2)

In Example 14, RNAi effects on the LaminA/C gene, which is the endogenous gene other than the survivin gene in the HeLa cells, on mRNA were examined.
(1) Preparation of Various Nucleic Acids FIG. 28 schematically shows structures of nucleic acids used in Example 14. Nucleic acid q comprises a base sequence derived from the base sequence of conventional siRNA (i.e., Cont. VI) by substitution of a two thymine residues overhang in the 3' terminal region with hairpin-shaped DNA. Nucleic acid r comprises a base sequence derived from the base sequence of conventional siRNA (i.e., Cont. VII) by addition of hairpin-shaped DNA to a 3' terminal region. Synthesis of nucleic acid fragments constituting various nucleic acids was entrusted to Gene Design Inc. (Osaka, Japan). Synthetic nucleic acid fragments were mixed with base-paired nucleic acid fragments after HPLC purification in a phosphate buffer (pH 7.4) to adjust the concentrations to the same level, and the resultant was heated to 90° C. and gradually cooled to 25° C. for annealing.
(2) Introduction of Various Double-Stranded Nucleic Acids into Culture Cells The basic technique used was in accordance with the method described in Example 11. Various nucleic acids were introduced into HeLa cells by lipofection to a final concentration of 0.1 nM.

(3) Analysis of mRNA Expression Level

In order to quantify LaminA/C mRNA remaining in cells, mRNA was recovered from the cells that had been subjected to transfection, and the LaminA/C mRNA expression level was assayed by real-time RT-PCR.

The specific technique used was in accordance with the method described in Example 11. The base sequences of primers used for detecting human LaminA/C mRNA are shown in SEQ ID NO: 65 (forward primer) and SEQ ID NO: 66 (reverse primer). Human GAPDH mRNA was used as a control for mRNA level correction. SEQ ID NO: 67 shows the base sequence of the forward primer used for detection and SEQ ID NO: 68 shows that of the reverse primer.

Figure 29:
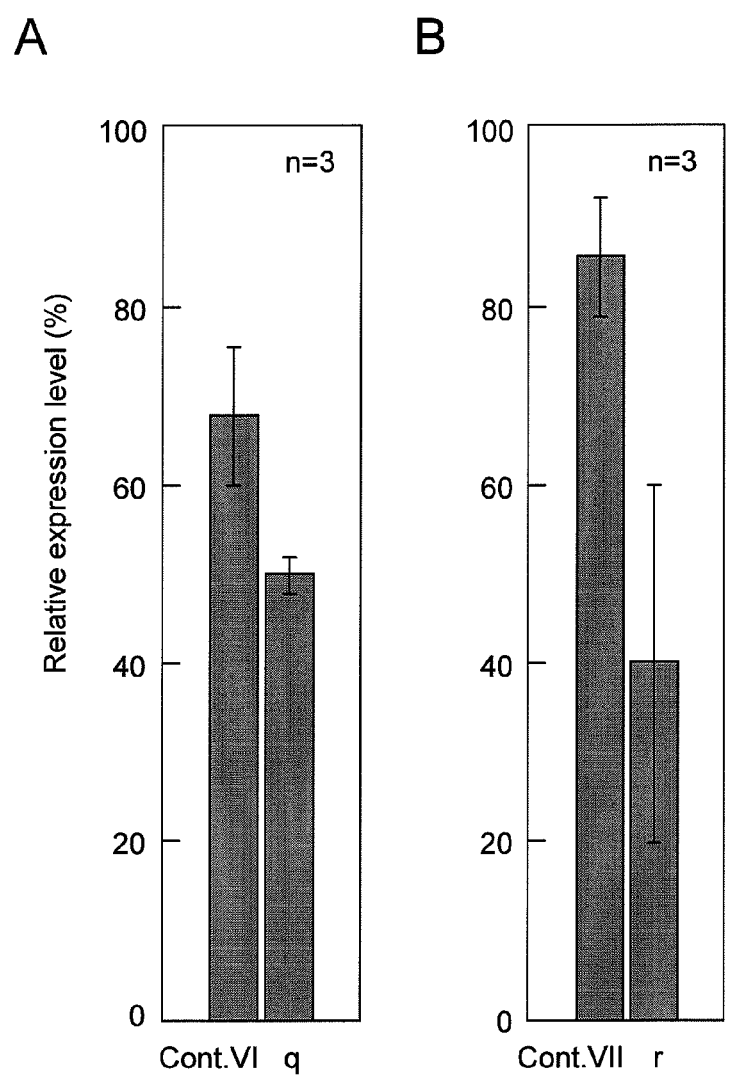
FIG. 29 shows the results of suppression of human Lamin A/C gene expression in an HeLa cell treated with various nucleic acids shown in FIG. 28.

The results are shown in FIG. 29. Even when LaminA/C was the target, the nucleic acid q or r of the present invention had a higher degree of siRNA activity than conventional siRNA (i.e., Cont. VI or Cont. VII). The results attained in Example 14 and Example 11 demonstrate that the nucleic acid of the present invention is capable of inhibiting expression of a variety of endogenous genes, regardless of target gene type.

All publications, patents, and patent applications cited herein are incorporated herein by reference in their entirety.

---

The invention claimed is:

1. A nucleic acid comprising:

a hairpin-shaped DNA comprising nucleic acid regions (A) to (C) below sequentially ligated from the 5' end toward the 3' end:

(A) a first nucleic acid region comprising 2 to 5 arbitrary nucleotides;

(B) a second nucleic acid region comprising a "gna" or "gnna" base sequence, wherein each "n" independently represents "g", "t", "a", or "c", a base analogue, or a modified base; and (C) a third nucleic acid region comprising a base sequence complementary to the first nucleic acid region, wherein the first nucleic acid region and the third nucleic acid region form a stem portion by base pairing with each other and the second nucleic acid region forms a loop portion, and a single-stranded nucleic acid fragment comprising a DNA aptamer;

wherein at least one end of the nucleic acid fragment is ligated to the hairpin-shaped DNA.

2. The nucleic acid according to claim 1, wherein the first nucleic acid region comprises "g" or "c" base.

3. The nucleic acid according to claim 1, wherein, when the nucleic acid fragment is the single-stranded nucleic acid fragment (1), at least one stem structure formed via intramolecular annealing of the single-stranded nucleic acid fragment has a mismatched region or bulge structure.

4. The nucleic acid according to claim 1, wherein the hairpin-shaped DNA is ligated to either the 5' or 3' end of the single-stranded nucleic acid fragment.

5. A pharmaceutical composition comprising, as an active ingredient, the nucleic acid according to claim 1.

6. The pharmaceutical composition according to claim 5, which comprises a pharmaceutically acceptable carrier.

7. A method for enhancing resistance of a nucleic acid fragment to degradation by a nucleolytic enzyme by ligating hairpin-shaped DNA comprising the nucleic acid regions (A) to (C) below sequentially ligated from the 5' end toward the 3' end:

(A) a first nucleic acid region comprising 2 to 5 arbitrary nucleotides;

(B) a second nucleic acid region comprising a "gna" or "gnna" base sequence, wherein each "n" independently represents "g", "t", "a", or "c", a base analogue, or a modified base; and (C) a third nucleic acid region comprising a base sequence complementary to the first nucleic acid region, wherein the first nucleic acid region and the third nucleic acid region form a stem portion by base pairing with each other and the second nucleic acid region forms a loop portion, to a single-stranded nucleic acid fragment comprising a DNA aptamer; wherein at least one end of the nucleic acid fragment is ligated to the hairpin-shaped DNA.

8. The method according to claim 7, wherein the first nucleic acid region comprises "g" or "c" base.

* * * * *

SEQUENCE LISTING

```
<160> NUMBER OF SEQ ID NOS: 68

<210> SEQ ID NO 1
<211> LENGTH: 7
<212> TYPE: DNA
<213> ORGANISM: Artificial Sequence
<220> FEATURE:
<223> OTHER INFORMATION: mini-hairpin

<400> SEQUENCE: 1 gcgaagc                                                                  7

<210> SEQ ID NO 2
<211> LENGTH: 10
<212> TYPE: DNA
<213> ORGANISM: Artificial Sequence
<220> FEATURE:
<223> OTHER INFORMATION: mini-hairpin

<400> SEQUENCE: 2
cgcgaaagcg                                                              10

<210> SEQ ID NO 3
<211> LENGTH: 21
<212> TYPE: RNA
<213> ORGANISM: Artificial Sequence
<220> FEATURE:
<223> OTHER INFORMATION: Photinus pyralis luciferase siRNA

<400> SEQUENCE: 3
ggagccuuca ggauuacaag a                                                 21

<210> SEQ ID NO 4
<211> LENGTH: 21
<212> TYPE: RNA
<213> ORGANISM: Artificial Sequence
<220> FEATURE:
<223> OTHER INFORMATION: Photinus pyralis luciferase siRNA

<400> SEQUENCE: 4
uuguaauccu gaaggcuccu u                                                 21

<210> SEQ ID NO 5
<211> LENGTH: 21
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 5
ggagccuuca ggauuacaat t                                                 21
```

<210> SEQ ID NO 6
<211> LENGTH: 21
<212> TYPE: DNA
<213> ORGANISM: Artificial Sequence
<220> FEATURE:
<223> OTHER INFORMATION: Combined DNA/RNA: Photinus pyralis luciferase
    siRNA

<400> SEQUENCE: 6
uuguaauccu gaaggcucct t                                              21

<210> SEQ ID NO 7
<211> LENGTH: 25
<212> TYPE: RNA
<213> ORGANISM: Artificial Sequence
<220> FEATURE:
<223> OTHER INFORMATION: Photinus pyralis luciferase siRNA

<400> SEQUENCE: 7
aaggagccuu caggauuaca agauu                                          25

<210> SEQ ID NO 8
<211> LENGTH: 25
<212> TYPE: RNA
<213> ORGANISM: Artificial Sequence
<220> FEATURE:
<223> OTHER INFORMATION: Photinus pyralis luciferase siRNA

<400> SEQUENCE: 8
aaucuuguaa uccgaaggc uccuu                                           25

<210> SEQ ID NO 9
<211> LENGTH: 32
<212> TYPE: DNA
<213> ORGANISM: Artificial Sequence
<220> FEATURE:
<223> OTHER INFORMATION: Combined DNA/RNA: Photinus pyralis luciferase
    siRNA

<400> SEQUENCE: 9
aaggagccuu caggauuaca agauugcgaa gc                                  32

<210> SEQ ID NO 10
<211> LENGTH: 32
<212> TYPE: DNA
<213> ORGANISM: Artificial Sequence
<220> FEATURE:
<223> OTHER INFORMATION: Combined DNA/RNA: Photinus pyralis luciferase
    siRNA

<400> SEQUENCE: 10
aaucuuguaa uccgaaggc uccuugcgaa gc                                   32

<210> SEQ ID NO 11
<211> LENGTH: 34
<212> TYPE: DNA
<213> ORGANISM: Artificial Sequence
<220> FEATURE:
<223> OTHER INFORMATION: Combined DNA/RNA: Photinus pyralis luciferase
    siRNA

<400> SEQUENCE: 11
aaggagccuu caggauuaca agauucgcga agcg                                34

<210> SEQ ID NO 12
<211> LENGTH: 34

```
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 12
aaucuuguaa uccugaaggc uccuucgcga agcg                                34

<210> SEQ ID NO 13
<211> LENGTH: 35
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 13
aaggagccuu caggauuaca agauucgcga aagcg                               35

<210> SEQ ID NO 14
<211> LENGTH: 35
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 14
aaucuuguaa uccugaaggc uccuucgcga aagcg                               35

<210> SEQ ID NO 15
<211> LENGTH: 34
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 15
aaggagccuu caggauuaca agauucgcgt agcg                                34

<210> SEQ ID NO 16
<211> LENGTH: 34
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 16
aaucuuguaa uccugaaggc uccuucgcgt agcg                                34

<210> SEQ ID NO 17
<211> LENGTH: 32
<212> TYPE: RNA
<213> ORGANISM: Artificial Sequence
<220> FEATURE:
<223> OTHER INFORMATION: Photinus pyralis luciferase siRNA

<400> SEQUENCE: 17
aaggagccuu caggauuaca agauugcgaa gc                                  32

<210> SEQ ID NO 18
<211> LENGTH: 32
<212> TYPE: RNA
<213> ORGANISM: Artificial Sequence
```

```
<220> FEATURE:
<223> OTHER INFORMATION: Photinus pyralis luciferase siRNA

<400> SEQUENCE: 18
aaucuuguaa uccugaaggc uccuugcgaa gc                                         32

<210> SEQ ID NO 19
<211> LENGTH: 34
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 19
aaggagccuu caggauuaca agauucgcga agcg                                       34

<210> SEQ ID NO 20
<211> LENGTH: 25
<212> TYPE: RNA
<213> ORGANISM: Artificial Sequence
<220> FEATURE:
<223> OTHER INFORMATION: Photinus pyralis luciferase siRNA

<400> SEQUENCE: 20
aaucuuguaa uccugaaggc uccuu                                                 25

<210> SEQ ID NO 21
<211> LENGTH: 25
<212> TYPE: RNA
<213> ORGANISM: Artificial Sequence
<220> FEATURE:
<223> OTHER INFORMATION: Photinus pyralis luciferase siRNA

<400> SEQUENCE: 21
aaggagccuu caggauuaca agauu                                                 25

<210> SEQ ID NO 22
<211> LENGTH: 34
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 22
aaucuuguaa uccugaaggc uccuucgcga agcg                                       34

<210> SEQ ID NO 23
<211> LENGTH: 32
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 23
ggagccuuca ggauuacaag auucgcgaag cg                                         32

<210> SEQ ID NO 24
<211> LENGTH: 32
<212> TYPE: DNA
<213> ORGANISM: Artificial Sequence
<220> FEATURE:
<223> OTHER INFORMATION: Combined DNA/RNA: Photinus pyralis luciferase
      siRNA
```

```
<400> SEQUENCE: 24
aaucuuguaa uccugaaggc ucccgcgaag cg                                      32

<210> SEQ ID NO 25
<211> LENGTH: 30
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 25
ggagccuuca ggauuacaag acgcgaagcg                                        30

<210> SEQ ID NO 26
<211> LENGTH: 30
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 26
ucuuguaauc cugaaggcuc ccgcgaagcg                                        30

<210> SEQ ID NO 27
<211> LENGTH: 28
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 27
ggagccuuca ggauuacaac gcgaagcg                                          28

<210> SEQ ID NO 28
<211> LENGTH: 28
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 28
uuguaauccu gaaggcuccc gcgaagcg                                          28

<210> SEQ ID NO 29
<211> LENGTH: 30
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 29
aaggagccuu caggauuaca acgcgaagcg                                        30

<210> SEQ ID NO 30
<211> LENGTH: 30
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 30
```
uuguaauccu gaaggcuccu ucgcgaagcg                                       30

<210> SEQ ID NO 31
<211> LENGTH: 32
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 31
aaggagccuu caggauuaca agacgcgaag cg                                     32

<210> SEQ ID NO 32
<211> LENGTH: 32
<212> TYPE: DNA
<213> ORGANISM: Artificial Sequence
<220> FEATURE:
<223> OTHER INFORMATION: Combined DNA/RNA: Photinus pyralis luciferase
      siRNA

<400> SEQUENCE: 32
ucuuguaauc cugaaggcuc cuucgcgaag cg                                     32

<210> SEQ ID NO 33
<211> LENGTH: 20
<212> TYPE: DNA
<213> ORGANISM: Artificial Sequence
<220> FEATURE:
<223> OTHER INFORMATION: human NF-kB decoy DNA

<400> SEQUENCE: 33
ccttgaaggg atttccctcc                                                   20

<210> SEQ ID NO 34
<211> LENGTH: 20
<212> TYPE: DNA
<213> ORGANISM: Artificial Sequence
<220> FEATURE:
<223> OTHER INFORMATION: human NF-kB decoy DNA

<400> SEQUENCE: 34
ggagggaaat cccttcaagg                                                   20

<210> SEQ ID NO 35
<211> LENGTH: 46
<212> TYPE: DNA
<213> ORGANISM: Artificial Sequence
<220> FEATURE:
<223> OTHER INFORMATION: human NF-kB decoy DNA

<400> SEQUENCE: 35
tcaagcgaag cttgaaggga tttccctgcg aagcagggaa atccct                      46

<210> SEQ ID NO 36
<211> LENGTH: 40
<212> TYPE: DNA
<213> ORGANISM: Artificial Sequence
<220> FEATURE:
<223> OTHER INFORMATION: human NF-kB decoy DNA

<400> SEQUENCE: 36
aagggatttc cctgcgaagc agggaaatcc cttgcgaagc                             40

<210> SEQ ID NO 37

```
<211> LENGTH: 34
<212> TYPE: DNA
<213> ORGANISM: Artificial Sequence
<220> FEATURE:
<223> OTHER INFORMATION: human NF-kB decoy DNA

<400> SEQUENCE: 37
gggaaatccc gcgaagcggg atttcccgcg aagc                                    34

<210> SEQ ID NO 38
<211> LENGTH: 23
<212> TYPE: DNA
<213> ORGANISM: Artificial Sequence
<220> FEATURE:
<223> OTHER INFORMATION: human NF-kB decoy DNA

<400> SEQUENCE: 38
ttgaagggat ttccctgcga agc                                                23

<210> SEQ ID NO 39
<211> LENGTH: 23
<212> TYPE: DNA
<213> ORGANISM: Artificial Sequence
<220> FEATURE:
<223> OTHER INFORMATION: human NF-kB decoy DNA

<400> SEQUENCE: 39
agggaaatcc cttcaagcga agc                                                23

<210> SEQ ID NO 40
<211> LENGTH: 48
<212> TYPE: DNA
<213> ORGANISM: Artificial Sequence
<220> FEATURE:
<223> OTHER INFORMATION: human NF-kB decoy DNA

<400> SEQUENCE: 40
tcaaggaaaa ccttgaaggg atttccctcc aaaaggaggg aaatccct                     48

<210> SEQ ID NO 41
<211> LENGTH: 20
<212> TYPE: DNA
<213> ORGANISM: Artificial Sequence
<220> FEATURE:
<223> OTHER INFORMATION: human NF-kB decoy DNA

<400> SEQUENCE: 41
ttgccgtacc tgacttagcc                                                    20

<210> SEQ ID NO 42
<211> LENGTH: 20
<212> TYPE: DNA
<213> ORGANISM: Artificial Sequence
<220> FEATURE:
<223> OTHER INFORMATION: human NF-kB decoy DNA

<400> SEQUENCE: 42
ggctaagtca ggtacggcaa                                                    20

<210> SEQ ID NO 43
<211> LENGTH: 34
<212> TYPE: DNA
<213> ORGANISM: Artificial Sequence
<220> FEATURE:
<223> OTHER INFORMATION: Combined DNA/RNA: firefly-luciferase-targeted
      siRNA
```

```
<400> SEQUENCE: 43
cgcgaagcga aggagccuuc aggauuacaa gauu                              34

<210> SEQ ID NO 44
<211> LENGTH: 34
<212> TYPE: DNA
<213> ORGANISM: Artificial Sequence
<220> FEATURE:
<223> OTHER INFORMATION: Combined DNA/RNA: firefly-luciferase-targeted
      siRNA

<400> SEQUENCE: 44
cgcgaagcga aucuuguaau ccugaaggcu ccuu                              34

<210> SEQ ID NO 45
<211> LENGTH: 43
<212> TYPE: DNA
<213> ORGANISM: Artificial Sequence
<220> FEATURE:
<223> OTHER INFORMATION: Combined DNA/RNA: firefly-luciferase-targeted
      siRNA

<400> SEQUENCE: 45
cgcgaagcga aggagccuuc aggauuacaa gauucgcgaa gcg                    43

<210> SEQ ID NO 46
<211> LENGTH: 43
<212> TYPE: DNA
<213> ORGANISM: Artificial Sequence
<220> FEATURE:
<223> OTHER INFORMATION: Combined DNA/RNA: firefly-luciferase-targeted
      siRNA

<400> SEQUENCE: 46
cgcgaagcga aucuuguaau ccugaaggcu ccuucgcgaa gcg                    43

<210> SEQ ID NO 47
<211> LENGTH: 21
<212> TYPE: DNA
<213> ORGANISM: Artificial Sequence
<220> FEATURE:
<223> OTHER INFORMATION: Combined DNA/RNA: human-survivin-targeted siRNA

<400> SEQUENCE: 47
ggaccaccgc aucucuacat t                                            21

<210> SEQ ID NO 48
<211> LENGTH: 21
<212> TYPE: DNA
<213> ORGANISM: Artificial Sequence
<220> FEATURE:
<223> OTHER INFORMATION: Combined DNA/RNA: human-survivin-targeted siRNA

<400> SEQUENCE: 48
uguagagaug cgguggucct t                                            21

<210> SEQ ID NO 49
<211> LENGTH: 25
<212> TYPE: DNA
<213> ORGANISM: Artificial Sequence
<220> FEATURE:
<223> OTHER INFORMATION: Combined DNA/RNA: human-survivin-targeted siRNA

<400> SEQUENCE: 49
ggaccaccgc aucucuacau ucaag                                        25
```

```
<210> SEQ ID NO 50
<211> LENGTH: 25
<212> TYPE: DNA
<213> ORGANISM: Artificial Sequence
<220> FEATURE:
<223> OTHER INFORMATION: Combined DNA/RNA: human-survivin-targeted siRNA

<400> SEQUENCE: 50
cuugaaugua gagaugcggu ggucc                                        25

<210> SEQ ID NO 51
<211> LENGTH: 34
<212> TYPE: DNA
<213> ORGANISM: Artificial Sequence
<220> FEATURE:
<223> OTHER INFORMATION: Combined DNA/RNA: human-survivin-targeted siRNA

<400> SEQUENCE: 51
ggaccaccgc aucucuacau ucaagcgcga agcg                              34

<210> SEQ ID NO 52
<211> LENGTH: 34
<212> TYPE: DNA
<213> ORGANISM: Artificial Sequence
<220> FEATURE:
<223> OTHER INFORMATION: Combined DNA/RNA: human-survivin-targeted siRNA

<400> SEQUENCE: 52
cuugaaugua gagaugcggu ggucccgcga agcg                              34

<210> SEQ ID NO 53
<211> LENGTH: 21
<212> TYPE: DNA
<213> ORGANISM: Artificial Sequence
<220> FEATURE:
<223> OTHER INFORMATION: Combined DNA/RNA: human-LaminA/C-targeted siRNA

<400> SEQUENCE: 53
ggugguyacg aucuggcut t                                             21

<210> SEQ ID NO 54
<211> LENGTH: 21
<212> TYPE: DNA
<213> ORGANISM: Artificial Sequence
<220> FEATURE:
<223> OTHER INFORMATION: Combined DNA/RNA: human-LaminA/C-targeted siRNA

<400> SEQUENCE: 54
agcccagauc gucaccacct t                                            21

<210> SEQ ID NO 55
<211> LENGTH: 25
<212> TYPE: RNA
<213> ORGANISM: Artificial Sequence
<220> FEATURE:
<223> OTHER INFORMATION: human-LaminA/C-targeted siRNA

<400> SEQUENCE: 55
gcagguggug acgaucuggg cugca                                        25

<210> SEQ ID NO 56
<211> LENGTH: 25
<212> TYPE: RNA
<213> ORGANISM: Artificial Sequence
<220> FEATURE:
<223> OTHER INFORMATION: human-LaminA/C-targeted siRNA
```

-continued

```
<400> SEQUENCE: 56
ugcagcccag aucgucacca ccugc                                              25

<210> SEQ ID NO 57
<211> LENGTH: 28
<212> TYPE: DNA
<213> ORGANISM: Artificial Sequence
<220> FEATURE:
<223> OTHER INFORMATION: Combined DNA/RNA: human-LaminA/C-targeted siRNA

<400> SEQUENCE: 57
gguggugacg aucugggcuc gcgaagcg                                           28

<210> SEQ ID NO 58
<211> LENGTH: 28
<212> TYPE: DNA
<213> ORGANISM: Artificial Sequence
<220> FEATURE:
<223> OTHER INFORMATION: Combined DNA/RNA: human-LaminA/C-targeted siRNA

<400> SEQUENCE: 58
agcccagauc gucaccaccc gcgaagcg                                           28

<210> SEQ ID NO 59
<211> LENGTH: 34
<212> TYPE: DNA
<213> ORGANISM: Artificial Sequence
<220> FEATURE:
<223> OTHER INFORMATION: Combined DNA/RNA: human-LaminA/C-targeted siRNA

<400> SEQUENCE: 59
gcagguggug acgaucuggg cugcacgcga agcg                                    34

<210> SEQ ID NO 60
<211> LENGTH: 34
<212> TYPE: DNA
<213> ORGANISM: Artificial Sequence
<220> FEATURE:
<223> OTHER INFORMATION: Combined DNA/RNA: human-LaminA/C-targeted siRNA

<400> SEQUENCE: 60
ugcagcccag aucgucacca ccugccgcga agcg                                    34

<210> SEQ ID NO 61
<211> LENGTH: 18
<212> TYPE: DNA
<213> ORGANISM: Artificial Sequence
<220> FEATURE:
<223> OTHER INFORMATION: Synthetic primer

<400> SEQUENCE: 61
catgggtgcc ccgacgtt                                                      18

<210> SEQ ID NO 62
<211> LENGTH: 18
<212> TYPE: DNA
<213> ORGANISM: Artificial Sequence
<220> FEATURE:
<223> OTHER INFORMATION: Synthetic primer

<400> SEQUENCE: 62
cctccaagaa gggccagt                                                      18

<210> SEQ ID NO 63
```

```
<211> LENGTH: 19
<212> TYPE: DNA
<213> ORGANISM: Artificial Sequence
<220> FEATURE:
<223> OTHER INFORMATION: Synthetic primer

<400> SEQUENCE: 63
tggcacccag cacaatgaa                                                    19

<210> SEQ ID NO 64
<211> LENGTH: 24
<212> TYPE: DNA
<213> ORGANISM: Artificial Sequence
<220> FEATURE:
<223> OTHER INFORMATION: Synthetic primer

<400> SEQUENCE: 64
tcatactcct gcttgctgat ccac                                              24

<210> SEQ ID NO 65
<211> LENGTH: 21
<212> TYPE: DNA
<213> ORGANISM: Artificial Sequence
<220> FEATURE:
<223> OTHER INFORMATION: Synthetic primer

<400> SEQUENCE: 65
gccagaatgg agatgatccc t                                                 21

<210> SEQ ID NO 66
<211> LENGTH: 19
<212> TYPE: DNA
<213> ORGANISM: Artificial Sequence
<220> FEATURE:
<223> OTHER INFORMATION: Synthetic primer

<400> SEQUENCE: 66
cttccacacc aggtcggta                                                    19

<210> SEQ ID NO 67
<211> LENGTH: 19
<212> TYPE: DNA
<213> ORGANISM: Artificial Sequence
<220> FEATURE:
<223> OTHER INFORMATION: Synthetic primer

<400> SEQUENCE: 67
gaaggtgaag gtcggagtc                                                    19

<210> SEQ ID NO 68
<211> LENGTH: 24
<212> TYPE: DNA
<213> ORGANISM: Artificial Sequence
<220> FEATURE:
<223> OTHER INFORMATION: Synthetic primer

<400> SEQUENCE: 68
tggcaacaat atccacttta ccag                                              24
```